United States Patent
Hyde et al.

(10) Patent No.: US 10,159,439 B2
(45) Date of Patent: *Dec. 25, 2018

(54) DEVICES AND METHODS FOR REMOTE HYDRATION MEASUREMENT

(71) Applicant: Elwha LLC, Bellevue, WA (US)

(72) Inventors: Roderick A. Hyde, Redmond, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 702 days.

This patent is subject to a terminal disclaimer.

(21) Appl. No.: 14/602,511

(22) Filed: Jan. 22, 2015

(65) Prior Publication Data
US 2016/0213315 A1    Jul. 28, 2016

(51) Int. Cl.
*A61B 5/00* (2006.01)
*A61B 90/90* (2016.01)
(Continued)

(52) U.S. Cl.
CPC .......... *A61B 5/4875* (2013.01); *A61B 5/0507* (2013.01); *A61B 5/746* (2013.01);
(Continued)

(58) Field of Classification Search
None
See application file for complete search history.

(56) References Cited

U.S. PATENT DOCUMENTS

| 4,384,288 A | 5/1983 | Walton |
| 4,973,964 A * | 11/1990 | Schuster ................. G01S 13/68 342/359 |

(Continued)

OTHER PUBLICATIONS

Armstrong, Lawrence E.; "Assessing Hydration Status: The Elusive Gold Standard"; Journal of the American College of Nutrition; bearing a date of Jul. 16, 2007; pp. 575S-584S; vol. 26, No. 5; American College of Nutrition.
(Continued)

*Primary Examiner* — Jacqueline Cheng
*Assistant Examiner* — Jairo Portillo

(57) ABSTRACT

Devices and methods are described for a hand-held hydration monitor including a micro-impulse radar component; a data storage component including stored information associated with reference reflected pulses correlated with reference hydration states; a user interface; and a computing component including a processor and circuitry, the circuitry including micro-impulse radar control circuitry configured to actuated the micro-impulse radar component, distance-finding circuitry configured to determine a distance between the hand-held hydration monitor and a target location on a subject, and hydration determination circuitry configured to receive information associated with one or more reflected pulses from a target tissue associated with the target location on the subject and to compare the information associated with the one or more reflected pulses from the target tissue with the stored information associated with the reference reflected pulses correlated with the reference hydration states to determine a relative hydration state of the target tissue.

41 Claims, 31 Drawing Sheets

(51) Int. Cl.
*A61B 90/98* (2016.01)
*A61B 5/05* (2006.01)

(52) U.S. Cl.
CPC .............. *A61B 90/90* (2016.02); *A61B 90/98* (2016.02); *A61B 5/0077* (2013.01); *A61B 5/443* (2013.01); *A61B 5/7221* (2013.01); *A61B 5/7246* (2013.01); *A61B 5/7278* (2013.01); *A61B 2560/0238* (2013.01); *A61B 2560/0425* (2013.01); *A61B 2560/0475* (2013.01); *A61B 2562/0257* (2013.01)

(56) References Cited

U.S. PATENT DOCUMENTS

| | | | |
|---|---|---|---|
| 5,345,471 | A | 9/1994 | McEwan |
| 5,361,070 | A | 11/1994 | McEwan |
| 5,573,012 | A | 11/1996 | McEwan |
| 5,774,091 | A | 6/1998 | McEwan |
| 6,417,797 | B1 | 7/2002 | Cousins et al. |
| 6,419,680 | B1 | 7/2002 | Cosman et al. |
| 6,433,720 | B1 | 8/2002 | Libove et al. |
| 7,215,976 | B2 | 5/2007 | Brideglall |
| 7,249,036 | B2 | 7/2007 | Bayne |
| 7,288,759 | B2 * | 10/2007 | Frangioni ............ G01N 23/223 250/252.1 |
| 8,427,242 | B2 | 4/2013 | Raphaeli et al. |
| 2002/0095087 | A1 | 7/2002 | Mourad et al. |
| 2004/0171962 | A1 | 9/2004 | Leveque et al. |
| 2004/0249257 | A1 | 12/2004 | Tupin, Jr. et al. |
| 2006/0122475 | A1 * | 6/2006 | Balberg ............... A61B 5/0097 600/323 |
| 2007/0010748 | A1 * | 1/2007 | Rauch ................. A61B 5/4863 600/481 |
| 2007/0016078 | A1 | 1/2007 | Hoyt et al. |
| 2008/0007445 | A1 * | 1/2008 | Leach, Jr. ........... G01S 13/0209 342/21 |
| 2008/0039718 | A1 | 2/2008 | Drinan et al. |
| 2008/0200802 | A1 | 8/2008 | Bhavaraju et al. |
| 2008/0262297 | A1 | 10/2008 | Gilboa et al. |
| 2008/0272955 | A1 * | 11/2008 | Yonak .................. G01S 13/931 342/54 |
| 2009/0192722 | A1 | 7/2009 | Shariati et al. |
| 2009/0213362 | A1 * | 8/2009 | Nakamura ........... A61B 5/0075 356/72 |
| 2009/0281421 | A1 | 11/2009 | Culp et al. |
| 2010/0049052 | A1 | 2/2010 | Sharf et al. |
| 2010/0234716 | A1 * | 9/2010 | Engel ................ A61B 5/02055 600/391 |
| 2010/0265121 | A1 * | 10/2010 | Bandhauer ........... G01S 7/2923 342/135 |
| 2010/0305454 | A1 | 12/2010 | Dvorsky et al. |
| 2010/0315280 | A1 * | 12/2010 | Bakhtar ................. G01S 13/02 342/22 |
| 2010/0324415 | A1 | 12/2010 | Drinan et al. |
| 2011/0166937 | A1 | 7/2011 | Bangera et al. |
| 2011/0196237 | A1 * | 8/2011 | Pelissier ................. A61B 8/06 600/454 |
| 2012/0137567 | A1 | 6/2012 | Sammut |
| 2012/0274498 | A1 | 11/2012 | Hyde et al. |
| 2012/0274502 | A1 | 11/2012 | Hyde et al. |
| 2012/0274503 | A1 | 11/2012 | Hyde et al. |
| 2012/0289832 | A1 * | 11/2012 | Zhang ................ G02B 21/0012 600/443 |
| 2014/0059915 | A1 | 3/2014 | Sammut et al. |
| 2014/0171749 | A1 * | 6/2014 | Chin .................... A61B 5/0015 600/300 |
| 2014/0194793 | A1 * | 7/2014 | Nakata ................ A61B 5/0816 601/48 |
| 2014/0296718 | A1 | 10/2014 | Kishima |
| 2015/0331091 | A1 * | 11/2015 | Abbasi .................. G01S 13/34 342/128 |

OTHER PUBLICATIONS

Azevedo; "Micropower Impulse Radar"; Science & Technology Review; Jan./Feb. 1996; pp. 16-29.

Chawla et al.; "An Overview of Passive RFID"; IEEE Applications & Practice; Sep. 2007; pp. 11-17; IEEE.

Dill et al.; "Calculation of percentage changes in volumes of blood, plasma, and red cells in dehydration"; Journal of Applied Physiology; Aug. 1974; pp. 247-248; vol. 37, No. 2.

Finkenzeller, Klaus; "Fundamental Operating Principles"; RFID Handbook: Fundamentals and Applications in Contactless Smart Cards and Identification; uploaded on Jan. 19, 2015; 31 pages; John Wiley & Sons, Ltd.

Gabriel et al.; "The dielectric properties of biological tissues: I. Literature survey"; Phys. Med. Biol.; bearing a date of Apr. 2, 1996; pp. 2231-2249; vol. 41; IOP Publishing Ltd.

Haddad et al.; "Microwave Hematoma Detector for the Rapid Assessment of Head Injuries"; U.S. Department of Energy—Lawrence Livermore National Laboratory; Feb. 11, 2000; 21 pages.

Lazebnik et al.; "Tissue-mimicking phantom materials for narrow-band and ultrawideband microwave applications"; Physics in Medicine and Biology; bearing a date of Apr. 29, 2005; pp. 4245-4258; vol. 50; IOP Publishing Ltd.

Levy et al.; "Micropower Impulse Radar: A Novel Technology for Rapid, Real-Time Detection of Pneumothorax"; Emergency Medicine International; bearing a date of Feb. 8, 2011; pp. 1-5; vol. 2011; Hindawi Publishing Corporation.

Meaney et al.; "Integration of microwave tomography with magnetic resonance for improved breast imaging"; Med. Phys.; Oct. 2013; pp. 103101-1~103101-13; vol. 40, No. 10; Am. Assoc. Phys. Med.

O'Halloran et al.; "Frequency-Dependent Modeling of Ultra-WideBand Pulses in Human Tissue for Biomedical Applications"; Dublin Institute of Technology; Jun. 28-30, 2006; pp. 297-301.

Pancera, Elena; "Medical Applications of the Ultra Wideband Technology"; 2010 Loughborough Antennas & Propagation Conference; Nov. 8-9, 2010; pp. 52-56; IEEE.

Paulson et al.; "Ultra-wideband Radar Methods and Techniques of Medical Sensing and Imaging"; SPIE International Symposium on Optics East; Oct. 10, 2005; 14 pages.

Perrier et al.; "Hydration biomarkers in free-living adults with different levels of habitual fluid consumption"; British Journal of Nutrition; bearing a date of Mar. 28, 2012; pp. 1678-1687; vol. 109; Danone Research.

Perrier et al.; "Relation between urinary hydration biomarkers and total fluid intake in healthy adults"; European Journal of Clinical Nutrition; bearing a date of Jan. 7, 2013; pp. 939-943; vol. 67; Macmillan Publishers Limited.

Szeliski, Richard; "Image Alignment and Stitching: A Tutorial"; Foundations and Trends in Computer Graphics and Vision; uploaded on Jan. 19, 2015 ; pp. 1-104; vol. 2, No. 1.

Zitová et al.; "Image registration methods: a survey"; Image and Vision Computing; bearing a date of Nov. 9, 2001; pp. 977-1000; vol. 21; Elsevier B.V.

* cited by examiner

2610 Receiving information associated with at least one first reflected pulse from a nearest surface of a target tissue of a subject with the hydration monitor, the hydration monitor including a micro-impulse radar component, a data storage component including stored information associated with reference reflected pulses correlated with reference hydration states, a user interface, and a computing component including a processor and circuitry

2620 Determining a distance from the hydration monitor to the subject using the information associated with the at least one first reflected pulse from the nearest surface of the target tissue of the subject

2630 Actuating the micro-impulse radar component to transmit one or more pulses to the target tissue of the subject

2640 Receiving information associated with one or more reflected pulses from the target tissue of the subject

2650 Comparing the received information associated with the one or more reflected pulses from the target tissue of the subject with the stored information associated with the reference reflected pulses correlated with the reference hydration states to determine a relative hydration state of the target tissue of the subject

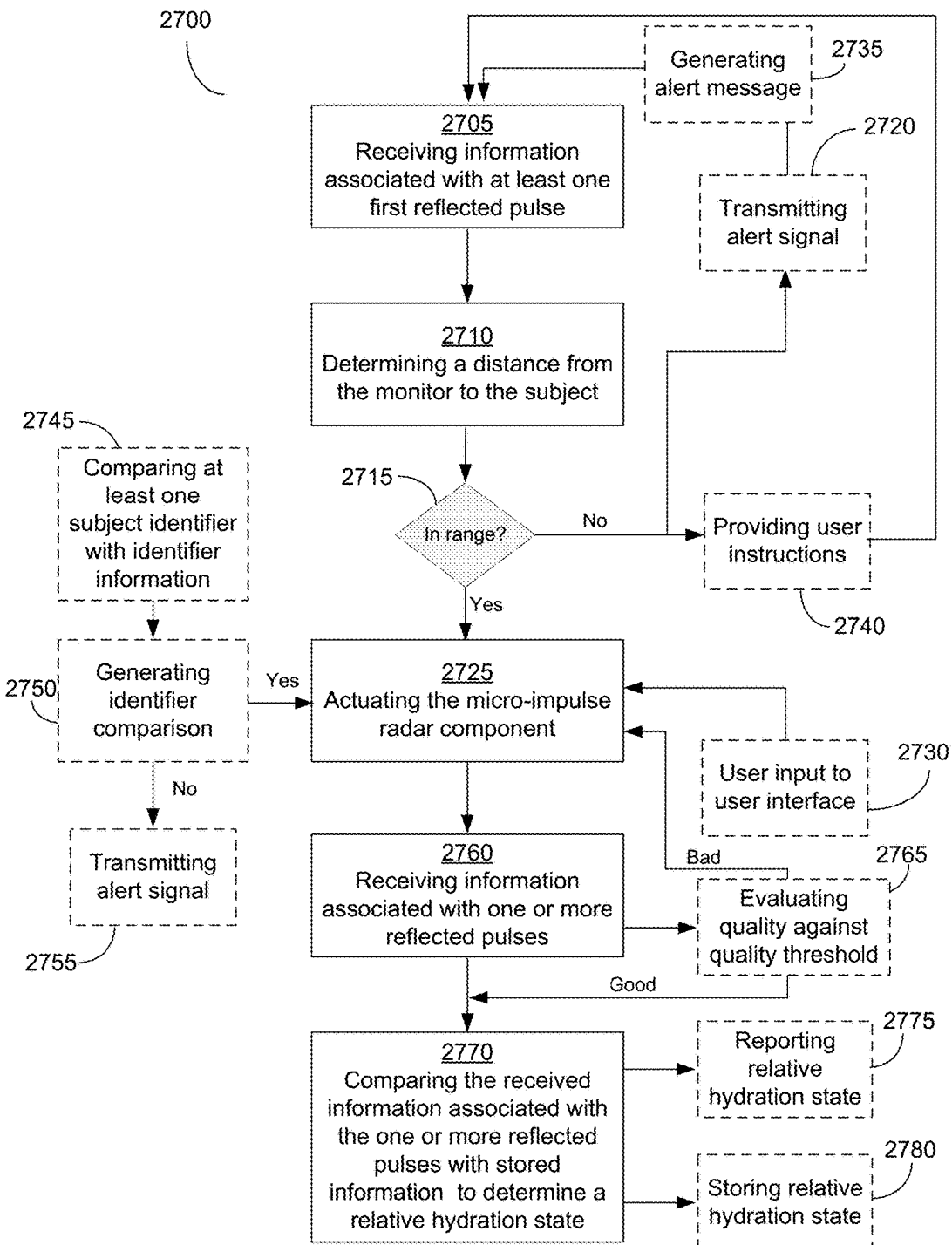

2810 Aligning a target on a subject with one or more alignment features in a viewfinder of a hydration monitor, the hydration monitor including the viewfinder, a micro-impulse radar component, a data storage component including stored information associated with reference reflected pulses correlated with reference hydration states, a user interface, and a computing component including a processor and circuitry 2820 Actuating the micro-impulse radar component to transmit one or more pulses towards the target on the subject 2830 Receiving information associated with one or more reflected pulses from a tissue associated with the target on the subject 2840 Comparing the received information associated with the one or more reflected pulses from the tissue associated with the target on the subject with the stored information associated with the reference reflected pulses correlated with the reference hydration states to determine a relative hydration state of the tissue

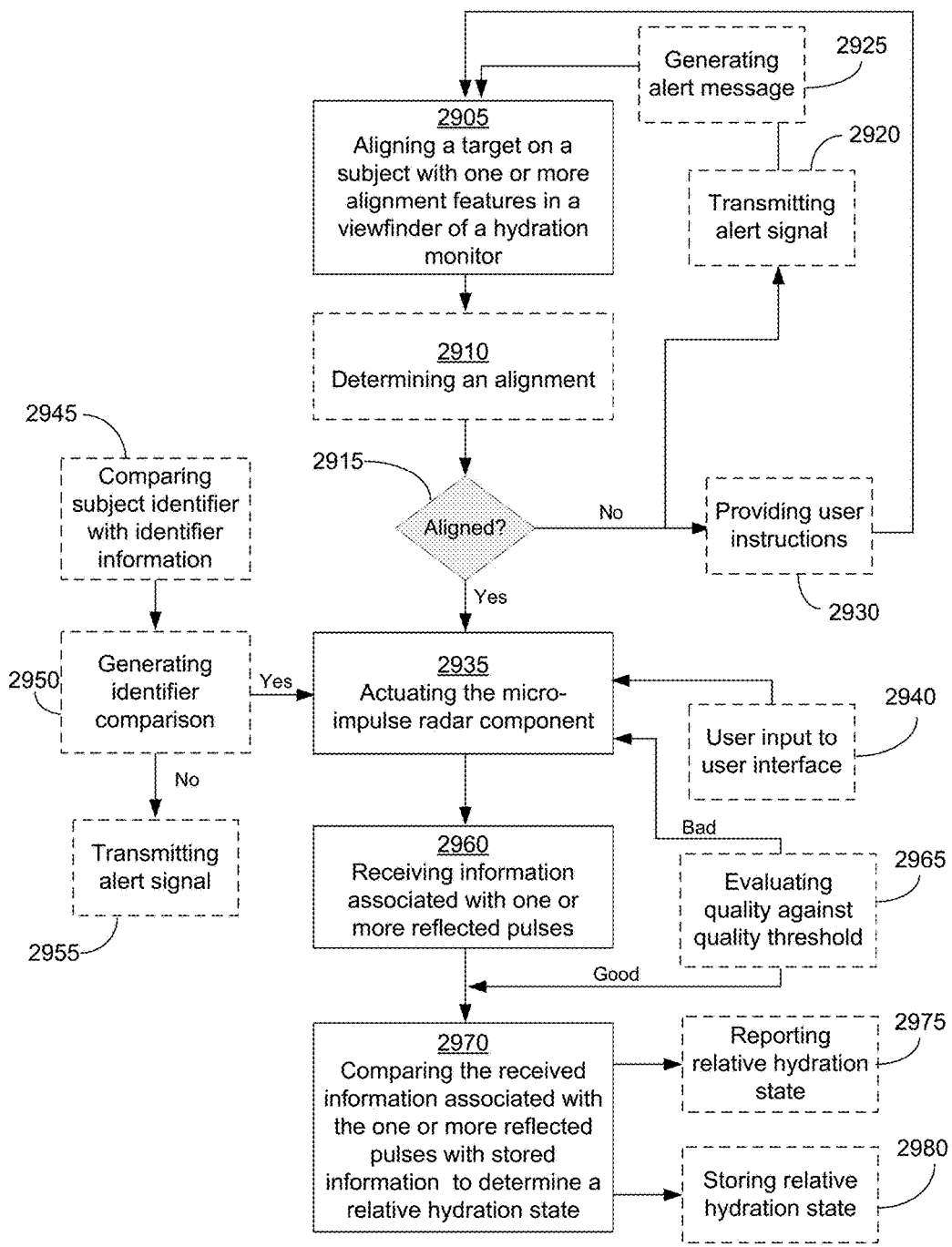

3010 Receiving information associated with a location on a subject from a location-capture component of the hydration monitor, the hydration monitor including the location-capture component, a micro-impulse radar component, a data storage component including stored location information and stored information associated with reference reflected pulses correlated with reference hydration states, a user interface, and a computing component including a processor and circuitry 3020 Comparing the received information associated with the location on the subject with the stored location information and determining a registration value 3030 Actuating the micro-impulse radar component to transmit one or more pulses to the location on the subject 3040 Receiving one or more reflected pulses from a tissue associated with the location on the subject 3050 Comparing information associated with the received one or more reflected pulses from the tissue associated with the location on the subject with the stored information associated with the reference reflected pulses correlated with the reference hydration states to determine a relative hydration state of the tissue

DEVICES AND METHODS FOR REMOTE HYDRATION MEASUREMENT

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority application(s)).

PRIORITY APPLICATIONS

None

If the listings of applications provided above are inconsistent with the listings provided via an ADS, it is the intent of the Applicant to claim priority to each application that appears in the Domestic Benefit/National Stage Information section of the ADS and to each application that appears in the Priority applications section of this application.

All subject matter of the Priority applications and of any and all applications related to the Priority applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a hand-held hydration monitor includes, but is not limited to, a micro-impulse radar component including a pulse generator and at least one antenna; a data storage component including stored information associated with reference reflected pulses correlated with reference hydration states; a user interface; and a computing component including a processor and circuitry, the circuitry including micro-impulse radar control circuitry configured to actuate the micro-impulse radar component, distance-finding circuitry configured to determine a distance between the hand-held hydration monitor and a target location on a subject, and hydration determination circuitry configured to receive information associated with one or more reflected pulses from a target tissue associated with the target location on the subject and to compare the received information associated with the one or more reflected pulses from the target tissue with the stored information associated with the reference reflected pulses correlated with the reference hydration states to determine a relative hydration state of the target tissue.

In an aspect, a hand-held hydration monitor includes, but is not limited to, a viewfinder including one or more alignment features configured to align with a target on a subject; a micro-impulse radar component including a pulse generator and at least one antenna; a data storage component including stored information associated with reference reflected pulses correlated with reference hydration states; a user interface; and a computing component including a processor and circuitry, the circuitry including micro-impulse radar control circuitry configured to actuate the micro-impulse radar component, and hydration determination circuitry configured to receive information associated with one or more reflected pulses from a tissue associated with the target on the subject and to compare the information associated with the one or more reflected pulses from the tissue associated with the target on the subject with the stored information associated with the reference reflected pulses correlated with the reference hydration states to determine a relative hydration state of the tissue.

In an aspect, a hand-held hydration monitor includes, but is not limited to, a location-capture component configured to capture information associated with a location on a subject; a micro-impulse radar component including a pulse generator and at least one antenna; a data storage component including stored location information and stored information associated with reference reflected pulses correlated with reference hydration states; a user interface; and a computing component including a processor and circuitry, the circuitry including registration circuitry configured to compare the captured information associated with the location on the subject with the stored location information to determine a registration value, micro-impulse radar control circuitry configured to actuate the micro-impulse radar component, and hydration determination circuitry configured to receive information associated with one or more reflected pulses from a tissue associated with the location on the subject and to compare the information associated with the one or more reflected pulses from the tissue with the stored information associated with the reference reflected pulses correlated with the reference hydration states to determine a relative hydration state of the tissue. In addition to the foregoing, other aspects of a hand-held hydration monitor are described in the claims, drawings, and text forming a part of the present disclosure.

In an aspect, a method of determining a hydration state with a hydration monitor includes, but is not limited to, receiving information associated with at least one first reflected pulse from a nearest surface of a target tissue of a subject with the hydration monitor, the hydration monitor including a micro-impulse radar component, a data storage component including stored information associated with reference reflected pulses correlated with reference hydration states, a user interface, and a computing component including a processor and circuitry; determining a distance from the hydration monitor to the subject using the information associated with the at least one first reflected pulse from the nearest surface of the target tissue of the subject; actuating the micro-impulse radar component to transmit one or more pulses to the target tissue of the subject; receiving information associated with one or more reflected pulses from the target tissue of the subject; and comparing the received information associated with the one or more reflected pulses from the target tissue of the subject with the stored information associated with the reference reflected pulses correlated with the reference hydration states to determine a relative hydration state of the target tissue of the subject.

In an aspect, a method of determining a hydration state with a hydration monitor includes, but is not limited to, aligning a target on a subject with one or more alignment features in a viewfinder of a hydration monitor, the hydration monitor including the viewfinder, a micro-impulse radar component, a data storage component including stored information associated with reference reflected pulses correlated with reference hydration states, a user interface, and a computing component including a processor and circuitry; actuating the micro-impulse radar component to transmit one or more pulses towards the target on the subject; receiving information associated with one or more reflected pulses from a tissue associated with the target on the subject; and comparing information associated with the one or more reflected pulses from the tissue associated with the target on the subject with the stored information associated with the reference reflected pulses correlated with the reference hydration states to determine a relative hydration state of the tissue.

In an aspect, a method of determining a hydration state with a hydration monitor includes, but is not limited to, receiving information associated with a location one a subject from a location-capture component of the hydration monitor, the hydration monitor including the location-capture component, a micro-impulse radar component, a data storage component including stored location information and stored information associated with reference reflected pulses correlated with reference hydration states, a computing component including a processor and circuitry; comparing the received information associated with the location on the subject with the stored location information and determining a registration value; actuating the micro-impulse radar component to transmit one or more pulses to the location on the subject; receiving one or more reflected pulses from a tissue associated with the location on the subject; and comparing the information associated with the received one or more reflected pulses from the tissue associated with the location on the subject with the stored information associated with the reference reflected pulses correlated with the reference hydration states to determine a relative hydration state of the tissue. In addition to the foregoing, other aspects of a method for determining a hydration state with a hydration monitor are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 26 is a flowchart of an embodiment of a method of determining a hydration state with a hydration monitor.

FIG. 27 is a flowchart illustrating further aspects of a method such as shown in FIG. 26.

FIG. 28 is a flowchart of an embodiment of a method of determining a hydration state with a hydration monitor including a viewfinder.

FIG. 29 is a flowchart illustrating further aspects of a method such as shown in FIG. 28.

FIG. 30 is a flowchart of an embodiment of a method of determining a hydration state with a hydration monitor including a location-capture component.

DETAILED DESCRIPTION

Figure 1:
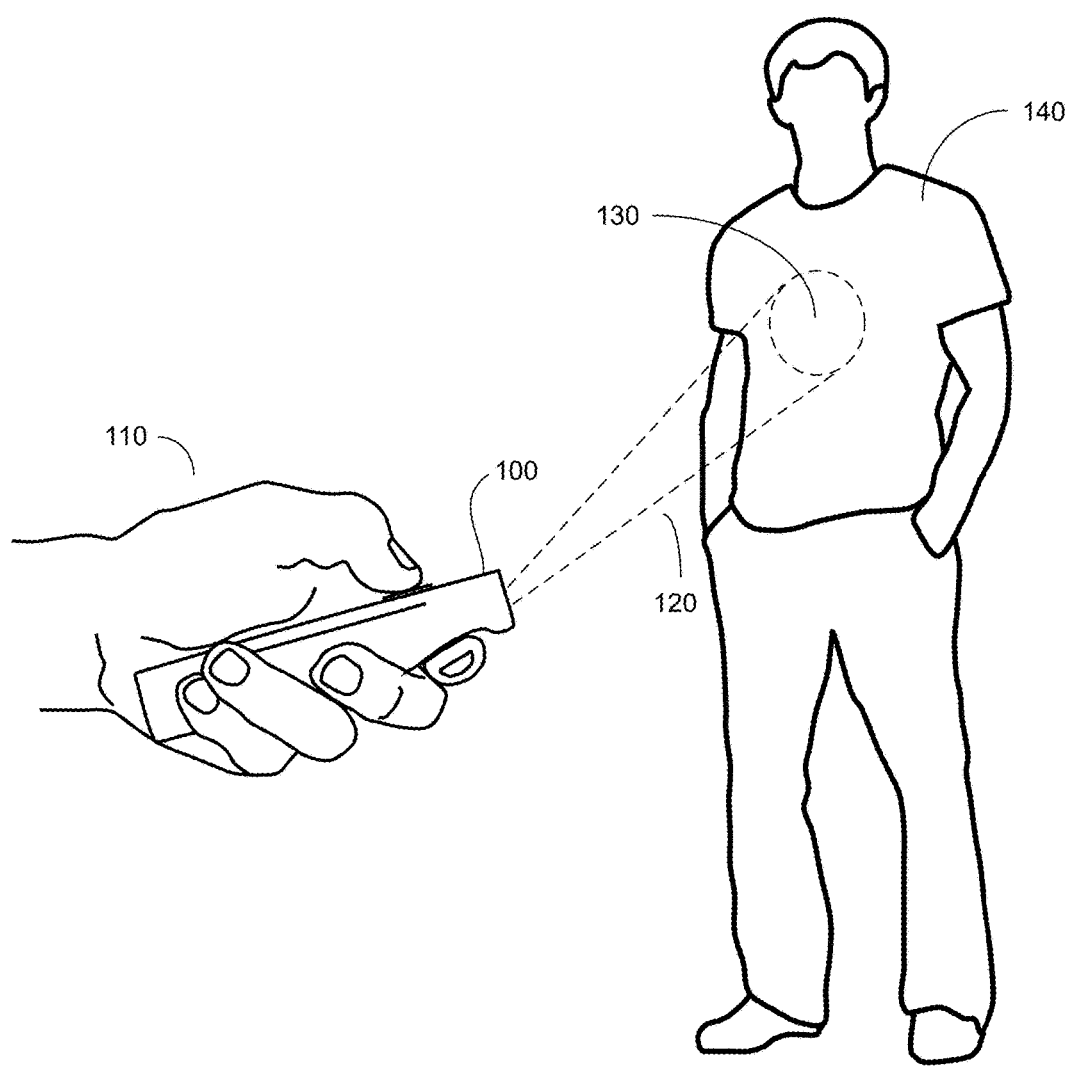
FIG. 1 illustrates an embodiment of a hand-held hydration monitor.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In mammals, water makes up as much as 70% of the total body mass. For example, water constitutes approximately 63% of the total body mass in adult humans and 65% and 70% respectively in children and infants. Water is the medium of circulatory function, biochemical reaction, metabolism, substrate transport, waste disposal, heat dispersion, temperature regulation, and numerous other physiological processes. As such, maintaining proper hydration conditions is important to both physical and mental state of an individual.

Dehydration is a condition in which the loss of body fluids, mostly water, exceeds the amount taken in. On a daily basis, water is involuntarily lost from the body through water vapor during respiration and in feces and urine. In addition, water is lost through excreted sweat as the body tries to regulate its temperature. The sensation of thirst becomes apparent when water loss approaches 1%-2% of total body mass. As dehydration progress, symptoms become increasingly severe and susceptibility to dehydration-related conditions, such as heat exhaustion and/or heat stroke, increases. Signs and symptoms of mild dehydration (2%-4% of body mass) include initial onset thirst, dry mucous membranes, mild fatigue, loss of appetite, headaches, loss of concentration, irritability, decreased blood pressure, and dizziness or fainting upon standing. Moderate dehydration (4-%-7% loss of body mass) may result in lethargy or extreme sleepiness, nausea, confusion, tingling in limbs, heat cramps, seizures, fainting and significant decreases in aerobic power and endurance. With severe dehydration (8%-10% low of body mass), muscles may become spastic, skin may shrivel and wrinkle, vision may dim, urination may become painful, delirium may begin and recovery without assistance may be impossible. A body weight loss greater than 10-12% can be fatal.

Dehydration, and dehydration-related conditions are extremely common, and the morbidity and mortality associated with them can be a burden to the healthcare system and to society. If detected early, however, dehydration and dehydration-related conditions are extremely easy to treat. As such, devices, systems, and methods are described herein for remotely measuring the relative hydration state of an individual using micro-impulse radar.

Electromagnetic pulses generated by micro-impulse radar are able to penetrate tissue. Each time a pulse encounters an interface, a portion of the radiated pulse is transmitted through the interface and a portion is reflected back. The transmission and reflection of the pulse depend on the dielectric properties of the materials. Biological tissues exhibit characteristic dielectric properties that change with frequency over the entire electromagnetic spectrum. Different tissues have different dielectric constants and conductivity, both of which are frequency dependent. See, e.g., Gabriel et al. (1996) "The dielectric properties of biological tissues: I. Literature Survey," Phys. Med. Biol. 41:2231-2249, which is incorporated herein by reference. In the microwave frequency range, for example, these variations can be attributed to the dipole relaxation of water molecules within the tissue. In addition, different tissues have different permittivity due to varying water content. As dehydration is often accompanied by changes in volumes of blood, plasma, and red blood cells (see, e.g., Dill & Costill (1974) "Calculation of percentage changes in volumes of blood, plasma, and red cells in dehydration," J. Appl. Physiol. 37:247-248, which is incorporated herein by reference), differences in dielectric properties and permittivity in hydrated and dehydrated states can be measured as differences in the properties of the reflected pulses.

With reference to FIG. 1, shown is an example of a hand-held hydration monitor 100 which can serve as a context for introducing one or more processes and/or devices described herein. As shown in FIG. 1, a user 110 is shown holding a hand-held hydration monitor 100 and remotely determining a hydration state of subject 140. Hand-held hydration monitor 100 includes a micro-impulse radar component including a pulse generator configured to rapidly transmit one or more pulses 120 of wideband radar. In this example, the transmitted one or more pulses 120 are aimed at a target 130 on a subject 140. The surface of the subject 140 as well as tissue and tissue interfaces underlying target 130 selectively reflect, refract, absorb, and/or otherwise scatter the transmitted one or more pulses 120. A return signal including a reflected, refracted, absorbed, and/or otherwise scattered signal can be received by an antenna associated with the hand-held hydration monitor 100. Hand-held hydration monitor 100 further includes a computing component with a processor and circuitry configured to determine a relative hydration state of subject 140 based on the one or more reflected pulses.

In an aspect, hand-held hydration monitor 100 is configured to determine a relative hydration state of a subject. In an aspect, the subject includes an athlete. For example, the hand-held hydration monitor can be configured to determine a relative hydration state of an athlete before, during, and/or after a period of physical activity. In an aspect, the subject includes a laborer. For example, the hand-held hydration monitor can be configured to determine a relative hydration state of a laborer (e.g., a construction worker) before, during, and/or after a period of physical labor. In an aspect, the subject includes a member of the armed forces. In an aspect, the subject includes a firefighter or other individual working with heavy gear and/or clothing under extreme conditions. In an aspect, the subject includes any individual involved in an activity, be it work or play, with a risk of dehydration. In an aspect, the subject includes a patient. For example, the hand-held hydration monitor can be configured to determine a relative hydration state of a patient upon arrival at a clinic, during a physical exam, and/or while admitted to a hospital. For example, the hand-held hydration monitor can be configured for home use to monitor a hydration state of a child or other household member experiencing a fever, vomiting, diarrhea, or other dehydrating event.

In an aspect, hand-held hydration monitor 100 is sized for use with one or both hands. In an aspect, the hand-held hydration monitor is of a weight and size to allow a user to "aim" the monitor with one or both hands at a subject from a distance. In some embodiments, the hand-held hydration monitor is mounted. For example, the hand-held hydration monitor can be mounted on a tripod or other free-standing support structure. For example, the hand-held hydration monitor can be mounted on a wall.

In an aspect, the user 110 includes an individual monitoring a subject for dehydration. For example, the user can include a parent or other caregiver monitoring dehydration in a child experiencing a fever, vomiting, diarrhea, or other dehydrating event. In an aspect, the user includes an individual associated with an athlete, an athletic team, an athletic facility, or an athletic activity. For example, the user can include a coach, a trainer, a team physician, a teacher, or a parent. In an aspect, the user includes an individual monitoring a labor force (e.g., construction workers, miners, military personnel, firefighters). For example, the user can include a member of the labor force, an inspector, or medical personnel. In an aspect, the user includes a medical professional monitoring a patient for dehydration. For example, the user can include a nurse, a nurse practitioner, a nurse's assistant or aide, a doctor, an orderly, a homecare provider, a physical therapist, or any other medical professional. For example, the user can be associated with a medical clinic or hospital. For example, the user can be associated with a field clinic, hospital, or triage center.

In some embodiments, the hand-held hydration monitor functions autonomously. For example, a hand-held hydration monitor mounted on a wall or on a free-standing support structure may be configured to automatically determine a hydration state of a subject standing within a distance that falls within a range of predetermined operating distances of the hand-held hydration monitor. For example, the hand-held hydration monitor may be mounted on the wall of an athletic facility (e.g., a gym) or a medical facility (e.g., an emergency room or other triage center), and configured to automatically determine a hydration state of a subject standing at an appropriate distance from the monitor.

In some embodiments, a hand-held hydration monitor includes a micro-impulse radar component including a pulse generator and at least one antenna; a data storage component including stored information associated with reference reflected pulses correlated with reference hydration states; a user interface; and a computing component including a processor and circuitry, the circuitry including micro-impulse radar control circuitry configured to actuate the micro-impulse radar component; distance-finding circuitry configured to determine a distance between the hand-held hydration monitor and a target location on a subject; and hydration determination circuitry configured to receive information associated with one or more reflected pulses from a target tissue associated with the target location on the subject and to compare the information associated with the one or more reflected pulses from the target tissue with the stored information associated with the reference reflected pulses correlated with the reference hydration states to determine a relative hydration state of the target tissue.

Figure 2:
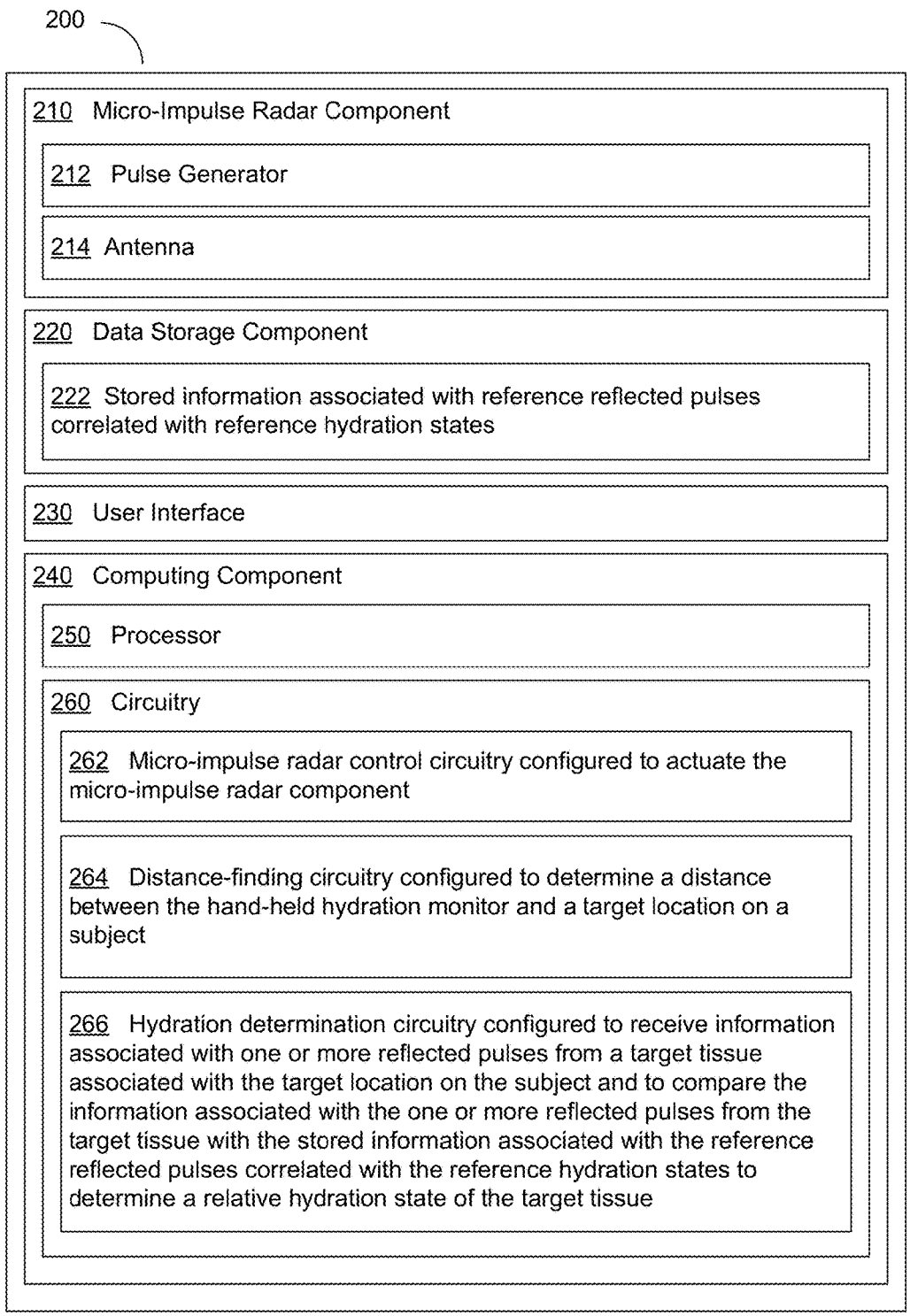
FIG. 2 is a block diagram of an embodiment of a hand-held hydration monitor.

FIG. 2 is a simplified block diagram illustrating an embodiment of a hand-held hydration monitor. Hand-held hydration monitor 200 includes micro-impulse radar component 210. Micro-impulse radar component 210 includes pulse generator 212 and at least one antenna 214. Pulse generator 212 is configured to generate pulses of electromagnetic energy. In an aspect, at least one antenna 214 includes at least one antenna configured to transmit one or more pulses generated by pulse generator 212. In an aspect, at least one antenna 214 includes at least one antenna configured to receive one or more reflected pulses.

Hand-held hydration monitor 200 further includes data storage component 220 including stored information 222 associated with reference reflected pulses correlated with reference hydration states. For example, data storage component 220 can store a look-up table having a series of reference reflected pulses, e.g., pulse or signal patterns, correlated with reference hydration states. Hand-held hydration monitor 200 further includes user interface 230. In an aspect, user interface 230 is configured to transmit information to a user, e.g., alert messages, instructions, and/or a determined hydration state. In an aspect, user interface 230 is configured to receive information from a user, e.g., subject identification information, operating parameters, and the like. In an aspect, the user interface 230 includes a display, e.g., a touchscreen display. In an aspect, the user interface 230 includes at least one of a haptic or audio interface. In an aspect, user interface 230 includes at least one optical indicator, e.g., a green and/or a red light.

Hand-held hydration monitor 200 further includes computing component 240 including processor 250 and circuitry 260. Circuitry 260 includes micro-impulse radar control circuitry 262 configured to actuate the micro-impulse radar component. Circuitry 260 includes distance-finding circuitry 264 configured to determine a distance between the hand-held hydration monitor and a target location on a subject. Circuitry 260 further includes hydration determination circuitry 266 configured to receive information associated with one or more reflected pulses from a target tissue associated with the target location on the subject and to compare the information associated with the one or more reflected pulses from the target tissue with the stored information associated with the reference reflected pulses correlated with the reference hydration states to determine a relative hydration state of the target tissue.

Figure 3:
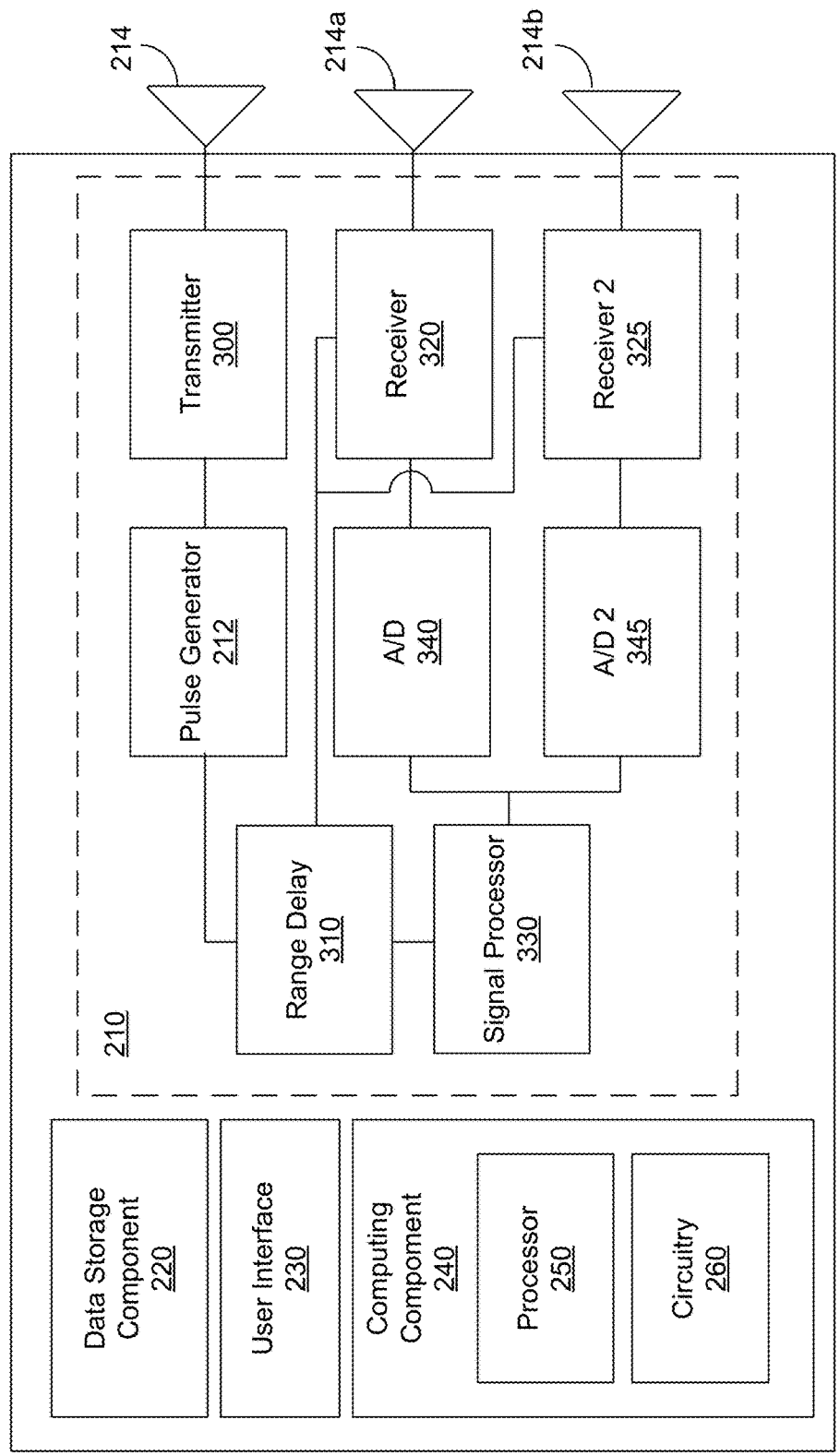
FIG. 3 is a block diagram illustrating aspects of a hand-held hydration monitor such as shown in FIG. 2.

FIG. 3 is a simplified block diagram showing further non-limiting aspects of micro-impulse radar component 210. In an aspect, micro-impulse radar component 210 includes micro-power impulse radar. See, e.g., U.S. Pat. No. 5,361,070 to McEwan titled "Ultra-wideband radar motion sensor;" U.S. Pat. No. 5,573,012 to McEwan titled "Body monitoring and imaging apparatus and method;" U.S. Pat. No. 5,774,091 to McEwan titled "Short Range Micro-Power Impulse Radar with High Resolution Range Gate with Damped Transmit and Receive Cavities;" Azevedo & McEwan (1996) Science & Technology Review, January/February, pp. 17-29, which are incorporated herein by reference. In an aspect, micro-impulse radar component 210 includes ultra-wideband radar. In an aspect, the micro-impulse radar component 210 transmits individual pulses that contain a wideband of microwave frequencies. In an aspect, the shorter the pulse transmitted, the wider the band of frequencies. Micro-impulse radar component 210 includes pulse generator 212 and at least one antenna 214. In an aspect, the pulse generator generates electromagnetic frequencies of about 200 kHz to about 100 GHz. In an aspect, the pulse generator generates electromagnetic energy at microwave frequencies. In an aspect, the lower cut-off frequency is dependent on the size of the antennas while wave penetration into the body limits the upper frequencies. In an aspect, pulse generator 212 includes a step recovery diode, a snap-off diode, a charge storage diode, or a varactor. In an aspect, pulse generator 212 includes a nonlinear transmission line (NLTL). In an aspect, pulse generator 212 includes an avalanche transistor. In an aspect, pulse generator 212 includes rapid automatic cascade exchange (RACE). See, e.g., U.S. Pat. No. 6,433,720 to Libove et al. titled "Methods, apparatuses, and systems for sampling or pulse generation," which is incorporated herein by reference. In an aspect, the pulse generator is incorporated into an integrated chip. See, e.g., U.S. Pat. No. 8,427,242 to Raphaeli & Shasha titled "Ultra Wideband On-Chip Pulse Generator," which is incorporated herein by reference.

In an aspect, pulse generator 212 is configured to output a relatively short duration voltage pulse that is applied to an antenna 214, e.g., a transmit antenna. In an aspect, antenna 214 is configured to transmit one or more pulses towards the target tissue. In an aspect, a separate antenna 214a is configured to receive one or more reflected pulses from the target tissue. In an aspect, antenna 214 is configured to both transmit and receive pulses. In an aspect, the at least one antenna includes at least one orthogonal transmitting antenna. In an aspect, the at least one antenna includes at least one horizontal antenna configured to receive horizontally polarized pulses.

In an aspect, a typical transmitted pulse width can be between about 100 picoseconds and about 5 nanoseconds. The voltage pulse can be conditioned and amplified (or attenuated) for output by transmitter 300. In an aspect, the transmitter is configured to emit rapid, wideband radar pulses at a nominal rate of 2 million per second. For example, transmitter 300 can transmit the voltage pulse or can further condition the pulse, such as to be differentiating a leading and/or trailing edge to produce short sub-nanosecond transmitted pulses. In an aspect, the voltage pulse transmission spectrum is the frequency domain transform of the emitted pulse. In an aspect, micro-impulse radar component 210 probes a subject by emitting a series of spaced voltage pulses. For example, the series of voltage pulses can be spaced between about 100 nanoseconds and 100 microseconds apart. In an aspect, the emitted series of voltage pulses can be characterized by spectral components having high penetration that can pass through a subject. The surface of the subject as well as tissue and tissue interfaces can selectively reflect, refract, absorb, and/or otherwise scatter the emitted pulses. A return signal including a reflected, refracted, absorbed, and/or otherwise scattered signal can be received by an antenna 214a, e.g., a receive antenna. Optionally, the receive antenna and the transmit antenna can be combined into a single antenna. In an aspect, a filter, a range gate, or a time-gate can be used to separate the return signal from the emitted pulse.

Distance can be determined by a range delay 310 configured to trigger a receiver 320 operably coupled to receive antenna 214a. For example, the receiver 320 can include a voltage detector such as a capture-and-hold capacitor or network. In an aspect, the range delay corresponds to the distance to the subject. In an aspect, the range delay can be modulated to capture information corresponding to different distances. In an aspect, the range delay can be modulated to capture information corresponding to different tissue depths. In an aspect, the receiver 320 uses a pulse-detector circuit to accept reflected pulses within a preset distance (round-trip delay time) from a few centimeters to tens of meters. Non-limiting examples of receivers are described in U.S. Pat. No. 5,345,471 to McEwan titled "Ultra-Wideband Receiver;" U.S. Pat. No. 5,774,091 to McEwan titled "Short Range Micro-Power Impulse Radar with High resolution Swept Range Gate with Damped Transmit and Receive Cavities," which are incorporated herein by reference.

Signal processor 330 can be configured to receive signals or data from receiver 320 and the analog-to-digital converter (A/D) 340, and by correlating range delay to the received signals or data from the receiver 320, extract information associated with the probed subject and/or tissue of the subject. Processing of received signals can be used to identify tissue variations.

Optionally, the micro-impulse radar component can include a second antenna 214b. In an aspect, the second antenna can be operably coupled to a second receiver 325 coupled to an output of the range delay 310 or a separate range delay configured to provide a delay selected for a depth into the subject, e.g., a depth into the tissue. The signal processor 330 can further receive output from a second A/D converter 345 operably coupled to the second receiver 325.

In an aspect, signal processor 330 can be configured to compare detection signals received by antenna 214a and 214b. For example, the signal processor 330 can search for common signal characteristics such as similar reflected static signal strength or spectrum, similar (or corresponding) Doppler shift, and/or common periodic motion component, and compare the respective range delays corresponding to detection by the respective antennas 214a and 214b. The triangulated locations can be output as computed ranges of angle or computed ranges of extent. For example, a first signal corresponding to a reflected pulse received by antenna 214a can be digitized by A/D converter 340 to form a first digitized waveform. A second signal corresponding to the reflected pulse received by antenna 214b can be digitized by A/D converter 340 or 345 to form a second digitized waveform. Signal processor 330 can compare the first and second digitized waveforms and deduce angular information from the first and second digitized waveforms and known geometry of the first and second antenna elements.

In an aspect, a second pulse can be received at a second range delay value and be similarly signal-processed to produce a second set of angular information that maps a second surface at a different distance. Depth within a given range delay can be inferred from a strength of the reflected pulse. A greater number of pulses can be combined to provide additional depth information. In an aspect, a series of pulses can be combined to form a time series of signals corresponding to the subject that includes hydration information of the subject.

In an aspect, the signal processor 330 outputs microimpulse radar data, e.g., information associated with one or more reflected pulses from the target tissue. In an aspect, the micro-impulse radar data can include spatial information, time-domain motion information, and/or frequency domain information. In an aspect, the micro-impulse radar data can be output in the form of an image. For example, the micro-impulse radar data in the form of an image can include a surface slice made of pixels or a volume made of voxels. Optionally, the image can include vector information.

In an aspect, the signal processor 330 of the microimpulse radar component 210 can transmit information, e.g., information associated with the one or more reflected pulses from the target tissue, to the computing component 240 of the hand-held hydration monitor. For example, the micro-impulse radar component 210 can include a high speed interface configured to output micro-impulse radar data from the signal processor. For example, the information associated with the one or more reflected pulses from the target tissue can be analyzed by circuitry 260 of computing component 240, e.g., the hydration determination circuitry, to determine a relative hydration state of the target tissue.

In an aspect, at least a portion of micro-impulse radar component 210 can be integrated into computing component 240. In an aspect, micro-impulse radar component 210 can include at least one antenna 214 formed as electrical traces on a circuit board of computing component 240. In an aspect, micro-impulse radar component 210 can include a pulse generator 212 and a range delay embodied as operations of a processor 250. In an aspect, micro-impulse radar component 210 can include at least one receiver embodied as one or more capture-and-held capacitors on a circuit board of computing component 240 and/or integrated into processor 250 and operably coupled to the at least one antenna 214. In an aspect, micro-impulse radar component 210 can include a signal processor 330 embodied as software or firmware running on processor 250.

Figure 4:
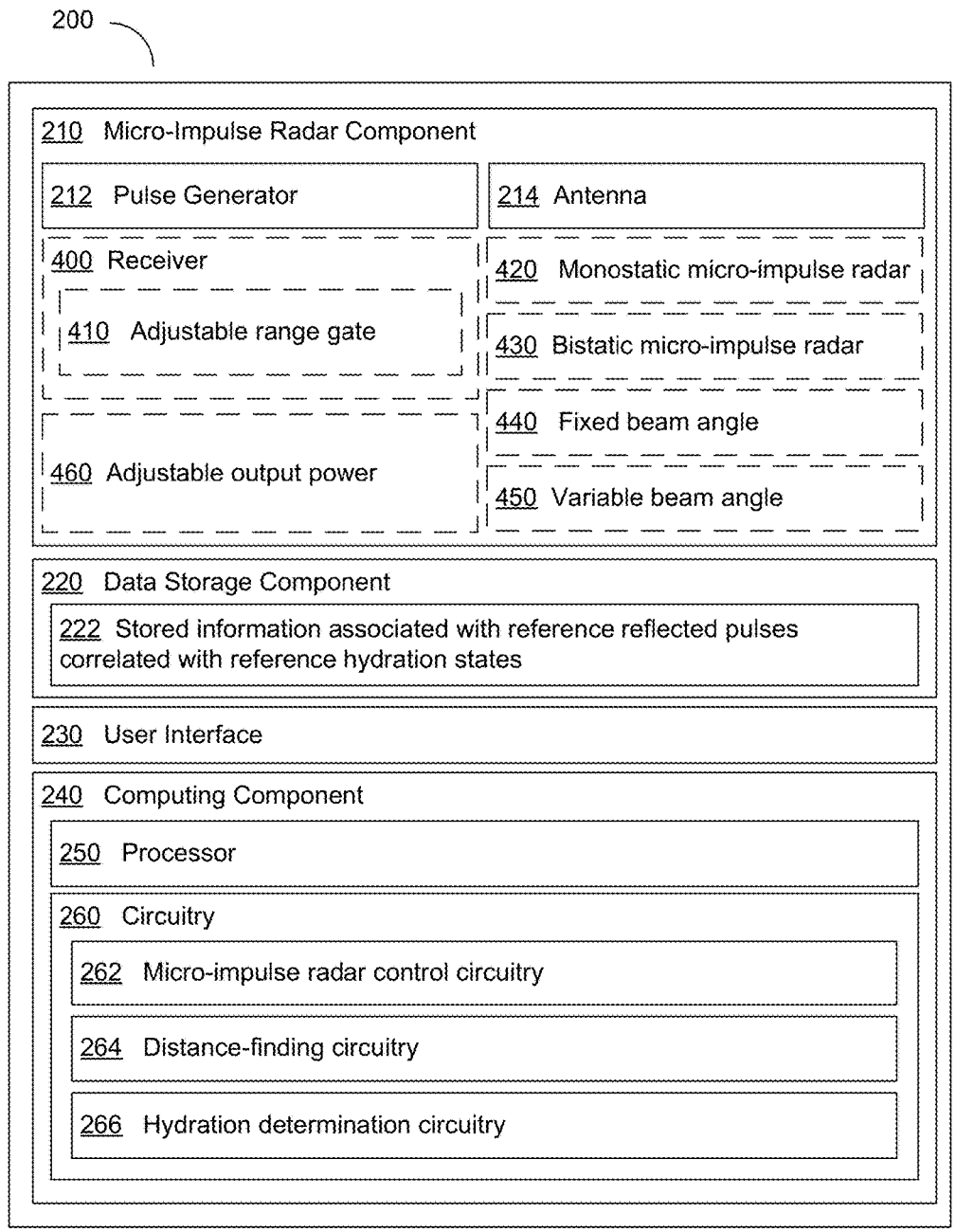
FIG. 4 is a block diagram showing aspects of a hand-held hydration monitor such as depicted in FIG. 2.

FIG. 4 illustrates further aspects of hand-held hydration monitor 200. A hand-held hydration monitor includes microimpulse radar component 210 including pulse generator 212 and at least one antenna 214. In an aspect, micro-impulse radar component 210 includes receiver 400. In an aspect, receiver 400 is configured to receive signals from at least one antenna 214, the received signals including one or more reflected pulses from the target tissue. For example, the receiver can include a voltage detector such as a capture-and-hold capacitor or network. In an aspect, receiver 400 includes an adjustable range gate 410. In an aspect, the adjustable range gate acts as a filter to extract desired reflected pulses. In an aspect, the range gate is configured to sample reflected pulses at specific time-slots. In an aspect, the specific time-slots are correlated with tissue depth. For example, the range gate may be set to acquire pulses reflected from a specific tissue depth, e.g., a depth of 2-5 centimeters. It is anticipated that the velocity of the transmitted pulses and subsequent reflections will slow down the deeper the transmitted pulse travels into the tissue.

In an aspect, the micro-impulse radar component 210 includes monostatic micro-impulse radar 420. In an aspect, the monostatic micro-impulse radar 420 includes a transmitter and a receiver that are collocated. In an aspect, substantially the entire micro-impulse radar component 210 is in the hand-held hydration monitor 200.

In an aspect, the micro-impulse radar component 210 includes bistatic micro-impulse radar 430. In an aspect, the bistatic micro-impulse radar 430 includes a transmitter and a receiver that are not collocated. In an aspect, the hand-held hydration monitor includes at least a portion of the micro-impulse radar component and at least a portion of the micro-impulse radar component is located separately. For example, the hand-held hydration monitor can include at least one of at least one transmitter or at least one receiver component. For example, a transmit antenna can be associated with the hand-held hydration monitor and at least one receive antenna located in a separate location, e.g., on the other side of a sports field, facility, gym, or arena.

In an aspect, the micro-impulse radar component 210 includes a multistatic micro-impulse radar component. In an aspect, the multistatic micro-impulse radar component includes multiple spatially diverse monostatic radar or bistatic radar components with a shared area of coverage. For example, the multistatic radar can include one receiver and two transmitters, or two receivers and one transmitter, or multiple receivers and multiple transmitters.

In an aspect, the micro-impulse radar component 210 includes a fixed beam angle 440. In an aspect, the fixed beam angle 440 of the micro-impulse radar component 210 is about 2 degrees to about 50 degrees. For example, the fixed beam angle of the micro-impulse radar component can be 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 16 degrees, 17 degrees, 18 degrees, 19 degrees, 20 degrees, 21 degrees, 22 degrees, 23 degrees, 24 degrees, 25 degrees, 26 degrees, 27 degrees, 28 degrees, 29 degrees, 30 degrees, 35 degrees, 40 degrees, 45 degrees, or 50 degrees.

In an aspect, the micro-impulse radar component 210 includes variable beam angle 450. For example, the micro-impulse radar component can include an adjustable beam angle. In an aspect, the variable beam angle 450 ranges from about 2 degrees to about 50 degrees.

In an aspect, the beam width at the target tissue is dependent upon the beam angle and the distance between the hand-held hydration monitor and the subject. An estimate of beam width can be calculated using trigonometry as follows:

$$\text{beam width} = 2\left(\text{distance} \times \left(\sin\left(\frac{\text{angle}}{2}\right)\right)\middle/\cos\left(\frac{\text{angle}}{2}\right)\right)$$

wherein the distance is to the center of the target tissue and the angle (in degrees) is the beam angle of the micro-impulse radar component. For example, a beam angle of 10 degrees will generate a beam width of approximately 0.5 feet or 6 inches at a distance of 3 feet. If the desired beam width at the target is 4 inches, then the user would need to decrease the distance between the hand-held hydration monitor and the subject. With a variable beam angle, the user could either adjust the beam angle for the given distance or decrease the distance for the given beam angle. In an aspect, the hand-held hydration monitor includes beam width control circuitry configured to adjust a beam width of the micro-impulse radar component in response to the determined distance. For example, the beam width control circuitry can be configured to calculate an appropriate beam width to just cover the target tissue and to adjust the beam angle based on the distance between the hand-held hydration monitor and the subject to achieve the calculated beam width.

In an aspect, the micro-impulse radar component 210 includes adjustable output power 460. For example, the transmitter can include an adjustable output power. For example, the transmit power can range from a peak transmit power of 60 milliwatts to an average transmit power of 25 microwatts or less. See, e.g., Paulson et al. (2005) "Ultra-wideband Radar Methods and Techniques of Medical Sensing and Imaging," SPIE International Symposium on Optics East, Boston, Mass., Oct. 25-26, 2005, which is incorporated herein by reference. In an aspect, the micro-impulse radar circuitry includes circuitry configured to adjust an output power of the micro-impulse radar component in response to the determined distance. For example, the output power may be decreased as the determined distance between the hand-held hydration monitor and the subject decreases. For example, the output power may be increased as the determined distance between the hand-held hydration monitor and the subject increases.

Figure 5:
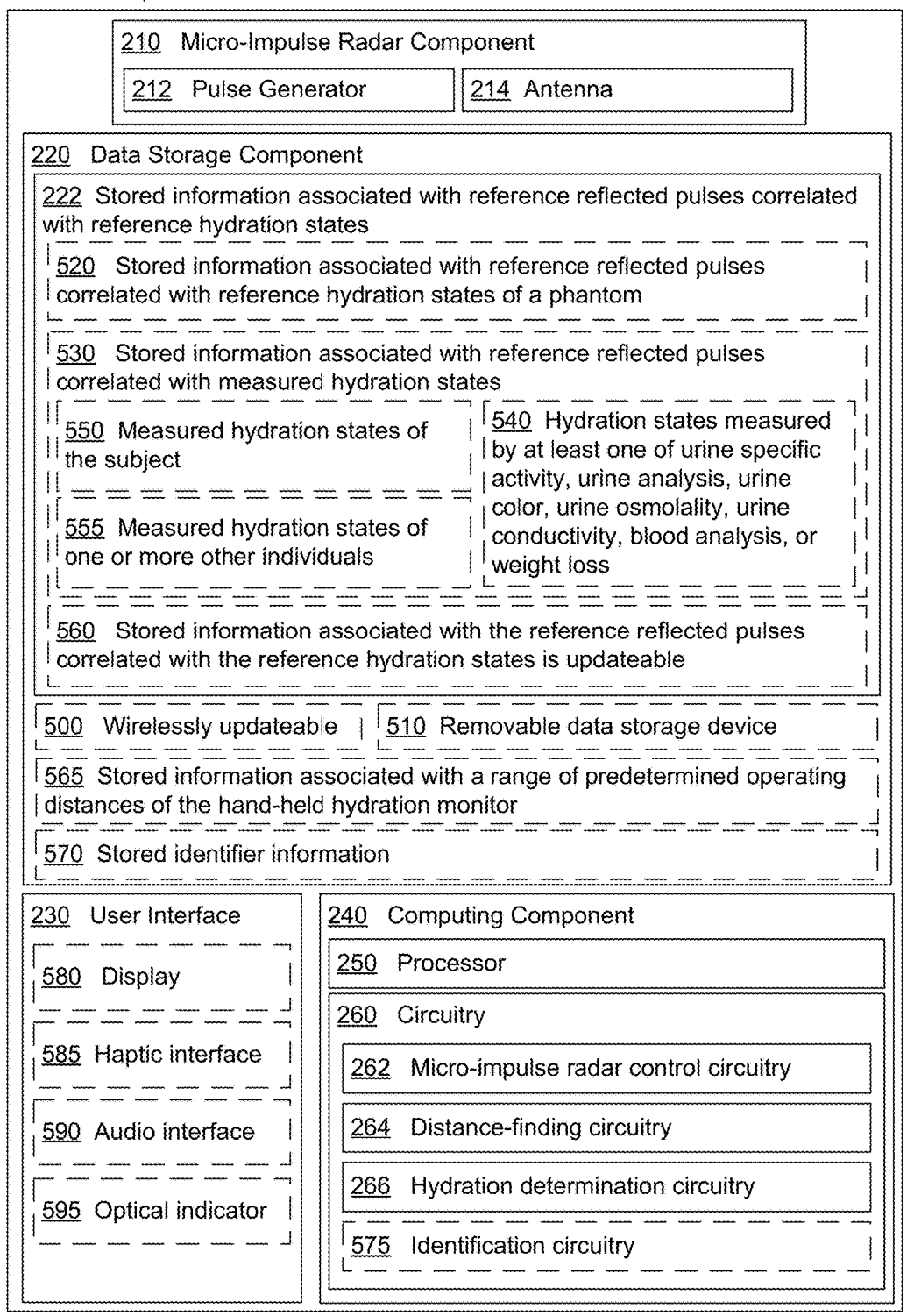
FIG. 5 is a block diagram depicting aspects of a hand-held hydration monitor such as illustrated in FIG. 2.

FIG. 5 illustrates further aspects of a hand-held hydration monitor. Hand-held-hydration monitor 200 includes data storage component 220. Data storage component 220 includes stored information 222 associated with reference reflected pulses correlated with reference hydration states. In an aspect, the data storage component includes a non-volatile data storage component. In an aspect, the data storage component is updatable. In an aspect, the data storage component includes a recordable data storage component. In an aspect, the data storage component includes a mass storage device. In an aspect, the data storage component is operably coupled to a central processing unit of the computing component through input/output channels. In an aspect, the data storage component includes data storage media. In an aspect, the data storage component is included in a hard drive of the computing component. In an aspect, the data storage component is removable. In an aspect, the data storage component includes a removable data storage component. In an aspect, the data storage component includes a removable memory card. In an aspect, the data storage component includes a removable memory stick.

In an aspect, the data storage component is incorporated into the computing component of the hand-held hydration monitor. In an aspect, the data storage component includes memory chips, e.g., ROM or flash memory chips, for providing storage of operating systems, look-up tables, database information regarding reference reflected pulses correlated with reference hydration states for comparing input data, e.g., one or more reflected pulses, with reference data. The system memory of the computing component may include read-only memory (ROM) and random access memory (RAM). A number of program modules may be stored in the ROM or RAM, including an operating system, one or more application programs, other program modules and program data.

Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. By way of example, and not of limitation, computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing component.

In an aspect, the data storage component 220 is wirelessly updateable 500. For example, a data storage component incorporated into the computing component of the device may have access to data wirelessly transmitted to the device, e.g., through a Bluetooth or other wireless transmission means. For example, the data storage component can receive updates to the stored information associated with the reference reflected pulses correlated with the reference hydration states from a wireless transmission from a remote source, e.g., an Internet site, another device, a personal electronic device, and the like.

In an aspect, the data storage component 220 includes a removable data storage device 510. For example, the data storage component can include a removable card, stick, or flash drive. Non-limiting examples of removable data storage devices include flash memory cards, Memory Sticks, mass storage devices, CompactFlash, non-volatile memory cards, Secure Digital™ (SD) cards, miniSD cards, microSD cards, USB flash drive, or XQD cards.

In an aspect, the data storage component 220 includes stored information associated with reference reflected pulses correlated with reference hydration states 222. In an aspect, the reference reflected pulses correlated with the reference hydration states include reference signal patterns associated with reflected pulses and correlated with reference hydration states. In an aspect, the reference reflected pulses include reflected pulses obtained from the target tissue of the subject at a previous point in time. For example, the reference reflected pulses can include historical reflected pulses obtained from the target tissue of the subject. For example, the reference reflected pulses can include reflected pulses obtained from the target tissue of the subject prior to initiating an athletic or strenuous activity session. For example, the reference reflected pulses can include reflected pulses obtained from the target tissue of the subject during and/or after one or more previous athletic or strenuous activity sessions. For example, the reference reflected pulses can include reflected pulses obtained from the target tissue of the subject when the subject is in a specific hydration state, e.g., fully hydrated versus poorly hydrated or very dehydrated. In an aspect, the reference reflected pulses are represented by one or more signal patterns or profiles or an average of signal patterns or profiles. In an aspect, the reference reflected pulses are represented by a signal pattern or profile over a time spectrum. In an aspect, the reference reflected pulses are represented by a signal pattern or profile over a frequency spectrum.

In an aspect, the stored information 222 associated with reference reflected pulses correlated with reference hydration states includes stored information 520 associated with reference reflected pulses correlated with reference hydration states of a phantom. In an aspect, a phantom is used to simulate a tissue in various hydration states. In an aspect, the phantom can include gelatin, agarose gels, silicone, polyacrylamide, or an epoxy resin with varying water content and with permittivity and conductivity properties simulating real tissue. In an aspect, the phantom can include a sponge or other water holding material. In an aspect, the phantom can include a glycerin solution with varying percentage of water. See, e.g., Meaney et al. (2013) "Integration of microwave tomography with magnetic resonance for improved breast imaging," Med. Phys. 40(10):103101; Lazebnick et al. (2005) "Tissue-mimicking phantom material for narrowband and ultrawideband microwave applications," Phys. Med. Biol. 50:4245-4258, which are incorporated herein by reference. In an aspect, the data storage component includes information associated with phantoms of varying water content correlated with signal patterns or profiles generated in response to expose to micro-impulse radar.

In an aspect, the stored information 222 associated with reference reflected pulses correlated with reference hydration states includes stored information 530 associated with reference reflected pulses correlated with measured hydration states. For example, one or more reference reflected pulses can be correlated with a measured parameter of hydration. For example, the signal properties, e.g., frequency, amplitude, and/or time spectrum, of one or more reference reflected pulses can be correlated with at least one measured parameter of hydration. In an aspect, the measured hydration states include hydration states measured by at least one of urine specific gravity, urine analysis, urine color, urine osmolality, urine conductivity, blood analysis, or weight loss, as illustrated in block 540. For example, urine specific gravity (as well as other properties of urine) can be measured using a dipstick (from, e.g., Siemens Medical Solutions USA, Inc., Malvern, Pa.). For example, urine specific gravity can be measured using a pen refractometer (from, e.g., ATAGO U.S.A., Inc., Bellevue, Wash.). Normal urine specific gravity in a human adult ranges from 1.000 to 1.030. Increases in specific gravity can be associated with dehydration and/or excessive sweating. For example, a urine specific gravity greater than 1.035 is consistent with dehydration. For example, urine osmolality can be measured through freezing point osmometry using an osmometer (from, e.g., Advance Instruments, Inc., Norwood, Mass.), in which the freezing point of a solution, i.e., urine, is related to the osmotic concentration of that solution. Normal urine osmolality in a human adult runs from about 50-1400 mOsm. For example, urine color can be assessed using a urine color chart. In an aspect, measured hydration states include hydration states measured by at least one of stable isotope dilution, neutron activation analysis, bioelectrical impedance spectroscopy, and plasma osmolality. In an aspect, measured hydration states include hydration states measured by salivary flow rate, osmolality, and/or protein content. See, e.g., Perrier et al. "Hydration biomarkers in free-living adults with different levels of habitual fluid consumption," (2013) Brit. J. Nutr. 109:1678-1687; Perrier et al. "Relation between urinary hydration biomarkers and total fluid intake in healthy adults," (2013) Eur. J. Clin. Nutr. 67:939-943; and Armstrong "Assessing hydration status:

The elusive gold standard," (2007) J. Am. Coll. Nutr. 26:575S-584S; which are incorporated herein by reference.

In an aspect, the measured hydration states include measured hydration states of the subject 550. For example, the measured hydration states of the subject can include hydration states measured by at least one of urine specific gravity, urine analysis, urine color, urine osmolality, urine conductivity, blood analysis, or weight loss. For example, the measured hydration states of the subject can include hydration states measured by at least one of stable isotope dilution, neutron activation analysis, bioelectrical impedance spectroscopy, plasma osmolality, or saliva analysis. In an aspect, the one or more hydration states are measured when the subject is overly hydrated, normally hydrated, and under hydrated.

In an aspect, the measured hydration states include measured hydration states of one or more other individuals 555. For example, the measured hydration states can include measured hydration states from a normalized population matched to the subject, e.g., matched by age, gender, activity level, medical status, and the like. For example, the measured hydration states of the one or more other individuals can include hydration states measured by at least one of urine specific gravity, urine analysis, urine color, urine osmolality, urine conductivity, blood analysis, or weight loss. For example, the measured hydration states of the one or more other individuals can include hydration states measured by at least one of stable isotope dilution, neutron activation analysis, bioelectrical impedance spectroscopy, plasma osmolality, or saliva analysis. In an aspect, the one or more hydration states are measured when the one or more other individuals is overly hydrated, normally hydrated, and under hydrated.

In an aspect, the stored information associated with the reference reflected pulses correlated with the reference hydration states is updateable, as shown in block 560. The stored information associated with the reference reflected pulses correlated with the reference hydration states can be updated as new information becomes available. For example, the new information can be derived from the subject, e.g., the determined relative hydration state. For example, the new information can be derived from one or more other individuals. In an aspect, the new information is added to the data storage component through a wired communication link. In an aspect, the new information is added to the data storage component through a wireless communication link. In an aspect, the new information is added to the data storage component through a removable data storage device, e.g., a memory card/stick or flash drive.

In an aspect, the data storage component 220 includes stored information 565 associated with a range of predetermined operating distances of the hand-held hydration monitor. For example, the range of predetermined operating distances of the hand-held hydration monitor can include several centimeters to several tens of meters. In an aspect, a maximum operating distance of the hand-held hydration monitor is dependent upon at least one of line of site, a maximum non-ambiguous range (pulse repetition frequency), micro-impulse radar component sensitivity, and/or power of the reflected signal. For example, as the pulse frequency increases, the range decreases. In an aspect, the range of the predetermined operating distances of the hand-held hydration monitor is dependent upon an output power and/or the beam angle of the micro-impulse radar component. For example, the predetermined operating distances can include those distances that provide measurable reflected pulses from the target tissue based on the output power and/or beam angle of the micro-impulse radar component. In an aspect, the range of predetermined operating distances can include a range of distances that will generate the appropriate beam width at the target tissue. For example, a hand-held hydration monitor with a fixed beam angle can include a set of predetermined operating distances that generate a desired beam width at the target tissue.

In an aspect, the data storage component 220 includes stored identifier information 570. In an aspect, stored identifier information includes one or more pieces of identifying information associated with one or more individuals. In an aspect, stored identifier information includes one or more pieces of information that can be used to identify one or more individuals. In an aspect, the stored identifier information includes names, ages, telephone numbers, social security numbers, or identification numbers for one or more individuals. In an aspect, the stored identifier information includes one or more biometric parameters for one or more individuals. Non-limiting examples of biometric parameters include fingerprints, facial recognition, voice recognition, retinal scan, DNA, or other biometric features of a subject. In an aspect, hand-held hydration monitor 200 includes identification circuitry 575 configured to compare at least one subject identifier with the stored identifier information and to generate an identifier comparison. In an aspect, the at last one subject identifier includes personal information specific to the subject, e.g., at least one of a name, age, telephone number, address, or social security number. In an aspect, the at least one subject identifier includes an alphanumeric code, e.g., an identification number or pin number. In an aspect, the at least one subject identifier includes at least one biometric parameter, e.g., fingerprints, facial recognition, voice recognition, retinal scan, DNA, or other biometric feature of the subject. In an aspect, the at least one subject identifier is entered into the hand-held hydration monitor using the user interface. For example, an identification number or code can be entered into a keypad of the hand-held hydration monitor. In an aspect, the at least one subject identifier is entered into the hand-held hydration monitor wirelessly. In an aspect, the at least one subject identifier is measured by the hand-held hydration monitor. For example, the hand-held hydration monitor can include a fingerprint scanner. For example, the hand-held hydration monitor can include an image-capture device and facial recognition software. For example, the hand-held hydration monitor can include a microphone and voice recognition software.

In an aspect, the identifier comparison is reported to the micro-impulse radar control circuitry. In an aspect, the micro-impulse radar control circuitry includes circuitry configured to actuate the micro-impulse radar component in response to the identifier comparison. In an aspect, the micro-impulse radar control circuitry includes circuitry configured to actuate the micro-impulse radar component in response to an identifier comparison that confirms the identity of the subject. For example, the micro-impulse radar control circuitry can be configured to automatically actuate the micro-impulse radar component upon receipt of an identifier comparison that confirms the identity of the subject; i.e., the actual activation may depend upon a separate trigger (e.g., a manual input by the user, range being within predefined limits, etc.), but the trigger only succeeds in activating the micro-impulse radar component as long as the identifier comparison is successful. For example, the micro-impulse radar control circuitry can be configured to prevent actuation of the micro-impulse radar component upon receipt of an identifier comparison that cannot confirm the identity of the subject. In an aspect, the identifier comparison is reported to alert circuitry. In an aspect, the alert circuitry is configured to generate an alert signal in response to the identifier comparison. For example, the alert circuitry can be configured to generate an alert signal that is transmitted to the user interface upon receipt of an identifier comparison that confirms or fails to confirm the identity of the subject.

In an aspect, the data storage component stores subject specific information. For example, the data storage component may be configured to store information associated with the relative hydration state of the subject, at least one subject identifier, a subject hydration/dehydration history, a subject's sensitivity to dehydration, e.g., susceptibility to passing out at a particular hydration state, and subject-specific recovery recommendations. For example, the data storage component may be configured to store information associated with previous distances used to acquire adequate data. For example, the data storage component can include a recommended rehydration protocol for a given subject with a given relative hydration state. For example, the recommended rehydration protocol can include a recommended amount of fluid intake to recover from a dehydrated state based on the subject's previous hydration history.

In an aspect, the data storage component includes operating instructions for the hand-held hydration monitor. In an aspect, the data storage component includes an output power range. In an aspect, the data storage component includes a beam angle range. In an aspect, the data storage component includes a beam width range correlated with operating distance and beam angle. In an aspect, the data storage component includes stored information associated with a range of predetermined operating distances of the hand-held hydration monitor.

The hand-held hydration monitor 200 includes user interface 230. In an aspect, user interface 230 is operably coupled to computing component 240. In an aspect user interface 230 includes one or more input components and/or output components for use by a user to interface with the hand-held hydration monitor. The one or more input components can be used to enter information into the hand-held hydration monitor, e.g., subject identifiers and/or information, operating modes or instructions, measurement parameters, and the like. For example, the one or more operating modes or instructions can include bandwidth, spectral shape, pulse width, pulse format, pulse schedule, polarization, range gate, beam width, beam direction, receiver sensitivity, signal processing parameters, transmitted energy, turning the device on and/or turning the device off. In an aspect, the one or more operating modes and/or instructions includes automatically selecting one or more operating modes and/or instructions as a function of previously received micro-impulse radar data.

In an aspect, the user interface is integrated into the hand-held hydration monitor or optionally may be one or more peripheral devices operably connected through a wired or wireless connection to the hand-held hydration monitor. Non-limiting examples of input components include a graphical user interface, a display, a keyboard, a keypad, a touch-screen, a microphone, a stylus pen, a switch, a dial, a button, or the like. In some embodiments, existing input component on a peripheral device (e.g., a smartphone, tablet, laptop computer, and the like) can be used to control the hand-held hydration monitor via a wired or wireless connection. Other non-limiting examples of input components include a trackball, a joystick, a mouse, an image scanner, a digital camera, a webcam, a light pen, a bar code reader, a fingerprint scanner, a retinal scanner, or a game pad. In some embodiments, the user interface is user driven. For example, the user inputs data or operating conditions into the hand-held hydration monitor using the user interface, e.g., a touch-screen. In an aspect, the user interface includes one or more buttons or switches. For example, the user interface can include an on/off button or switch. For example, the user interface can include an actuation button or switch. In some embodiments, the user interface, e.g., a switch, is circuitry driven. For example, an on/off switch may be toggled based on proximity of the hand-held hydration monitor to a target subject.

In an aspect, user interface 230 includes one or more output components over which processed information is transmitted, e.g., viewed, as output results and may be integrated into the hand-held hydration monitor or may be one or more peripheral devices operably connected through a wired or wireless connection to the hand-held hydration monitor. For example, the user interface may be used to report to a user a relative hydration state of the tissue associated with target or target location on a subject. Non-limiting examples of output components include but are not limited to displays, e.g., liquid crystal displays, audio speakers, and the like.

In an aspect, user interface 230 includes display 580. For example, the display can include a light-emitting diode (LED) display. For example, the display can include a liquid crystal display (LCD). In an aspect, the display is operably coupled to a keypad or touchpad. In an aspect, the display can include a touchscreen display with an integrated keypad. For example, the display can include a touchscreen of the type used in personal electronic devices, e.g., cell phones or tablet computers. In an aspect, the display can include any of a number of display types commonly used in handheld devices.

In an aspect, user interface 230 includes haptic interface 585. In an aspect, the haptic interface includes tactile feedback technology. In an aspect, the haptic interface provides at least one of a force, a vibration, or a motion to the user. For example, the haptic interface can include a vibratory motor, e.g., a rumble pack. For example, the haptic interface can include a haptic actuator, e.g., electroactive polymers, or piezoelectric, electrostatic, or subsonic audio wave surface actuators.

In an aspect, user interface 230 includes audio interface 590. In an aspect, the audio interface includes at least one microphone, at least one speaker, and sound functionality integrated into the computing component of the device. In an aspect, the audio interface includes a sound card. In an aspect, the audio interface includes an audio digital signal processor (DSP).

In an aspect, user interface 230 includes at least one optical indicator 595. For example, the at least one optical indicator can include a single light which when on and/or off is indicative of an alert message. For example, the at least one optical indicator can include a warning light, e.g., a red light, or a go light, e.g., a green light, to indicate whether or not the current measurement parameters, e.g., the determined distance, has been satisfied for capturing useful data. For example, the at least one optical indicator can include at least one light-emitting diode.

Hand-held hydration monitor 200 includes computing component 240. Computing component 240 includes a processor 250, e.g., a microprocessor, and circuitry 260. Computing component 240 includes micro-impulse radar control circuitry 262 configured to actuate the micro-impulse radar component; distance-finding circuitry 264 configured to determine a distance between the hand-held hydration monitor and a target location on a subject; and hydration determination circuitry 266 configured to receive information associated with one or more reflected pulses from a target tissue associated with the target location on the subject and to compare the information associated with the reflected one or more pulses from the target tissue with the stored information associated with the reference reflected pulses correlated with the reference hydration states to determine a relative hydration state of the target tissue.

In an aspect, the computing component includes circuitry to execute one or more instructions for running the micro-impulse radar component, the data storage component, and the user interface. In an aspect, the computing component includes circuitry to execute one or more instructions for operating any or all other components incorporated into the hand-held hydration monitor, e.g., a projector component, an image-capture device, a transmission unit, or other components of the device. In an aspect, the computing component includes circuitry to execute one or more instructions for actuating the micro-impulse radar component; one or more instructions for determining a distance between the hand-held hydration monitor and a target location on a subject; one or more instructions for receiving information associated with one or more reflected pulses from a target tissue associated with the target location on the subject; and one or more instructions for comparing the information associated with the one or more reflected pulses from the target tissue with the stored information associated with the reference reflected pulses correlated with the reference hydration states to determine a relative hydration state of the target tissue.

In an aspect, the computing component includes a microprocessor, e.g., a central processing unit, for controlling one or more functions of the hand-held hydration monitor. The computing component further includes a system memory and a system bus that couples various system components including the system memory to the microprocessor. The microprocessor can include a processing unit, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the computing component includes one or more ASICs having a plurality of pre-defined logic components. In an aspect, the computing component includes one or more FPGA having a plurality of programmable logic commands.

In an aspect, image-based applications such as viewers and/or toolkits (e.g., Insight Segmentation and Registration Toolkit (ITK)), are incorporated for further intake of information. In an aspect, CAD implementations, image segmentation, or other image analysis algorithms may allow processing of images received from an image-capture device.

The computing component can further include memory chips, e.g., ROM or flash memory chips, for providing storage of operating systems, look-up tables, database information (e.g., stored information associated with reference reflected pulses correlated with reference hydration states, stored location information, and/or stored identifier information) and algorithms for comparing input data with reference data. The system memory of the computing component may include read-only memory (ROM) and random access memory (RAM). A number of program modules may be stored in the ROM or RAM, including an operating system, one or more application programs, other program modules and program data.

The computing component may further include or be capable of connecting to a flash card memory. For example, the computing device may be capable of connecting to a data storage component that is a flash card memory. The computing component may further include or be capable of connecting with a network through a network port and network interface, and through wireless port and corresponding wireless interface may be provided to facilitate communication with other peripheral devices, for example, a smart phone, a computer, a display monitor, and/or a printer.

The computing component includes computer-readable media products and may include any media that can be accessed by the computing component including both volatile and nonvolatile media, removable and non-removable media. By way of example, and not of limitation, computer-readable media may include non-transitory signal-bearing media. Non-limiting examples of non-transitory signal-bearing media include a recordable type medium such as magnetic tape, a hard disk drive, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. By way of example, and not of limitation, computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing component. By way of further example, and not of limitation, computer-readable media may include a communication media, e.g., wired media, such as a wired network and a direct-wired connection, and wireless media such as acoustic, RF, optical, and infrared media.

Figure 6:
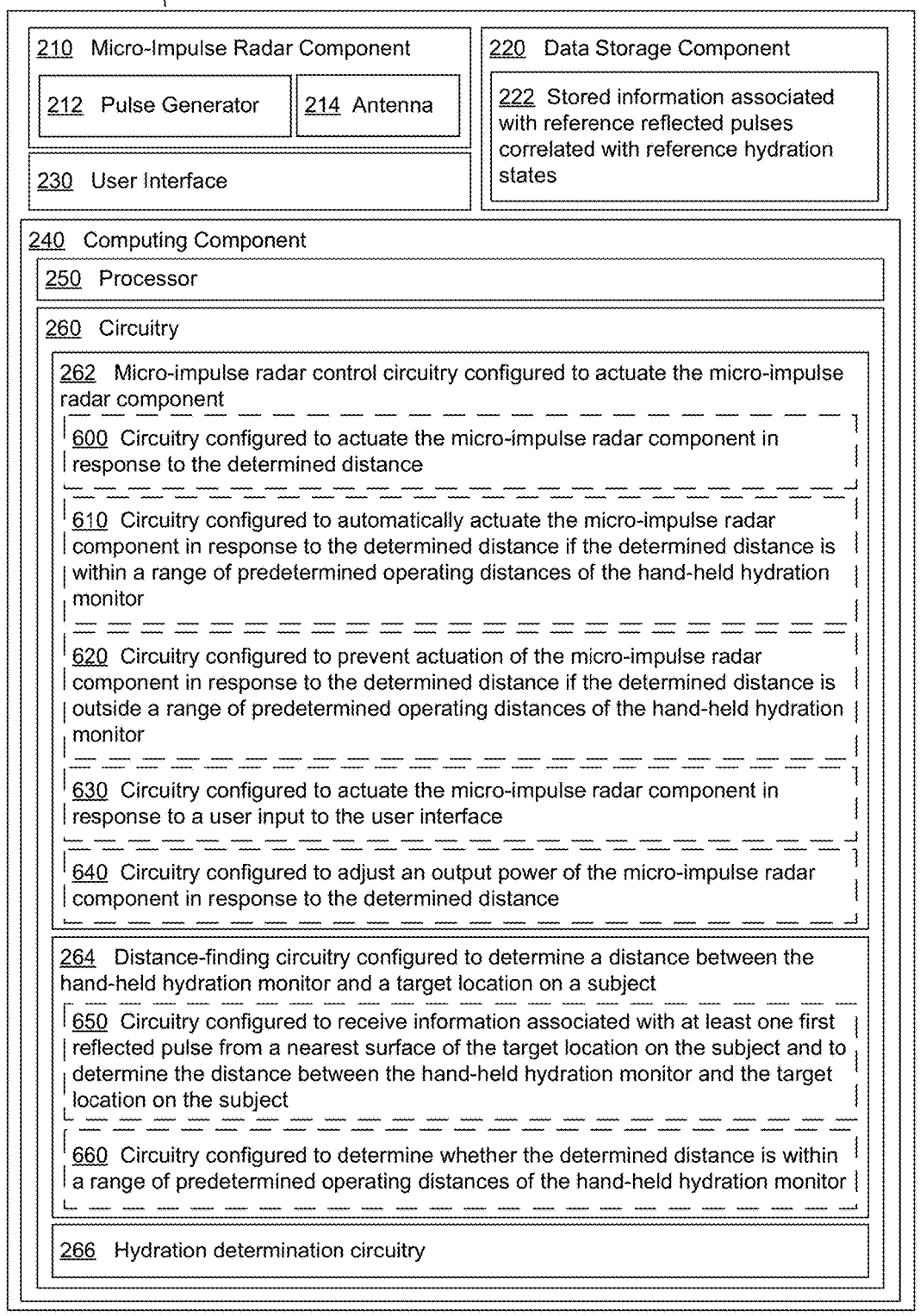
FIG. 6 is a block diagram illustrating aspects of a hand-held hydration monitor such as shown in FIG. 2.

FIG. 6 illustrates further aspects of hand-held hydration monitor. In an aspect, computing component 240 of hand-held hydration monitor 200 includes micro-impulse radar control circuitry 262. Micro-impulse radar control circuitry 262 is configured to actuate micro-impulse radar component 210. In an aspect, the micro-impulse radar control circuitry includes circuitry configured to turn on or off the micro-impulse radar component. In an aspect, the micro-impulse radar control circuitry includes circuitry configured to control operation of the micro-impulse radar component. In an aspect, the micro-impulse radar control circuitry includes circuitry configured to control operation of one or more components of the micro-impulse radar component. For example, the micro-impulse radar control circuitry can include circuitry configured to control the pulse generator. For example, the micro-impulse radar control circuitry can include circuitry configured to control the at least one antenna. For example, the micro-impulse radar control circuitry can include circuitry configured to control the receiver. For example, the micro-impulse radar control circuitry can include circuitry configured to control the adjustable range gate. In an aspect, the micro-impulse radar control circuitry includes circuitry configured to control one or more operational parameters of the micro-impulse radar component. In an aspect, the one or more operational parameters includes output power, bandwidth, spectral shape, pulse width, pulse format, pulse schedule, polarization, range, gate, beam width, beam direction, receiver sensitivity, signal processing parameters, and transmitted energy.

The hand-held hydration monitor further includes distance-finding circuitry 264 configured to determine a distance between the hand-held hydration monitor and a target location on a subject. In an aspect, the distance-finding circuitry includes circuitry 650 configured to receive information associated with at least one first reflected pulse from a nearest surface of the target location on the subject and to determine the distance between the hand-held hydration monitor and the target location on the subject. In an aspect, the first reflected pulse is used as a range finder to determine the distance between the hand-held hydration monitor and the subject. In an aspect, the distance-finding circuitry includes circuitry configured to determine a target range. For example, the distance-finding circuitry can include circuitry to calculate the round trip travel time of a transmitted pulse. For example, the distance (R) can be calculated from the round trip travel time ($T_R$) using the following equation:

$$R = \frac{cT_R}{2}$$

where c is the velocity of light in free space ($3 \times 10^8$ m/s). In an aspect, the transmitted pulse is emitted from the micro-impulse radar component. In an aspect, the transmitted pulse is emitted from a rangefinder, e.g., a laser rangefinder, associated with the hand-held hydration monitor. In an aspect, the transmitted pulse is emitted from an ultrasonic source, e.g., an ultrasonic rangefinder, associated with the hand-held hydration monitor; in this respect "c" in the above relation represents the speed of sound in air.

In an aspect, the distance-finding circuitry 264 includes circuitry 660 configured to determine whether the determined distance is within a range of predetermined operating distances of the hand-held hydration monitor. For example, the range of predetermined operating distances of the hand-held hydration monitor can include several centimeters to several tens of meters. In an aspect, a maximum operating distance of the hand-held hydration monitor is dependent upon line of site, a maximum non-ambiguous range (pulse repetition frequency), and micro-impulse radar component sensitivity and power of the reflected signal. For example, as the pulse frequency increases, the range decreases. In an aspect, the range of the predetermined operating distances of the hand-held hydration monitor is dependent upon an output power and/or the beam angle of the micro-impulse radar component. For example, the predetermined operating distances can include those distances that provide measurable reflected pulses from the target tissue based on the output power and/or beam angle of the micro-impulse radar component. In an aspect, the range of predetermined operating distances can include a range of distances that will generate the appropriate beam width at the target tissue. For example, a hand-held hydration monitor with a fixed beam angle can include a set of predetermined operating distances that generate a desired beam width at the target tissue. In an aspect, information associated with the range of predetermined operating distances of the hand-held hydration monitor is stored in the data storage component of the hand-held hydration monitor.

In an aspect, micro-impulse radar control circuitry 262 includes circuitry 600 configured to actuate the micro-impulse radar component in response to the determined distance. In an aspect, micro-impulse radar control circuitry 262 includes circuitry 610 configured to automatically actuate the micro-impulse radar component in response to the determined distance if the determined distance is within a range of predetermined operating distances of the hand-held hydration monitor. For example, the micro-impulse radar component can be automatically actuated when the hand-held hydration monitor is at an appropriate operating distance from the subject.

In an aspect, micro-impulse radar control circuitry 262 includes circuitry 620 configured to prevent actuation of the micro-impulse radar component in response to the determined distance if the determined distance is outside a range of predetermined operating distances of the hand-held hydration monitor. For example, the micro-impulse radar control circuitry can include a locking feature or mechanism that prevents automatic and/or manual actuation of the micro-impulse radar component if the hand-held hydration monitor or the subject is not at an appropriate operating distance.

In an aspect, micro-impulse radar control circuitry 262 includes circuitry 630 configured to actuate the micro-impulse radar component in response to a user input to the user interface. For example, the hand-held hydration monitor can include an actuation button which when pushed by the user actuates the micro-impulse radar control circuitry. For example, the user can push an actuation button on the hand-held hydration monitor in response to receiving an alert message, e.g., a green light, indicating that the determined distance between the hand-held hydration monitor and the subject is within a range of predetermined operating distances of the hand-held hydration monitor. In some embodiments, actuation of the micro-impulse radar component by pushing of an actuation button can be conditional upon an authorization condition being met. For example, the button push may be effective only if the range is within a predetermined distance and/or the identifier comparison is successful.

In an aspect, micro-impulse radar control circuitry 262 includes circuitry 640 configured to adjust an output power of the micro-impulse radar component in response to the determined distance. For example, the micro-impulse radar component is configured to transmit ultra wideband pulses of sufficient energy so that the reflected pulses are detectable by the receiver. In an aspect, the amount of energy delivered to the target location on the subject is inversely proportional to the square of the determined distance between the hand-held hydration monitor (i.e., the energy transmitter) and the target location on the subject. For example, the intensity of the ultra-wideband pulses radiating from the micro-impulse radar component (power per unit area perpendicular to the source) at the target location on the subject is inversely proportional to the square of the distance between the hand-held hydration monitor and the target location on the subject. In an aspect, to insure that a specific amount of energy reaches the target location on the subject, the amount of energy transmitted by the energy transmitter is controller to vary proportional to the square of the determined distance between the hand-held hydration monitor (i.e., the energy transmitter) and the target location on the subject. In an aspect, the amount of energy scattered from the target location on the subject to the receiving antenna on the hand-held hydration monitor is inversely proportional to the square of the determined distance between the hand-held hydration monitor and the target location on the subject. In an aspect, the beam width at the target location of the subject is less than a specified target size, such that the amount of energy illuminating the target region does not significantly depend on the determined distance; accordingly, the amount of energy transmitted by the energy transmitter is controlled to vary proportional to the square of the determined distance between the hand-held hydration monitor (i.e., the energy transmitter) and the target location on the subject so as to offset the spread of the returning scatter energy and maintain a specified energy at the receiving antenna. In another aspect, the beam width at the target location of the subject is greater than a specified target size, such that the amount of energy illuminating the target region fall off with the inverse square of the determined distance; accordingly, the amount of energy transmitted by the energy transmitter is controlled to vary proportional to the fourth power of the determined distance between the hand-held hydration monitor (i.e., the energy transmitter) and the target location on the subject so as to maintain a specified energy at the receiving antenna. In an aspect, the amount of energy delivered to a target at a specific distance is dependent upon the output power of the transmitter and the duration of the transmission. In an aspect, the output power is adjusted upward as the distance between the hand-held hydration monitor and the target location on the subject increases. In an aspect, the output power is adjusted downward as the distance between the hand-held hydration monitor and the target location on the subject decreases.

Figure 7:
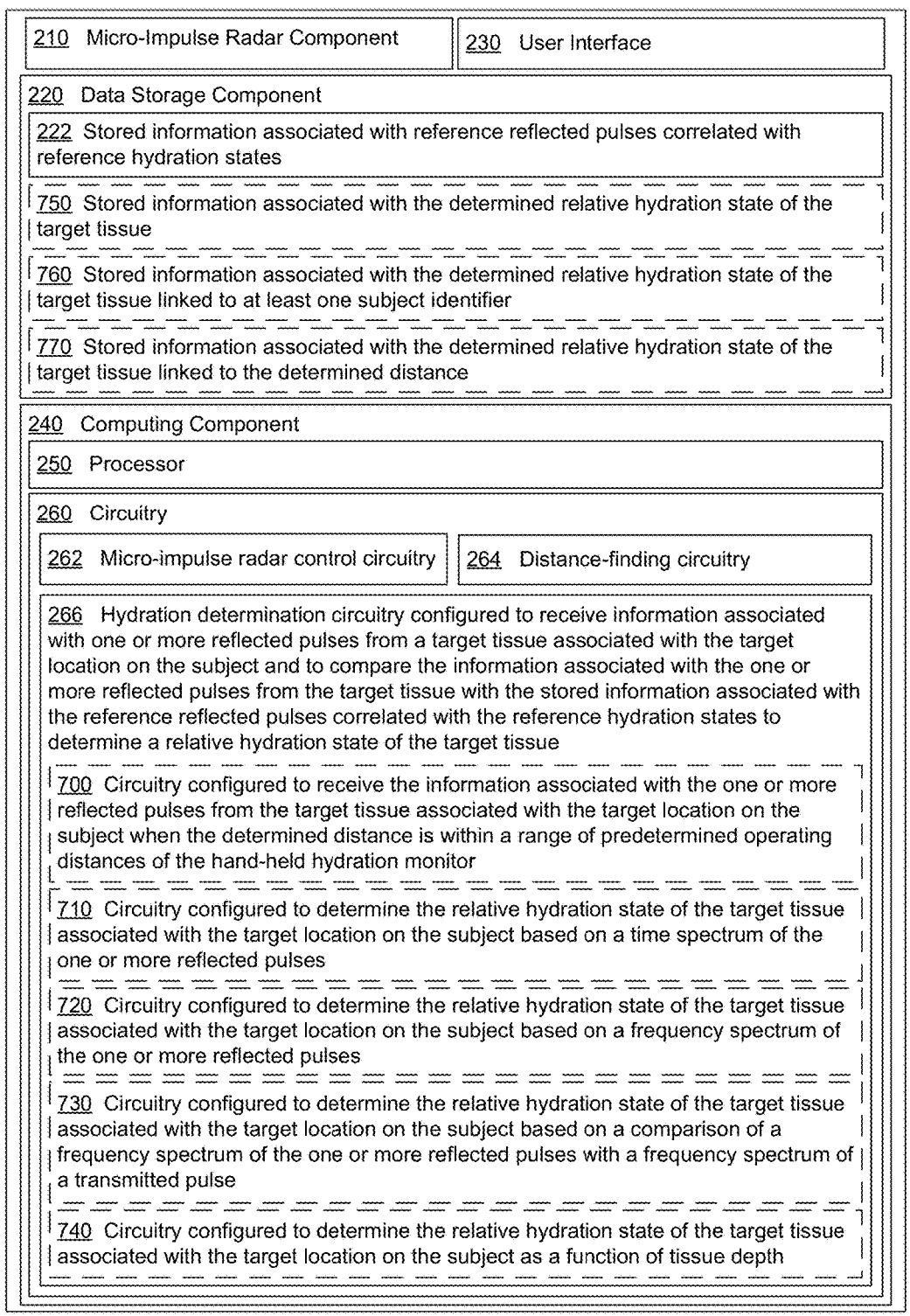
FIG. 7 is a block diagram showing aspects of a hand-held hydration monitor such as depicted in FIG. 2.

FIG. 7 illustrates further aspects of a hand-held hydration monitor. Hand-held hydration monitor 200 includes hydration determination circuitry 266 configured to receive information associated with one or more reflected pulses from a target tissue associated with the target location on the subject and to compare the information associated with the one or more reflected pulses from the target tissue with the stored information associated with the reference reflected pulses correlated with the reference hydration states to determine a relative hydration state of the target tissue. In an aspect, the hydration determination circuitry 266 receives processed signals from a signal processor of the micro-impulse radar component, the processed signals including the information associated with the one or more reflected pulses. In an aspect, the hydration determination circuitry 266 compares one or more signal profiles representative of the one or more reflected pulses with the stored information associated with the reference reflected pulses correlated with the reference hydration states. For example, the hydration determination circuitry can compare one or more signal profiles representative of the one or more reflected pulses from the target tissue with reference signal profiles correlated with reference hydration states.

In an aspect, hydration determination circuitry 266 includes circuitry 700 configured to receive the information associated with the one or more reflected pulses from the target tissue associated with the target location on the subject when the determined distance is within a range of predetermined operating distances of the hand-held hydration monitor. For example, the hydration determination circuitry can be configured to receive information associated with the one or more reflected pulses only if the measurements were taken at an appropriate operating distance.

In an aspect, hydration determination circuitry 266 includes circuitry configured to compare the information associated with the one or more reflected pulses from the target tissue with the stored information associated with the reference reflected pulses correlated with reference hydration states based on scaling to a reference distance.

In an aspect, hydration determination circuitry 266 includes circuitry 710 configured to determine the relative hydration state of the target tissue associated with the target location on the subject based on a time spectrum of the one or more reflected pulses. For example, the relative hydration state of the target tissue can be determined based on comparing received signals from the one or more reflected pulses at specific time points relative to the stored reference information. For example, a signal peak at a particular time point on the time spectrum may change or shift (e.g., in amplitude or time) depending upon the hydration state.

In an aspect, hydration determination circuitry 266 includes circuitry 720 configured to determine the relative hydration state of the target tissue associated with the target location on the subject based on a frequency spectrum of the one or more reflected pulses. For example, the behavior of electromagnetic waves is dependent on the physical dimensions and dielectric properties of the tissue. In turn, the dielectric properties of the tissue are frequency dependent. See, e.g., O'Halloran et al. (2006) "Frequency-Dependent Modeling of Ultra-WideBand Pulses in Human Tissue for Biomedical Applications," ISSC 2006, Dublin Institute of Technology, June 28-30, which is incorporated herein by reference. For example, the relative hydration state of the target tissue can be determined based on comparing received signals from the one or more reflected pulses at specific frequencies or frequency bands relative to the stored reference information. For example, a signal peak at a particular frequency or frequency band on the frequency spectrum may change or shift (e.g., in amplitude or frequency) depending upon the hydration state.

In an aspect, hydration determination circuitry 266 includes circuitry 730 configured to determine the relative hydration state of the target tissue associated with the target location on the subject based on a comparison of a frequency spectrum of the one or more reflected pulses with a frequency spectrum of a transmitted pulse. For example, the relative hydration state can be determined by correlating changes in the frequency spectrum transmitted versus the frequency spectrum received under different hydration conditions of the tissue.

In an aspect, the one or more reflected pulses from the target tissue associated with the target location on the subject include percentage of a transmitted pulse. For example, only a percentage of the energy transmitted to the target tissue is reflected and detected by the at least one antenna of the micro-impulse radar component. In an aspect, the percentage of the transmitted pulse is dependent upon the determined distance and a water content of the target tissue. For example, the percentage of the transmitted pulse reflected back from the target tissue is dependent upon how far away the target tissue is from the hand-held hydration monitor and/or the water content of the target tissue. In an aspect, the percentage of the transmitted pulse reflected back from the target tissue is reflected in the frequency spectrum of the one or more reflected pulses and/or the time spectrum of the one or more reflected pulses.

In an aspect, hydration determination circuitry 266 includes circuitry 740 configured to determine the relative hydration state of the target tissue associated with the target location on the subject as a function of tissue depth. For example, the range gate can be adjusted to collect reflected pulses at specific time points after transmission of a pulse relative to the depth of tissue being measured. In general, a transmitted pulse electromagnetic energy travels at the speed of light through air, but slows down upon entering the body. See, e.g., Pancera (2010) IEEE 2010 Loughborough Antennas & Propagation Conference, 8-9 Nov. 2010, Loughborough, UK, which is incorporated herein by reference. The reduction in speed is dependent upon the depth as well as the tissue type. For example, the speed through muscle is about seven times slower than through air. As a transmitted pulse penetrates a tissue, the magnitude of the pulse is attenuated exponentially. The amount of attenuation the signal suffers as it travels through the tissue depends on the dielectric properties of the tissue. For example, the relative hydration state can be determined by correlating changes in the reflected pulses from specific tissue depths versus hydration conditions of the tissue.

In an aspect, data storage component 220 is configured to stored information associated with the determined relative hydration state of the tissue. In an aspect, data storage component 220 includes stored information 750 associated with the determined relative hydration state of the target tissue. In an aspect, data storage component 220 includes stored information 760 associated with the determined relative hydration state of the target tissue linked to at least one subject identifier. For example, the determined relative hydration state of the target tissue of the subject can be linked to the subject's name, identification number, or biometric property. In an aspect, data storage component 220 includes stored information 770 associated with the determined relative hydration state of the target tissue linked to the determined distance. For example, the data storage component can include stored information associated with hydration states of a target tissue measured with the hand-held hydration monitor at different distances from the subject.

Figure 8:
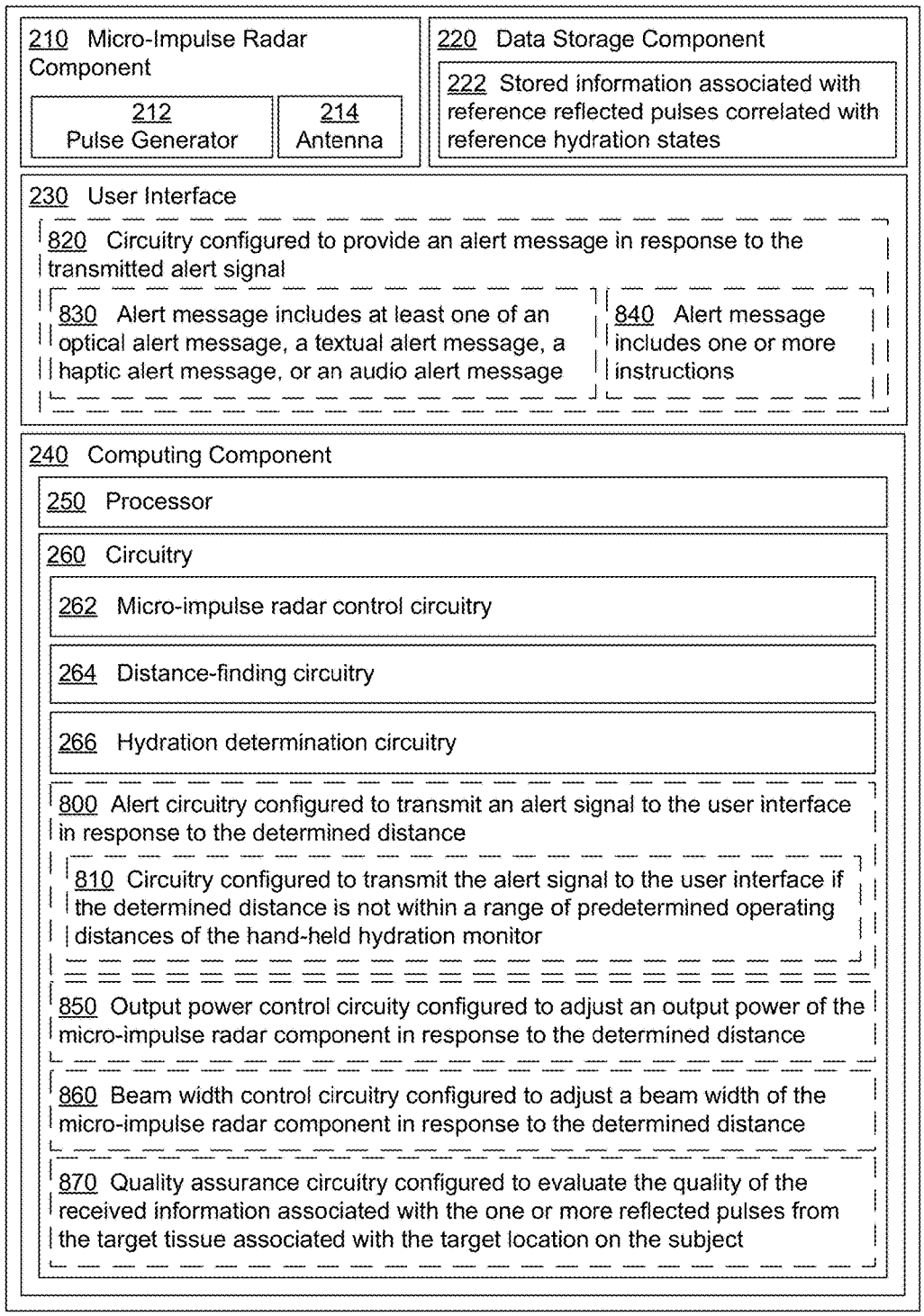
FIG. 8 is a block diagram depicting aspects of a hand-held hydration monitor such as illustrated in FIG. 2.

FIG. 8 illustrates further aspects of a hand-held hydration monitor. Hand-held hydration monitor 200 can include alert circuitry 800 configured to transmit an alert signal to the user interface in response to the determined distance. In some embodiments, alert circuitry 800 includes circuitry 810 configured to transmit the alert signal to the user interface 230 if the determined distance is not within a range of predetermined operating distances of the hand-held hydration monitor 200. In an aspect, user interface 230 includes circuitry 820 configured to provide an alert message in response to the transmitted alert signal. In an aspect, the alert message includes at least one of an optical alert message, a textual alert message, a haptic alert message, or an audio alert message, as shown in block 830. For example, the alert circuitry can transmit an alert signal to the user interface if the subject is positioned too far away from the hand-held hydration monitor to acquire an accurate reading. For example, the user interface can provide an optical alert message, e.g., a red flashing light, in response to the alert signal. For example, the user interface can provide a textual alert message, e.g., "subject is out of range," in response to the alert signal. For example, the user interface can provide a haptic alert message, e.g., vibration of at least a portion of the hand-held hydration monitor, in response to the alert signal. For example, the user interface can provide an audio alert message, e.g., "subject is out of range," in response to the alert signal.

In an aspect, the alert message includes one or more instructions 840. In an aspect, the alert message includes one or more textual or audio instructions. For example, the alert message can include one or more textual or audio instructions for a user. For example, the alert message can include one or more textual or audio instructions instructing the user to move at least one of right, left, back, or forward to adjust the distance between the hand-held hydration monitor and the subject. For example, the alert message can include one or more textual or audio instructions instructing the user to push an actuation button to initiate actuation of the micro-impulse radar component. In an aspect, the alert message can include one or more instructions for adjusting a component of the hand-held hydration monitor. For example, the alert message can include one or more instructions for adjusting an output power, a beam width, a pulse frequency, or other aspects of the hand-held hydration monitor.

In an aspect, the alert message includes one or more instructions for treating dehydration. For example, the one or more instructions can include instructions for sipping small amounts of water, drinking carbohydrate/electrolyte containing drinks (e.g., Gatorade or Pedialyte®), sucking popsicles made from juices or sports drinks, sucking ice chips. In some instances, if the dehydration symptoms are particularly severe, e.g., elevated resting heart rate and low blood pressure, the one or more instructions can include recommending administration of intravenous fluids. For example, the one or more instructions can include instructions to cool the subject if the dehydration is due to excessive heat exposure or elevated body temperature. For example, the one or more instructions can include instructions to remove excess clothing and/or to loosen clothing. For example, the one or more instructions can include instructions to move to an air conditioned area or to move in proximity to a fan or into the shade. For example, the one or more instructions can include instructions to use a spray bottle or mister to spray lukewarm water on exposed skin surfaces to help with cooling by evaporation.

In some embodiments, alert circuitry 800 includes circuitry configured to transmit an alert signal to the user interface 230 if the determined distance is within range of predetermined operating distances of the hand-held hydration monitor 200. In an aspect, the user interface 230 is configured to provide an alert message in response to the transmitted alert signal indicating that the determined distance is within a range of the predetermined operating distances of the hand-held hydration monitor. In an aspect, the alert message instructs a user to manually actuate the micro-impulse radar component. For example, the user interface can include an optical alert message, e.g., a green light, instructing a user to manually actuate the micro-impulse radar component. For example, the user interface can include a textual alert message, e.g., "actuate now," instructing a user to manually actuate the micro-impulse radar component. For example, the user interface can include a haptic alert message, e.g., a vibration, instructing a user to manually actuate the micro-impulse radar component. For example, the user interface can include an audio alert message, e.g., "actuate now," instructing a user to manually actuate the micro-impulse radar component. In an aspect, the user manually actuates the micro-impulse radar component by interacting with the user interface of the hand-held hydration monitor. In an aspect, the micro-impulse radar control circuitry includes circuitry configured to actuate the micro-impulse radar component in response to a user input, e.g., user input through the user interface.

In an aspect, circuitry 260 of computing component 240 includes output power control circuitry 850 configured to adjust an output power of the micro-impulse radar component in response to the determined distance. In an aspect, output power control circuitry 850 is configured to determine an output power from the micro-impulse radar component and to determine an appropriate range of operating distances based on the determined output power. In an aspect, the output power control circuitry controls the output power from the micro-impulse radar component. For example, output power control circuitry can be configured to determine an appropriate output power of the transmitted electromagnetic pulses to ensure that the received reflected pulses have sufficient energy to be measured.

In an aspect, circuitry 260 of computing component 240 includes beam width control circuitry 860 configured to adjust a beam width of the micro-impulse radar component in response to the determined distance. In an aspect, computing component 240 includes circuitry configured to adjust a beam angle of the micro-impulse radar component in response to the determined distance. For example, the beam width control circuitry can be configured to calculate an appropriate beam width to just cover a region of target tissue and to adjust the beam angle based on the distance between the hand-held hydration monitor and the subject to achieve the calculated beam width. In an aspect, the beam width control circuitry is operably coupled to image processing circuitry; the image processing circuitry configured to recognize the outline of a subject, the beam width control circuitry configured to adjust the beam angle and an aim point to just cover a portion of the subject prior to initiating a scan.

In an aspect, circuitry 260 of computing component 240 includes quality assurance circuitry 870 configured to evaluate the quality of the received information associated with the one or more reflected pulses from the target tissue associated with the target location on the subject. In an aspect, the quality assurance circuitry includes circuitry configured to evaluate the quality of the received information associated with the one or more reflected pulses from the target tissue of the subject against a quality threshold. In an aspect, the quality threshold can include a signal-to-noise threshold. For example, the quality assurance circuitry can include circuitry configured to determine whether a return signal generated by the one or more reflected pulses is adequate, e.g., above a signal-to-noise threshold. In an aspect, the quality threshold can include a "reasonability" threshold. For example, is the received information associated with the one or more reflected pulses reasonable (e.g., in terms of amplitude, frequency, and the like), for the measuring conditions. If the quality threshold indicates that the received information associated with the one or more reflected pulses is good, then the comparison of the received information with the stored information can proceed. If the quality threshold indicates that the received information associated with the one or more reflected pulses is bad, then additional information is required. In an aspect, the micro-impulse radar control circuitry includes circuitry configured to actuate the micro-impulse radar component to transmit one or more additional pulses to the target tissue of the subject if the evaluated quality of the received one or more reflected pulses fails to meet or exceed the quality threshold.

Figure 9:
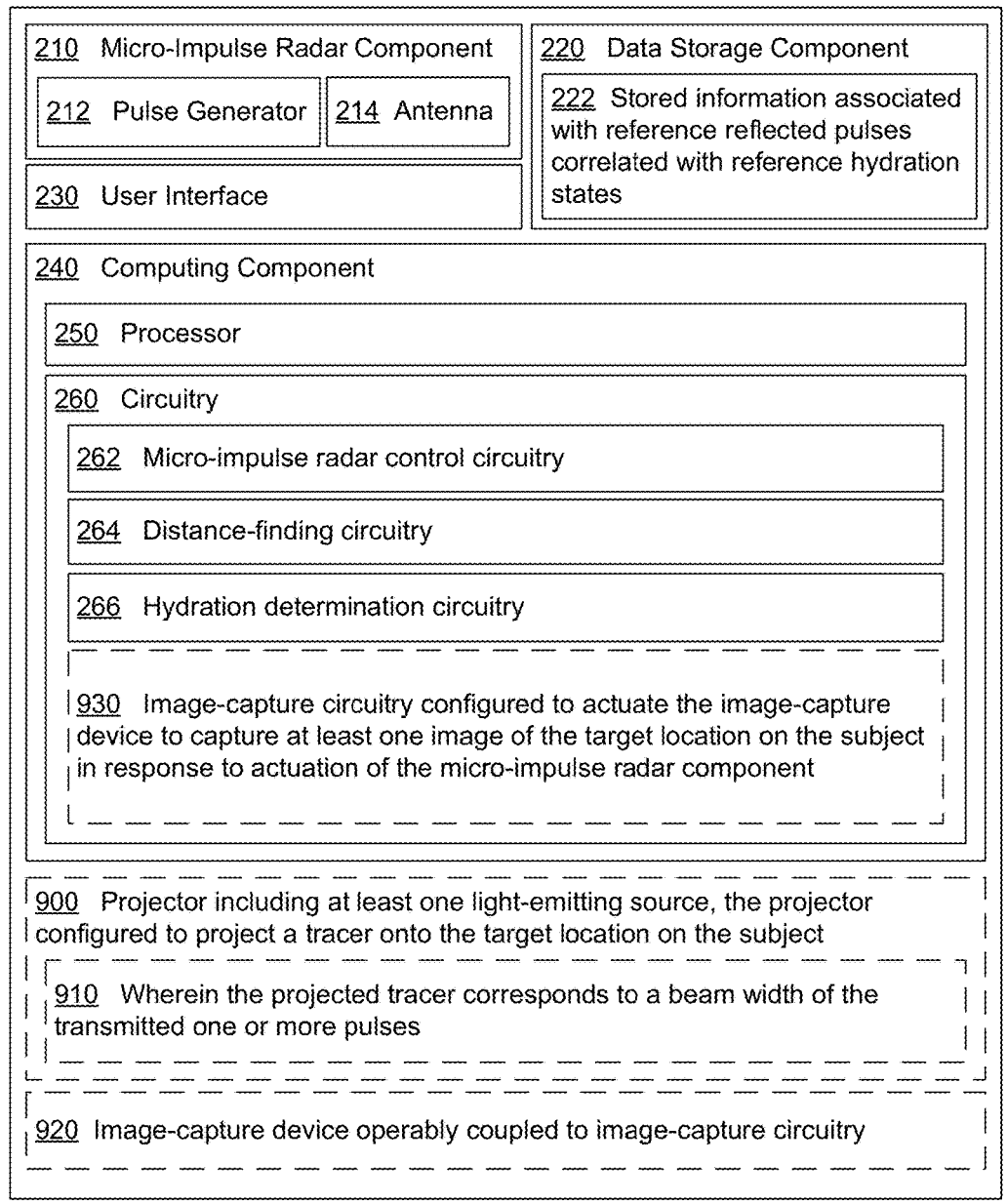
FIG. 9 is a block diagram illustrating aspects of a hand-held hydration monitor such as shown in FIG. 2.

FIG. 9 illustrates further aspects of a hand-held hydration monitor. In an aspect, hand-held hydration monitor 200 includes projector 900 including at least one light-emitting source, the projector configured to project a tracer onto the target location on the subject. In an aspect, the tracer projected onto the subject indicates where the transmitted one or more pulses will converge with the subject. In an aspect, the tracer is a center point of the transmitted one or more pulses. In an aspect, the tracer is positioned on a central point of the intended target location on the subject. In an aspect, the tracer includes at least one of a dot, a circle, a ring, a border, lines, or concentric rings.

In an aspect, the projector includes one or more light-emitting sources configured to emit non-destructive light, e.g., light of a wavelength, intensity, and/or energy that is non-destructive and/or non-damaging to cells and/or tissue of a body region, including the eyes.

In an aspect, the at least one light-emitting source includes a laser. In an aspect, the laser radiation emitted from the at least one light-emitting source is categorized as class I, II, or IIIa as per the United States Food and Drug Administration (FDA) (see, e.g., 21CFR1040.10, *Code of Federal Regulations*, Title 21, Volume 8, Chapter 1, Subchapter J, Radiological Health, which is incorporated herein by reference). Class I levels of laser radiation are considered non-hazardous, although hazard increases with optical aids, including magnifiers, binoculars, or telescopes; class IIa levels of laser radiation are considered non-hazardous if viewed for any period of time less than or equal to 1000 seconds but are considered to be a chronic viewing hazard for any period of time greater than 1000 seconds; class II levels of laser radiation are considered to be a chronic viewing hazard; and class Ma levels of laser radiation are considered to be, depending upon the irradiance, either an acute intrabeam viewing hazard or chronic viewing hazard, and an acute viewing hazard if viewed directly with optical instruments.

In an aspect, the at least one light-emitting source includes at least one of a light-emitting diode, a laser, a laser diode, a collimated light source, or a focused light source. In an aspect, the at least one light-emitting source includes at least one light-emitting diode (LED), semiconductor light sources available in a variety of colors and sizes. In an aspect, the at least one light-emitting source includes a laser, non-limiting examples of which include solid-state lasers (e.g., neodymium-Yag laser), gas lasers (e.g., helium lasers), excimer lasers (e.g., chlorine or fluorine mixed with inert gases), and dye lasers (e.g., rhodamine 6G lasers). In an aspect, the at least one light-emitting source includes one or more laser diodes. In an aspect, the at least one light-emitting source includes one or more collimated light sources. For example, light from a laser diode or LED may be collimated by passing the light through one or more collimating lens to achieve a narrower band of emitted light. For example, a divergent beam of light emitted from an LED can be collimated with one or more lens and/or curved mirrors. In an aspect, the at least one light-emitting source includes one or more focused light sources, in which light from a source has been focused with one or more lens to a relatively small point of light.

In an aspect, the projector includes a miniaturized projector, e.g., a handheld projector, pocket projector, mobile projector, pico projector, or mini beamer. The one or more miniaturized projectors can include digital light processing, beam-steering, and/or light crystal on silicon technologies. In an aspect, the projector is incorporated into the hand-held hydration monitor. In an aspect, the projector is an adjunct to the hand-held hydration monitor.

In an aspect, the pattern of light emitted from the projector can be formed using any of a number of methods, non-limiting examples of which include beam/splitting, multi-spot, beam shaping, or TopHat. In one embodiment, a form of beam shaping is performed to generate a particular pattern of illuminated light from the light-emitting source. In one embodiment, beam transformers perform a one-to-one mapping of points in an input plane to points in an output plane, a non-limiting example of which is a Gaussian-to-TopHat shaper for a single-mode laser. In one embodiment, band-limited diffusers, diffractive beamsplitters, and/or beam integrators can be used to perform a many-to-one mapping of points in one plane to multiple points in another plane of the beam. The beam is broken up into multiple beamlets and either overlapped (beam integration) or directed into different directions (diffusers and beam splitters). For example, light emitted from laser diodes can be shaped into a variety of patterns, e.g., linear, square, rectangle, grid, round, elliptical, circle/concentric circles, crosshair, or scope using beam-shaping optics, e.g., beam splitters and/or pattern generators, examples of which are commercially available (from, e.g., Frankfurt Laser Company, Freidrichsdorf, Germany). For example, light emitted from LEDs can be collected, collimated and then diffused to shape the beam of light using LED LightShapters™ and Engineered Diffusers™ (from RPC Photonics, Inc., Rochester, N.Y.). In one embodiment, the patterns, e.g., circles, dot matrix, grid, line, square, or crosshair, can be generated using an optical projection head (from, e.g., Edmund Optics, Inc., Barrington, N.J.) attached to a laser or laser diode. Beam splitters, beam shapers, diffusers, Fourier holograms for generating structured light patterns are also available from HOLOEYE Systems Inc., Carlsbad, Calif.; Holo/Or Ltd., Rehovot, Israel; Coherent Inc., Santa Clara, Calif.; and Luminit, LLC, Torrance, Calif.

In one embodiment the pattern of light emitted from the projector is derived from one or more physical lighting template, e.g., a gobo, placed in the path of the emitted light (from e.g., InLight Gobos, Dallas Tex.).

In an aspect, the projected tracer corresponds to a beam width of the transmitted one or more pulses, as illustrated in block 910. For example, the tracer can include a circle of light projected on the target location on the subject to indicate how much of the target location will be covered by the transmitted one or more pulses.

In an aspect, hand-held hydration monitor 200 includes an image-capture device 920 operably coupled to image-capture circuitry 930. In an aspect, the image-capture device includes a camera, e.g., a digital camera. In an aspect, computing component 240 of hand-held hydration monitor 200 includes image-capture circuitry 930 configured to actuate the image-capture device 920 to capture at least one image of the target location on the subject in response to actuation of the micro-impulse radar component. For example, the image-capture circuitry can be configured to capture at least one image of the target location on the subject to document which portion of the subject was scanned with the micro-impulse radar. In an aspect, the at least one image of the target location on the subject is used to verify that the appropriate portion of the subject is scanned. In an aspect, the least one image of the target location on the subject is used as a reference at a future time to perform a rescan of the same target location on the subject. In an aspect, the image-capture circuitry is operably coupled to the micro-impulse radar control circuitry. For example, the micro-impulse radar control circuitry can be configured to transmit a signal to the image-capture circuitry as the micro-impulse radar component is being actuated.

In an aspect, a hand-held hydration monitor such as described herein includes a transmission unit. A "transmission unit," as used herein, can be one or more of a variety of units that are configured to send and/or receive signals, such as signals carried as electromagnetic waves. A transmission unit generally includes at least one antenna and associated circuitry. A transmission unit can include a transmitter and a receiver. A transmission unit can include volatile or non-volatile memory. A transmission unit can include a processor and/or be operably connected to a processor. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice*, 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. A transmission unit can include a hybrid backscatter system configured to function in an RFID, IEEE 802.11x standard and Bluetooth system (see, e.g., U.S. Pat. No. 7,215,976, which is incorporated herein by reference). A transmission unit can include a near field communication (NFC) device. A transmission unit can include a Wireless Identification and Sensing Platform (WISP) device. In an aspect, the transmission unit is operably coupled to the data storage component.

In an aspect, the transmission unit is configured to transmit information associated with the relative hydration state of the tissue of a subject. For example, the transmission unit can be configured to transmit the relative hydration state of the tissue to a second computing component, e.g., a personal computing device, a cell phone, or a laptop computing device. For example, the transmission unit can be configured to transmit the relative hydration state of the tissue to a remote computing device, e.g., a remote computing device associated with a website, the Internet, or the Cloud. In an aspect, the transmission unit is configured to receive information. In an aspect, the transmission unit is configured to receive updates to the stored information associated with the reference reflected pulses correlated with the reference hydration states. In an aspect, the transmission unit is configured to receive updates to the stored identifier information. In an aspect, the transmission unit is configured to receive updates to stored location information.

In an aspect, a hand-held hydration monitor such as described herein includes a power source. In an aspect, the power source provides power to one or more components of the hand-held hydration monitor. For example, the power source can provide power to the micro-impulse radar component, the data storage component, the user interface, and/or the computing component. For example, the power source can provide power to one or more additional components including, but not limited to, an image-capture device, a projector component including at least one light-emitting source, a viewfinder, a location-capture component, and/or a transmission unit. In an aspect, the power source includes a wired connection to a standard electrical outlet. In an aspect, the power source includes a battery. For example, the battery can include a camera or watch sized alkaline, lithium, or silver-oxide battery or other appropriately sized and powered battery. In an aspect, the power source includes a rechargeable battery.

Described herein is a hand-held hydration monitor including a viewfinder including one or more alignment features configured to align with a target on a subject; a microimpulse radar component including a pulse generator and at least one antenna; a data storage component including stored information associated with reference reflected pulses correlated with reference hydration states; a user interface; and a computing component including a processor, the computing component including micro-impulse radar control circuitry configured to actuate the micro-impulse radar component; and hydration determination circuitry configured to receive information associated with one or more reflected pulses from a tissue associated with the target on the subject and to compare the information associated with the one or more reflected pulses from the tissues associated with the target on the subject with stored information associated with the reference reflected pulses correlated with reference hydration states to determine a relative hydration state of the tissue.

Figure 10:
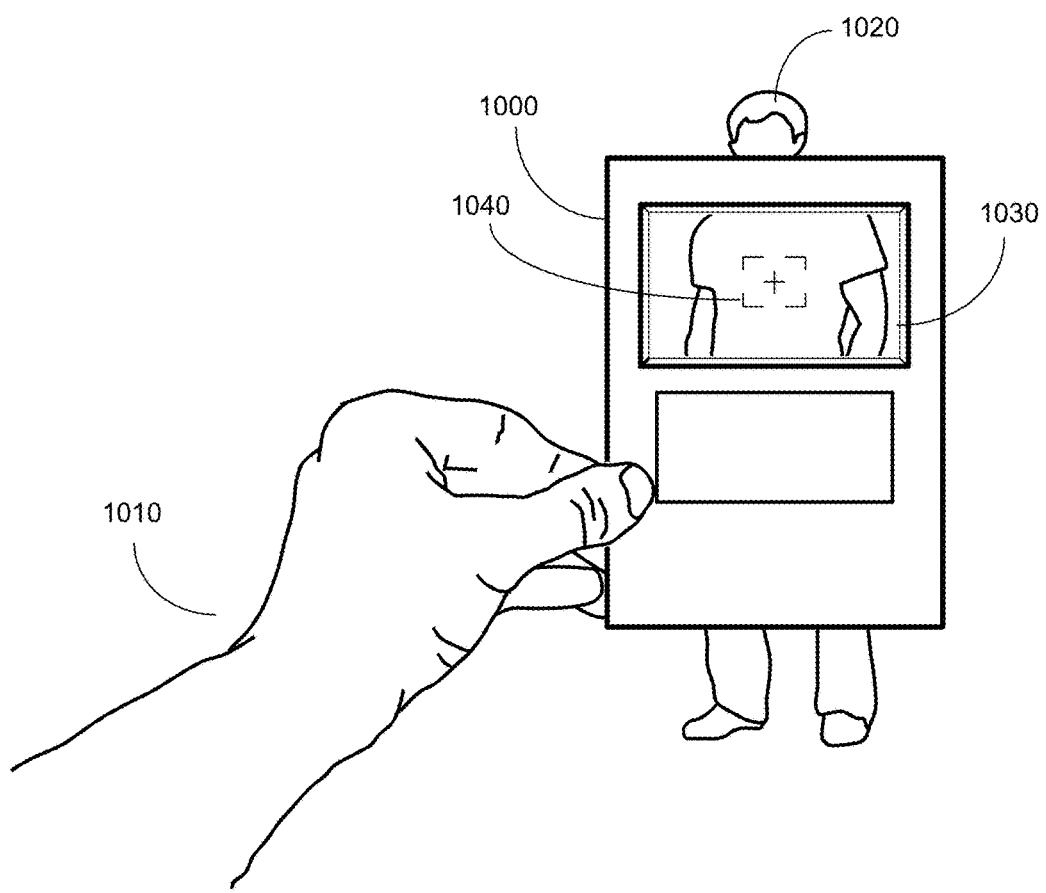
FIG. 10 illustrates an embodiment of a hand-held hydration monitor including a viewfinder.
Figure 11:
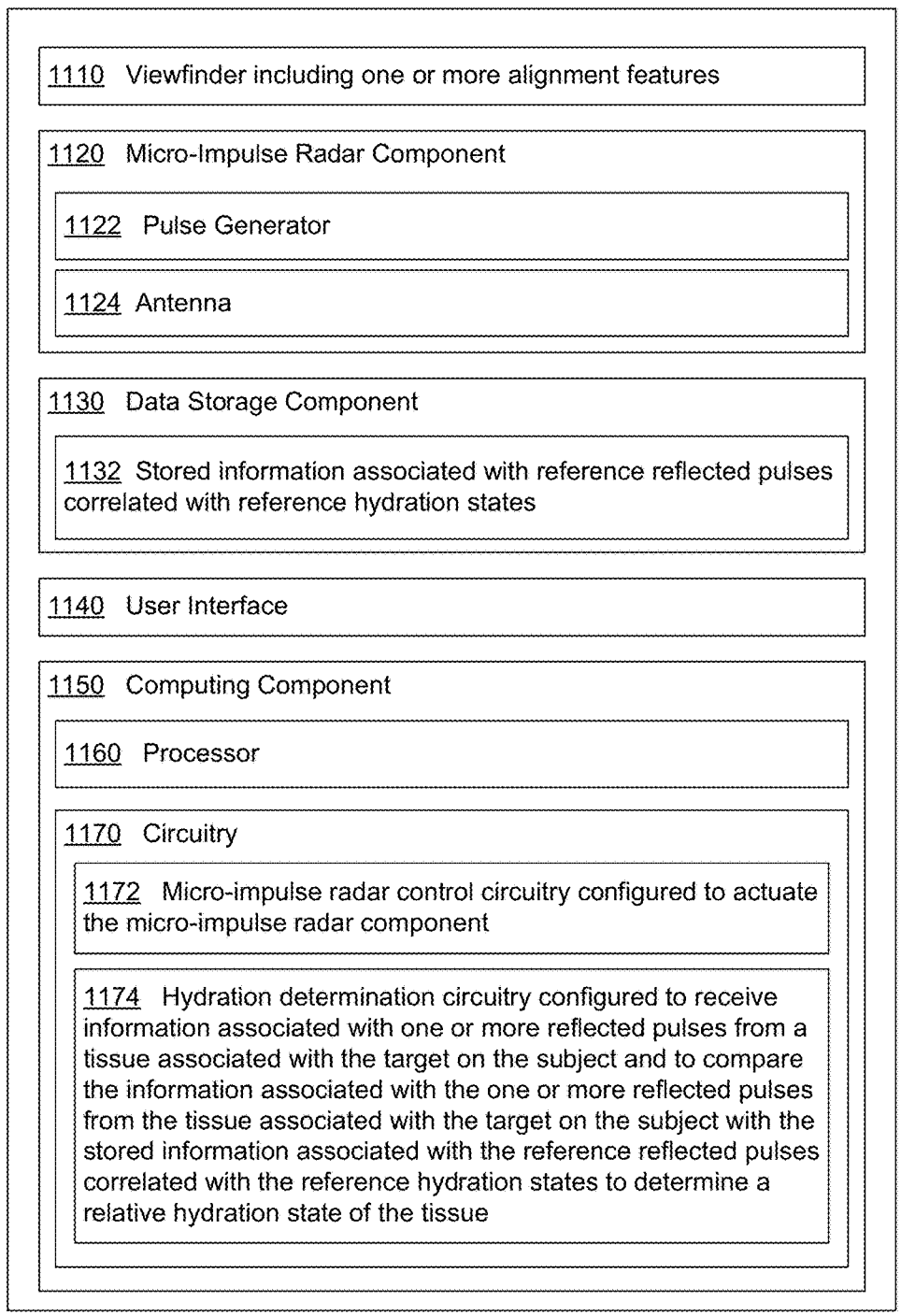
FIG. 11 is a block diagram of an embodiment of a hand-held hydration monitor including a viewfinder.

FIG. 10 illustrates an embodiment of a hand-held hydration monitor including a viewfinder. Hand-held hydration monitor 1000 is shown in the hand of a user 1010. User 1010 is shown viewing a subject 1020 through viewfinder 1030 of the hand-held hydration monitor 1000. The viewfinder 1030 further includes an alignment feature 1040, shown here as a border with a central cross. The alignment feature 1040 is used to align hand-held hydration monitor 1000 with a target, e.g., the torso, of subject 1020. In an aspect, hand-held hydration monitor 1000 further includes a micro-impulse radar component, a data storage component including stored information associated with reference reflected pulses correlated with reference hydration states, and a computing component including a processor and circuitry.

FIGS. 11-17 illustrate aspects of a hand-held hydration monitor including a viewfinder. Hand-held hydration monitor 1100 includes viewfinder 1110 including one or more alignment features configured to align with a target on a subject. In an aspect, the one or more alignment features include at least one of a dot, a circle, a ring, a grid, or a border. In an aspect, the one or more alignment features include one or more lines. In an aspect, the one or more alignment features include an outline of a physical feature of the subject. For example, the alignment feature can include a general outline of a subject's head. Hand-held hydration monitor 1100 includes a micro-impulse radar component 1120 including a pulse generator 1122 and at least one antenna 1124. Hand-held hydration monitor 1100 further includes data storage component 1130 including stored information 1132 associated with reference reflected pulses correlated with reference hydration states. Hand-held hydration monitor 1100 includes user interface 1140, e.g., a display. Hand-held hydration monitor 1100 includes computing component 1150 including processor 1160 and circuitry 1170. Circuitry 1170 includes micro-impulse radar control circuitry 1172 configured to actuate the micro-impulse radar component 1120 and hydration determination circuitry 1174 configured to receive information associated with one or more reflected pulses from a tissue associated with the target on the subject and to compare the information associated with the one or more reflected pulses from the tissue associated with the target on the subject with the stored information 1132 associated with the reference reflected pulses correlated with the reference hydration states to determine a relative hydration state of the tissue.

Figure 12:
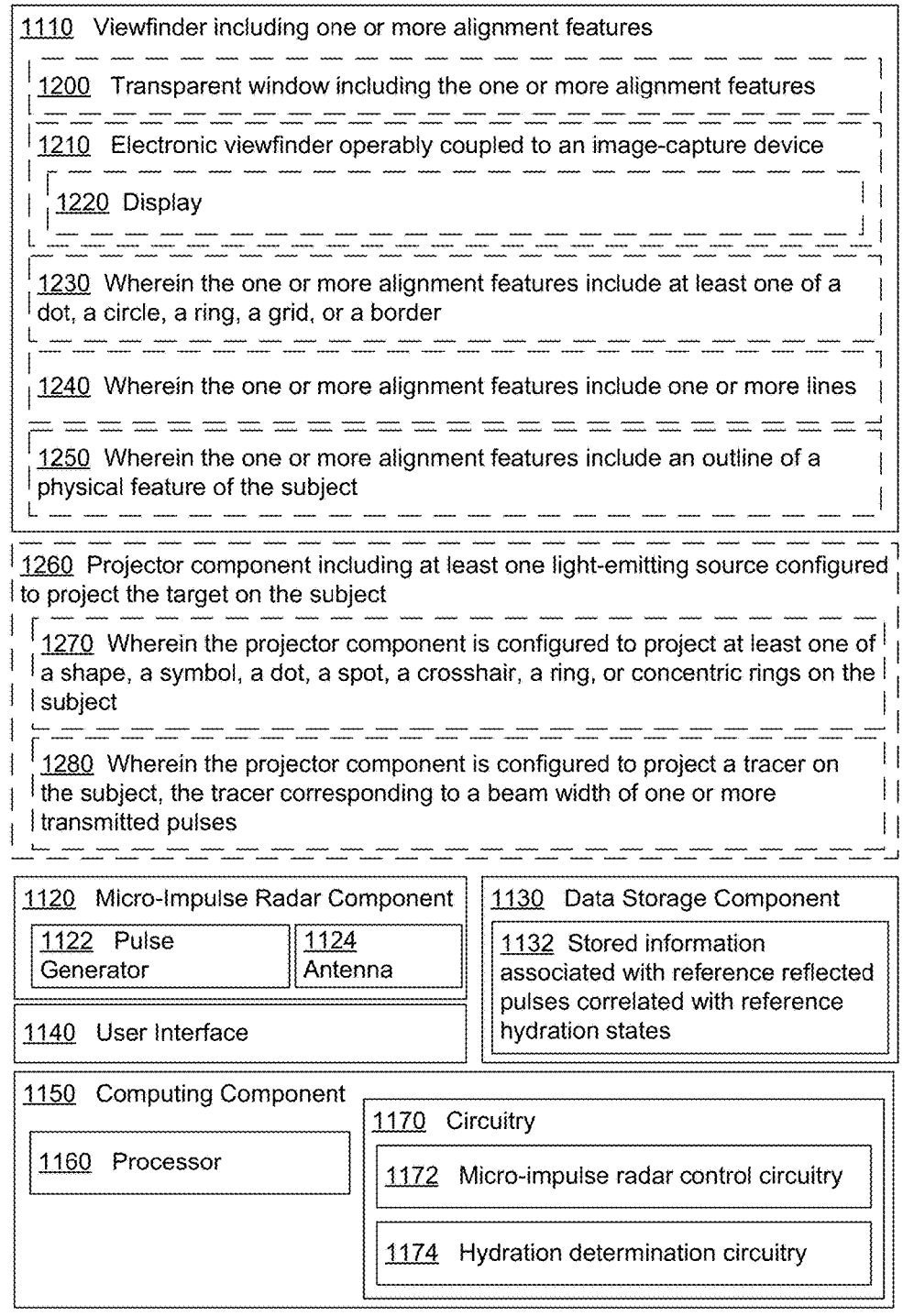
FIG. 12 is a block diagram showing aspects of a hand-held hydration monitor including a viewfinder such as depicted in FIG. 11.

FIG. 12 illustrates further aspects of a hand-held hydration monitor. Hand-held hydration monitor 1100 includes viewfinder 1110 including one or more alignment features configured to align with a target on a subject. In an aspect, viewfinder 1110 includes a transparent window 1200 including the one or more alignment features. For example, the viewfinder can include a transparent window (e.g., of transparent glass or plastic) that includes one or more alignment features associated with the transparent window (e.g., painted, printed, or etched onto the transparent window). For example, the viewfinder can include a transparent window (e.g., of transparent glass or plastic) that includes one or more alignment features projected onto the transparent window. For example, the viewfinder can include a transparent window that includes one or more alignment features electronically displayed on the transparent window. For example, the viewfinder can include a holographic diffraction sight. For example, the viewfinder can include an alignment feature, e.g., a reticle, built into the window and illuminated by a laser diode. For example, the one or more alignment features can be recorded in three-dimensional space onto holographic film at the time of manufacture and incorporated into viewfinder. For example, the viewfinder can include a heads up display including the one or more alignment features.

In an aspect, viewfinder 1110 includes an electronic viewfinder 1210 operably coupled to an image-capture device. In an aspect, the electronic viewfinder 1210 includes a display 1220. In an aspect, the electronic viewfinder includes one or more alignment features overlaid with an image, e.g., an image of the target on the subject, captured with the image-capture device, e.g., a digital camera, and displayed on the display 1220. In an aspect, display 1220 is part of and/or incorporated into user interface 1140.

In an aspect, viewfinder 1110 includes one or more alignment features. In an aspect, the one or more alignment features are configured to align with a target on a subject. In an aspect, the target on the subject as viewed through the viewfinder fills a space delineated by the one or more alignment features. In an aspect, the target on the subject includes a physical feature of the subject. In an aspect, the physical feature of the subject includes at least one of an anatomical feature, a skin feature, or a vascularization feature of the subject. For example, the physical feature of the subject can include an anatomical feature, e.g., all or part of a torso, head, face, arms, legs, or other anatomical features. For example, the physical feature of the subject can include a skin feature, e.g., a pigmented area, a skin texture pattern, a tattoo, a blemish, or a scar. For example, the physical feature of the subject can include a vascularization feature, e.g., a pattern of subsurface blood vessels on a body region of the subject. In an aspect, the one or more alignment features are configured to align with a physical feature of the subject. In an aspect, the one or more alignment features are configured to align with at least one of an anatomical feature, a skin feature, or a vascularization feature of the subject.

In an aspect, the one or more alignment features are configured to align with a target placed on the subject. For example, the one or more alignment features can be configured to align with one or more markings placed on a target location of the subject. For example, the one or more alignment features can be configured to align with one or more washable inks marks, adhesive dots or stickers, or other marking agents placed on or associated with a target location on the subject. For example, the one or more alignment features can be configured to align with one or more markings placed on a piece of apparel, e.g., a shirt, worn over the target location on the subject.

In an aspect, the one or more alignment features are configured to align with a target projected on the subject. In an aspect, hand-held hydration monitor 1100 includes projector component 1260 including at least one light-emitting source configured to project the target on the subject. In an aspect, projector component 1260 is configured to project at least one of a shape, a symbol, a dot, a spot, a crosshair, a ring, or concentric rings on the subject, as shown in block 1270 of FIG. 12. For example, the projector component can be configured to project a series of dots onto a target surface of the subject, the projected series of dots subsequently aligned with a similar series of dots displayed in the viewfinder. Non-limiting aspects of a projector and at least one light-emitting source have been described above herein.

In an aspect, projector component 1260 is configured to project a tracer on the subject. In an aspect, projector component 1260 is configured to project a tracer on a target location on the subject. In an aspect, the tracer is configured to align with the one or more alignment features in the viewfinder. In an aspect, projector component 1260 is configured to project a tracer on the subject, the tracer corresponding to a beam width of one or more transmitted pulses, as illustrate in block 1280. For example, the projector component can project a tracer, e.g., a circle, on a target location on the subject that corresponds in diameter to a beam width of one or more transmitted pulses directed at the target location. In an aspect, the projected tracer provides an indication as to how much of a tissue area will be scanned by the hand-held hydration monitor. For example, the scan area may be restricted to a specific portion of the body and the tracer would provide verification that only that scan area will be subjected to the micro-impulse radar.

Figure 13:
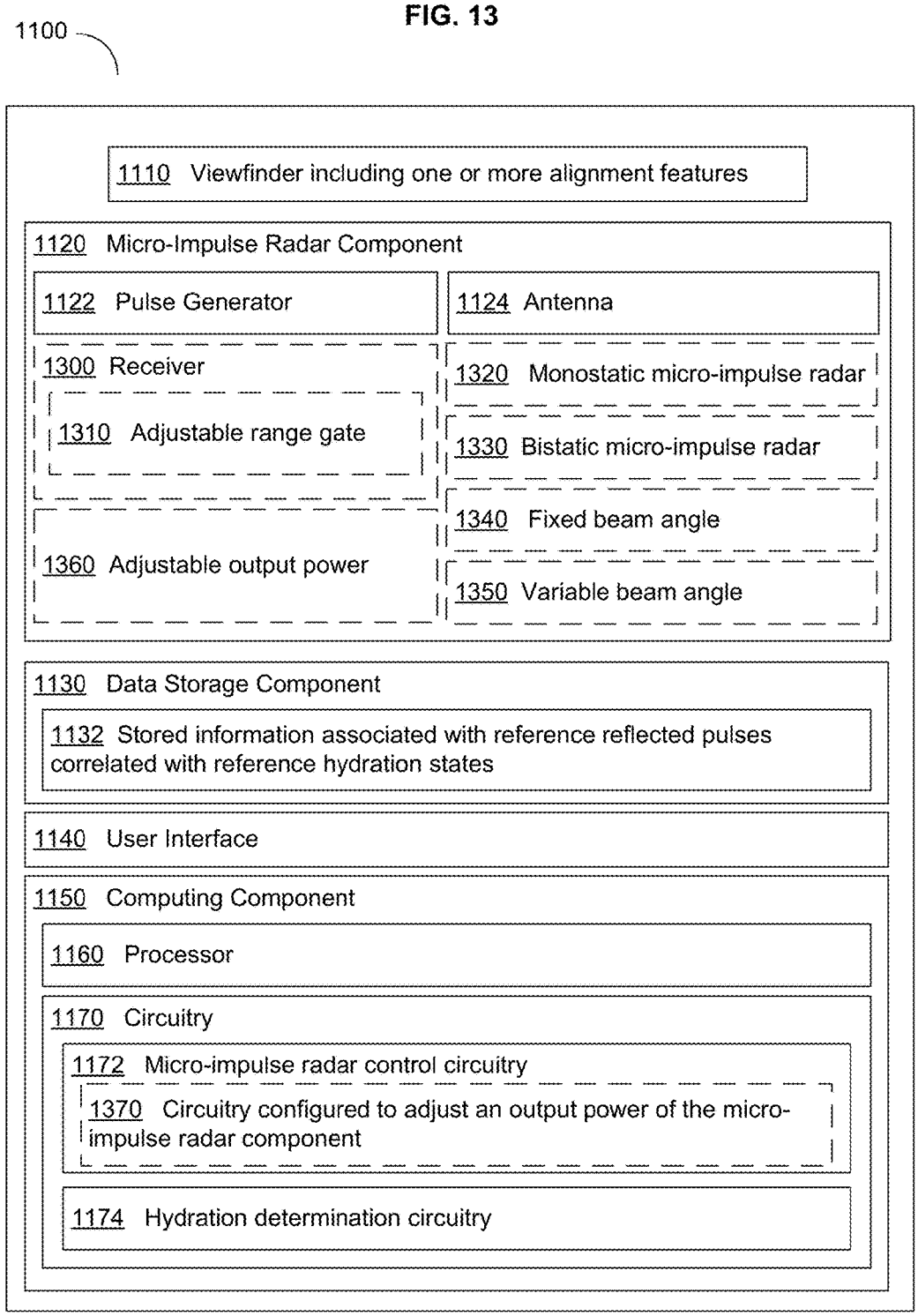
FIG. 13 is a block diagram depicting aspects of a hand-held hydration monitor including a viewfinder such as illustrated in FIG. 11.

FIG. 13 illustrates further aspects of hand-held hydration monitor 1100. A hand-held hydration monitor includes micro-impulse radar component 1120 including pulse generator 1122 and at least one antenna 1124. In an aspect, the micro-impulse radar component 1120 includes at least one receiver 1300. In an aspect, receiver 1300 includes at least one adjustable range gate 1310. In an aspect, the micro-impulse radar component 1120 includes monostatic micro-impulse radar 1320. In an aspect, the monostatic micro-impulse radar 1320 includes a transmitter and a receiver that are collocated. In an aspect, the micro-impulse radar component 1120 includes bistatic micro-impulse radar 1330. In an aspect, the bistatic micro-impulse radar 1330 includes a transmitter and a receiver that are not collocated. In an aspect, the micro-impulse radar component 1120 includes a multistatic micro-impulse radar component. In an aspect, the multistatic micro-impulse radar component includes multiple spatially diverse monostatic radar or bistatic radar components with a shared area of coverage. In an aspect, the micro-impulse radar component 1120 includes a fixed beam angle 1340. In an aspect, the micro-impulse radar component 1120 includes a variable beam angle 1350. In an aspect, hand-held hydration monitor 1100 includes beam width control circuitry configured to adjust a beam width of the micro-impulse radar component. In an aspect, the micro-impulse radar component 1120 includes adjustable output power 1360. In an aspect, micro-impulse radar control circuitry 1172 includes circuitry 1370 configured to adjust an output power of the micro-impulse radar component. Non-limiting aspects of a micro-impulse radar component have been described above herein.

Figure 14:
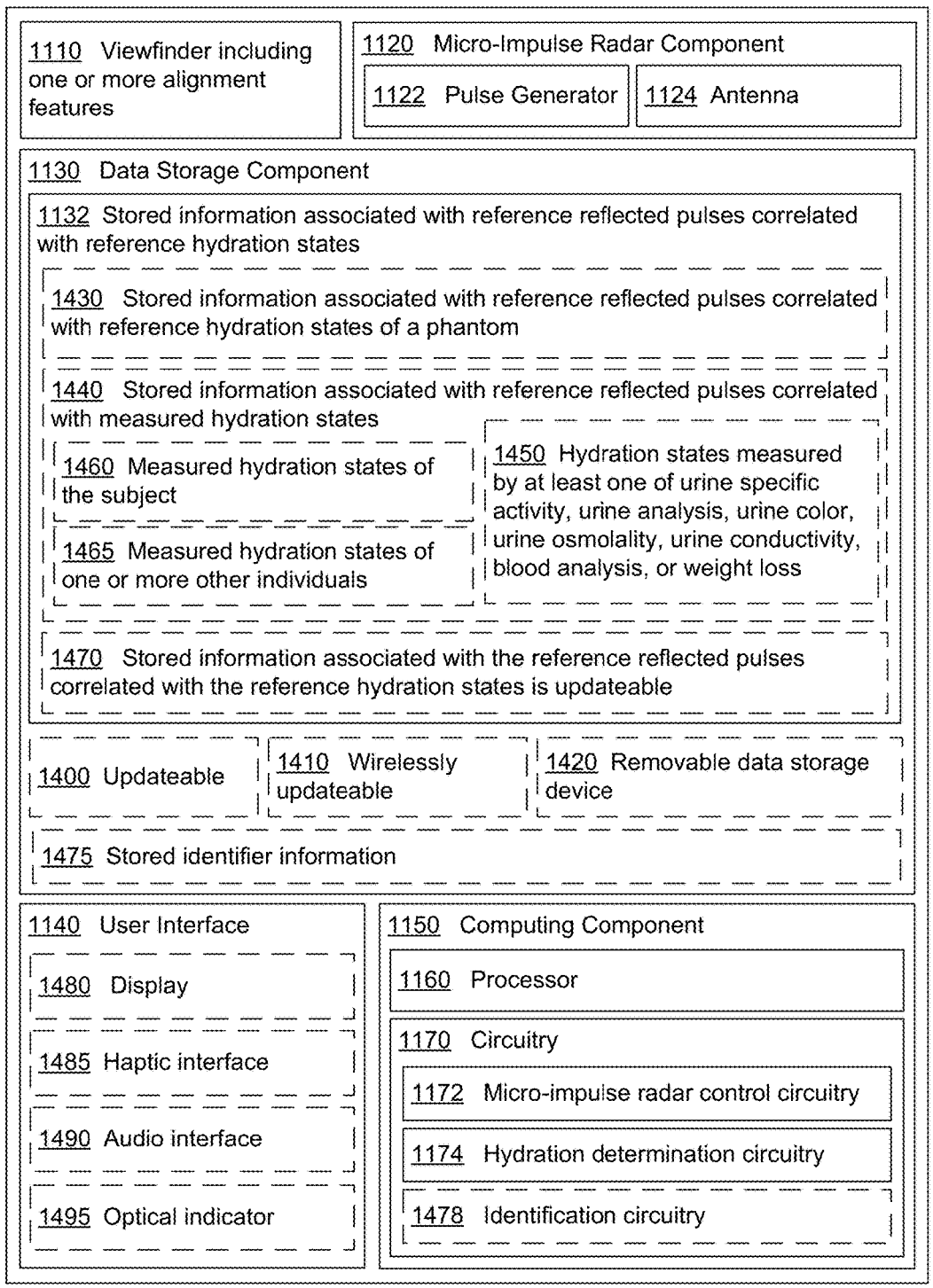
FIG. 14 is a block diagram illustrating aspects of a hand-held hydration monitor including a viewfinder such as shown in FIG. 11.

FIG. 14 illustrates further aspects of a hand-held hydration monitor. Hand-held-hydration monitor 1100 includes data storage component 1130. Data storage component 1130 includes stored information 1132 associated with reference reflected pulses correlated with reference hydration states. In an aspect, the data storage component includes a non-volatile data storage component. In an aspect, the data storage component includes a recordable data storage component. In an aspect, the data storage component includes a mass storage device. In an aspect, the data storage component is operably coupled to a central processing unit of the computing component through input/output channels. In an aspect, the data storage component includes data storage media. In an aspect, the data storage component is included in a hard drive of the computing component.

In an aspect, the data storage component 1130 is updateable 1400. For example, the information stored in the data storage component can be updated, e.g., added to, altered, and/or deleted. In an aspect, the data storage component 1130 is wirelessly updateable 1410. For example, updated information associated with the reference reflected pulses correlated with the reference hydration states can be wirelessly transmitted to the data storage component through a transmission unit associated with the hand-held hydration monitor.

In an aspect, the data storage component is removable. In an aspect, the data storage component 1130 includes a removable data storage device 1420. In an aspect, the data storage component includes a removable memory card or stick. Non-limiting examples of removable data storage include flash memory cards, Memory Sticks, mass storage devices, CompactFlash, non-volatile memory cards, Secure Digital™ (SD) cards, miniSD cards, microSD cards, USB flash drive, or XQD cards. Additional non-limiting aspects of a data storage component have been described above herein.

Data storage component 1130 includes stored information 1132 associated with reference reflected pulses correlated with reference hydration states. In an aspect, the stored information 1132 associated with the reference reflected pulses correlated with the reference hydration states includes stored information 1430 associated with reference reflected pulses correlated with reference hydration states of a phantom. Non-limiting aspects of generating reflected pulses from a phantom have been described above herein.

In an aspect, the stored information 1132 associated with reference reflected pulses correlated with reference hydration states includes stored information 1440 associated with reference reflected pulses correlated with measured hydration states. For example, one or more reference reflected pulses can be correlated with a measured parameter of hydration. For example, the signal properties, e.g., time, frequency and/or amplitude, of one or more reference reflected pulses can be correlated with at least one measured parameter of hydration. In an aspect, the measured hydration states include hydration states measured by at least one of urine specific gravity, urine analysis, urine color, urine osmolality, urine conductivity, blood analysis, or weight loss, as illustrated in block 1450.

In an aspect, the measured hydration states include measured hydration states of the subject 1460. For example, the measured hydration states of the subject can include hydration states ranging from a well-hydrated state to very dehydrated state. For example, the one or more measured hydration states of the subject can include hydration states measured by at least one of urine specific gravity, urine analyses, urine color, urine osmolality, urine conductivity, blood analysis, or weight loss.

In an aspect, the measured hydration states include measured hydration states of one or more other individuals 1465. For example, the measured hydration states of the one or more other individuals can include hydration states of the one or more other individuals ranging from well-hydrated states to very dehydrated states. For example, the measured hydration states can include averages of measured hydrations states from one or more other individuals. For example, the measured hydration states can include measured hydration states from a normalized population matched to the subject, e.g., matched by age, gender, activity level, medical status, etc.

In an aspect, the stored information associated with the reference reflected pulses correlated with the reference hydration states is updateable, as shown in block 1470. For example, the information associated with the reference reflected pulses correlated with the reference hydration states can be updated, e.g., added to, altered, and/or deleted, as new information becomes available.

In an aspect, the data storage component 1130 includes stored identifier information 1475. In an aspect, stored identifier information includes at least one subject identifier for each of one or more subjects. In an aspect, the stored identifier information includes at least one alphanumeric identifier. For example, the stored identifier information can names, ages, telephone numbers, social security numbers, identification numbers, codes, or pin numbers for one or more subjects. In an aspect, the stored identifier information includes one or more biometric parameters for one or more subjects. Non-limiting examples of biometric parameters include fingerprints, facial recognition, voice recognition, retinal scan, DNA, or other biometric features of a subject.

In an aspect, hand-held hydration monitor 1100 includes identification circuitry 1478 configured to compare at least one subject identifier with the stored identifier information and to generate an identifier comparison. In an aspect, the at least one subject identifier includes at least one alphanumeric identifier (e.g., at least one of name, age, telephone number, social security number, or identification number). In an aspect, the at least one subject identifier includes at least one biometric parameter (e.g., fingerprints, facial recognition, voice recognition, retinal scan, DNA, or other biometric feature of the subject). In an aspect, the at least one subject identifier is entered into the hand-held hydration monitor using the user interface. For example, an identification number or code can be entered into a keypad of the hand-held hydration monitor. In an aspect, the at least one subject identifier is entered into the hand-held hydration monitor wirelessly. For example, the at least one subject identifier is received wirelessly by the hand-held hydration monitor from a subject's personal computing device (e.g., a smart phone). For example, the at least one subject identifier is received wireless by the hand-held hydration monitor from a transmitter worn or otherwise associated with the subject. In an aspect, the at least one subject identifier is measured by the hand-held hydration monitor. For example, the hand-held hydration monitor can include a fingerprint scanner. For example, the hand-held hydration monitor can include an image-capture device and facial recognition software. For example, the hand-held hydration monitor can include a microphone and voice recognition software.

In an aspect, the reported identifier comparison is reported to the micro-impulse radar control circuitry. In an aspect, the micro-impulse radar control circuitry includes circuitry configured to actuate the micro-impulse radar component in response to the identifier comparison. For example, the micro-impulse radar control circuitry can be configured to automatically actuate, or to authorize activation of, the micro-impulse radar component upon receipt of an identifier comparison that confirms the identity of the subject. For example, the micro-impulse radar control circuitry can be configured to prevent actuation of the micro-impulse radar component upon receipt of an identifier comparison that cannot confirm the identity of the subject. In an aspect, the reported identifier comparison is reported to alert circuitry. In an aspect, the alert circuitry is configured to generate an alert signal in response to the identifier comparison. For example, the alert circuitry can be configured to generate an alert signal that is transmitted to the user interface upon receipt of an identifier comparison that fails to confirm the identity of the subject.

The hand-held hydration monitor 1100 includes user interface 1140. In an aspect, user interface 1140 is operably coupled to computing component 1150. In an aspect user interface 1140 includes one or more input components and/or output components for use by a user to interface with the hand-held hydration monitor. The one or more input components can be used to enter information into the hand-held hydration monitor, e.g., subject identifiers and/or information, operating instructions, measurement parameters, and the like, and may be integrated into the hand-held hydration monitor or may be one or more peripheral devices operably connected through a wired or wireless connection to the hand-held hydration monitor. Non-limiting examples of input component have been described above herein.

In an aspect, user interface 1130 includes one or more output components over which processed information is transmitted, e.g., viewed, as output results and may be integrated into the hand-held hydration monitor or may be one or more peripheral devices operably connected through a wired or wireless connection to the hand-held hydration monitor. For example, the user interface may be used to alert a user that alignment has or has not been satisfied. For example, the user interface may be used to provide instructions to a user. For example, the user interface may be used to report to a user a relative hydration state of the tissue associated with the target on the subject. Non-limiting examples of output components include but are not limited to displays (e.g., liquid crystal displays), audio speakers, and the like.

In an aspect, user interface 1140 includes display 1480. For example, the user interface can include a liquid crystal display. In an aspect, user interface 1140 includes a haptic interface 1485. For example, the user interface can include a vibrating component. In an aspect, user interface 1140 includes an audio interface 1490. For example, the user interface can include a microphone, a speaker, and an audio signal processor. In an aspect, user interface 1140 includes at least one optical indicator 1495. For example, the at least one optical indicator can include at least one light-emitting diode, e.g., at least one red or green light-emitting diode. Non-limiting examples of user interfaces have been described above herein.

Hand-held hydration monitor 1100 includes computing component 1150 including processor 1160 and circuitry 1170. Non-limiting aspects of a computing component have been described above herein. Computing component 1150 includes circuitry 1170 including micro-impulse radar control circuitry 1172 configured to actuate the micro-impulse radar component and hydration determination circuitry 1174 configured to receive information associated with one or more reflected pulses from a tissue associated with the target on the subject and to compare the information associated with the one or more reflected pulses from the tissue associated with the target on the subject with the stored information associated with the reference reflected pulses correlated with the reference hydration states to determine a relative hydration state of the tissue.

In an aspect, computing component 1150 includes circuitry configured to execute one or more instructions. In an aspect, computing component 1150 includes circuitry configured to execute one or more instructions for actuating the micro-impulse radar component; one or more instructions for receiving the information associated with the one or more reflected pulses from the tissue associated with the target on the subject; and one or more instructions for comparing the information associated with the one or more reflected pulses from the tissue associated with the target on the subject with the stored information associated with the reference reflected pulses correlated with the reference hydration states to determine a relative hydration state of the tissue.

Figure 15:
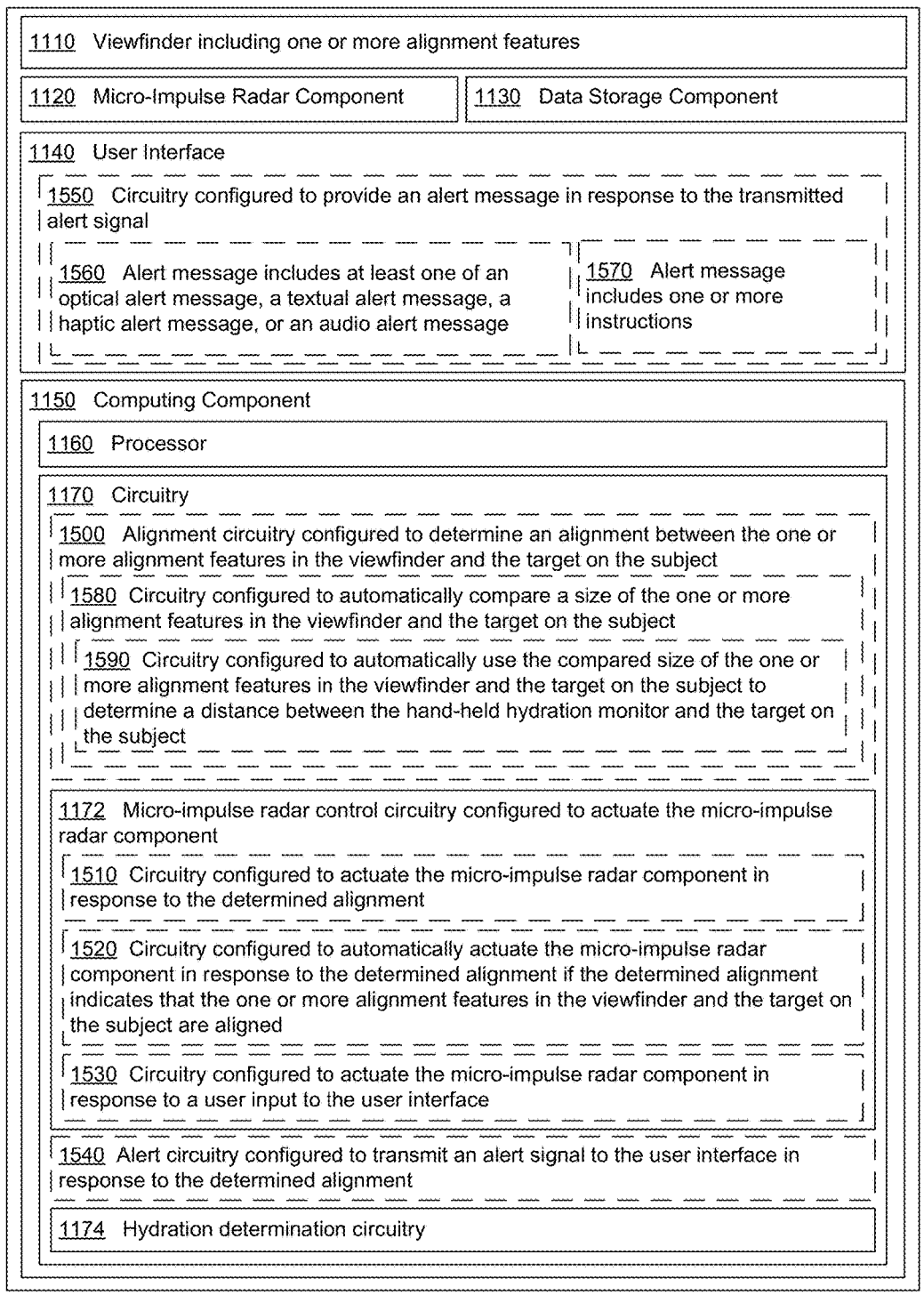
FIG. 15 is a block diagram showing aspects of a hand-held hydration monitor including a viewfinder such as depicted in FIG. 11.

FIG. 15 illustrates further aspects of a hand-held hydration monitor. In an aspect computing component includes alignment circuitry 1500 configured to determine an alignment between the one or more alignment features in the viewfinder and the target on the subject. In an aspect, alignment circuitry 1500 includes circuitry configured to automatically determine an alignment between the one or more alignment features in the viewfinder and the target on the subject. In an aspect, alignment circuitry 1500 includes circuitry configured to determine if the one or more alignment features in the viewfinder and the target on the subject are aligned. In an aspect, alignment circuitry 1500 includes circuitry configured to determine if the one or more alignment features in the viewfinder and the target on the subject are not aligned. In an aspect, the determined alignment indicates that the one or more alignment features in the viewfinder and the target on the subject are aligned. In an aspect, the determined alignment indicates that the one or more alignment features in the viewfinder and the target on the subject are not aligned.

In an aspect, the determined alignment indicates how well the target on the subject as viewed through the viewfinder fills a space delineated by the one or more alignment features. In an aspect, the target is a physical feature of the subject. In an aspect, the target is projected on the subject. In an aspect, the quality of the determined alignment is dependent upon the distance between the hand-held hydration monitor and the subject. For example, if the subject is too far away, the target may not fill the space delineated by the one or more alignment features. For example, if the subject is too close, the target may overfill the space delineated by the one or more alignment features. In an aspect, the degree to which the target overfills or under fills an alignment feature can be used by the alignment circuitry to determine a distance between the hand-held hydration monitor and the subject. For example, if the alignment feature is a silhouette or outline of the subject's head (know or assumed to have a width of 6 inches), and the image of the head in the viewfinder spans only 80% of the size of the alignment feature, then the width of the alignment feature at the target can be determined to be 7.5 inches. If the alignment feature represents a 20 degree projected angle, then the distance to the target can be determined to be approximately 21 inches. This determined distance can be used as a cross-check on a sensor determined distance, or can be used to control distance-dependent features of the hand-held hydration monitor (e.g., to set the power level of the micro-impulse radar pulses, to compare distance to specified minimum or maximum target distances, and the like).

In an aspect, the alignment circuitry includes software and/or algorithms configured to determine an alignment or registration between an image of the target on the subject and the one or more alignment features. In an aspect, the alignment circuitry includes image processing software configured to compare a received image of a target on the subject with the one or more alignment features. In an aspect, the alignment circuitry includes circuitry configured to determine whether the target on the subject fills a space defined or delineated by the one or more alignment features. For example, the alignment circuitry includes circuitry configured to determine whether a subject's head fills or overfills a border associated with the viewfinder of the hand-held hydration monitor. For example, the alignment circuitry includes circuitry configured to identify edges, e.g., the edges of a head or torso, and determine an alignment between the identified edges and the one or more alignment features. For example, the alignment circuitry includes circuitry configured to identify features of the target on the subject, and determine an alignment between the identified features of the target on the subject and the one or more alignment features.

In an aspect, the alignment circuitry includes circuitry configured to compare one or more features detected in an image of the target on the subject with the one or more alignment features in the viewfinder using an alignment or registration algorithm. For example, features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. In an aspect, the alignment circuitry includes circuitry configured to match the features detected in an image of the target on the subject with the one or more alignment features using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser *Image Vision Computing* (2003) 21:977-1000.

In an aspect, the micro-impulse radar control circuitry 1172 includes circuitry 1510 configured to actuate the micro-impulse radar component 1120 in response to the determined alignment. For example, the micro-impulse radar control circuitry can include circuitry configured to authorize or deauthorize activation (e.g., to lock or unlock an on/off switch) of the micro-impulse radar component in response to the determined alignment. In an aspect, the micro-impulse radar control circuitry 1172 includes circuitry configured to actuate the micro-impulse radar component in response to the determined alignment if the determined alignment indicates that the one or more alignment features in the viewfinder and the target on the subject are aligned. In an aspect, the micro-impulse radar control circuitry 1172 includes circuitry 1520 configured to automatically actuate the micro-impulse radar component 1120 in response to the determined alignment if the determined alignment indicates that the one or more alignment features in the viewfinder and the target on the subject are aligned.

In an aspect, the micro-impulse radar control circuitry 1172 includes circuitry 1530 configured to actuate the micro-impulse radar component in response to a user input to the user interface 1120. For example, the micro-impulse radar control circuitry can be configured to actuate the micro-impulse radar component in response to a user pushing an actuation button on the hand-held hydration monitor. For example, the micro-impulse radar control circuitry can be configured to actuate the micro-impulse radar component in response to a user's voice command. In an aspect, a user manually aligns the one or more alignment features in the viewfinder and the target on the subject and manually initiates actuation of the micro-impulse radar component by interfacing with the user interface. For example, a user can point the hand-held hydration monitor at a subject, align the one or more alignment features in the viewfinder with a target on the subject, and once aligned, push an actuation button to initiate actuation of the micro-impulse radar component.

In an aspect, computing component 1150 includes alert circuitry 1540 configured to transmit an alert signal to the user interface in response to the determined alignment. For example, the alert circuitry 1540 can be configured to receive from the alignment circuitry 1500 information associated with the determined alignment. In an aspect, the alert circuitry 1540 includes circuitry configured to transmit an alert signal to the user interface if the determined alignment indicates that the one or more alignment features in the viewfinder and the target on the subject are aligned. In an aspect, the alert circuitry 1540 includes circuitry configured to transmit an alert signal to the user interface if the determined alignment indicates that the one or more alignment features in the viewfinder and the target on the subject are not aligned. In an aspect, the transmitted alert signal indicates that the one or more alignment features in the viewfinder and the target on the subject are aligned. In an aspect, the transmitted alert signal indicates that the one or more alignment features in the viewfinder and the target on the subject are not aligned.

In an aspect, user interface 1140 includes circuitry 1550 configured to provide an alert message in response to the transmitted alert signal. In an aspect, the alert message provided by the user interface indicates that the one or more alignment features in the viewfinder and the target on the subject are aligned. In an aspect, the alert message provided by the user interface indicates that the one or more alignment features in the viewfinder and the target on the subject are not aligned. In an aspect, the alert message includes at least one of an optical alert message, a textual alert message, a haptic alert message, or an audio alert message, as illustrated in block 1560. For example, the alert circuitry can transmit an alert signal to the user interface in response to a determined alignment indicating that the one or more alignment features and the target on the subject are aligned; the user interface providing an alert message, e.g., a green light, indicating to the user that alignment has been achieved. For example, the alert circuitry can transmit an alert signal to the user interface in response to a determined alignment indicating that the one or more alignment features and the target on the subject are not aligned; the user interface providing an alert message, e.g., a red light, indicating to the user that alignment has not been achieved. For example, the user interface can provide an optical alert message, e.g., a green light versus a red light. For example, the user interface can provide a textual alert message, e.g., "aligned" versus "not aligned." For example, the user interface can provide a haptic alert message, e.g., a vibration versus no vibration. For example, the user interface can provide an audio alert message, e.g., "aligned" versus "not aligned." In an aspect, the micro-impulse radar control circuitry includes circuitry configured to actuate the micro-impulse radar component in response to a user input to the user interface in response to an alert message. For example, a user may push an actuation button in response to receiving a green light alert message or an "aligned" textual or audio alert message. For example, a user may adjust the position of the hand-held hydration monitor in response to receiving a red light alert message or a "not aligned" textual or audio alert message so as to adjust the alignment between the one or more alignment features in the viewfinder and the target on the subject.

In an aspect, circuitry 1550 of user interface 1140 is configured to provide an alert message in response to the transmitted signal from alert circuitry 1540. In an aspect, the alert message includes one or more instructions 1570. In an aspect, the alert message includes one or more textual or audio instructions. For example, the alert message can include one or more textual or audio instructions for a user. For example, the alert message can include one or more textual or audio instructions instructing the user to move at least one of right, left, back, or forward to adjust the alignment between the one or more alignment features in the viewfinder with the target on the subject. For example, the alert message can include one or more textual or audio instructions instructing the user to move at least one of right, left, back, or forward to that the target on the subject as viewed through the viewfinder fills a space delineated by the one or more alignment features in the viewfinder. For example, the alert message can include one or more textual or audio instructions instructing the user to push an actuation button to initiate actuation of the micro-impulse radar component. In an aspect, the alert message can include one or more instructions for adjusting a component of the hand-held hydration monitor. For example, the alert message can include one or more instructions for adjusting a parameter of the micro-impulse radar component, e.g., the output power, the beam angle, the beam width, the pulse frequency, the bandwidth, or other aspects of micro-impulse radar component.

In an aspect, the hand-held hydration monitor further includes one or more instructions for treating dehydration. In an aspect, the one or more instructions include sipping small amount of water, drinking carbohydrate/electrolyte containing drinks (e.g., Gatorade or Pedialyte), sucking popsicles made from juices or sports drinks, sucking ice chips. In some instances, if the dehydration symptoms are particularly severe, e.g., elevated resting heart rate and low blood pressure, intravenous fluids may be recommended. The one or more instructions might also include instructions for cooling the person if the dehydration is due to excessive heat exposure or elevated body temperature. The one or more instructions might include removing excess clothing and/or loosening clothing, moving to an air conditioned area, moving in proximity to a fan or into the shade, using a spray bottle or mister to spray lukewarm water on exposed skin surfaces to help with cooling by evaporation.

In an aspect, alignment circuitry 1500 includes circuitry 1580 configured to automatically compare a size of the one or more alignment features in the viewfinder and the target on the subject. In an aspect, circuitry 1580 includes circuitry 1590 configured to automatically use the compared size of the one or more alignment features in the viewfinder and the target on the subject to determine a distance between the hand-held hydration monitor and the target on the subject. In an aspect, the micro-impulse radar control circuitry includes circuitry configured to automatically actuate the micro-impulse radar component if the determined distance is within a range of predetermined operating distances of the hand-held hydration monitor. In an aspect, the micro-impulse radar control circuitry includes circuitry configured to prevent actuation of the micro-impulse radar component if the determined distance is not within a range of predetermined operating distances of the hand-held hydration monitor.

Figure 16:
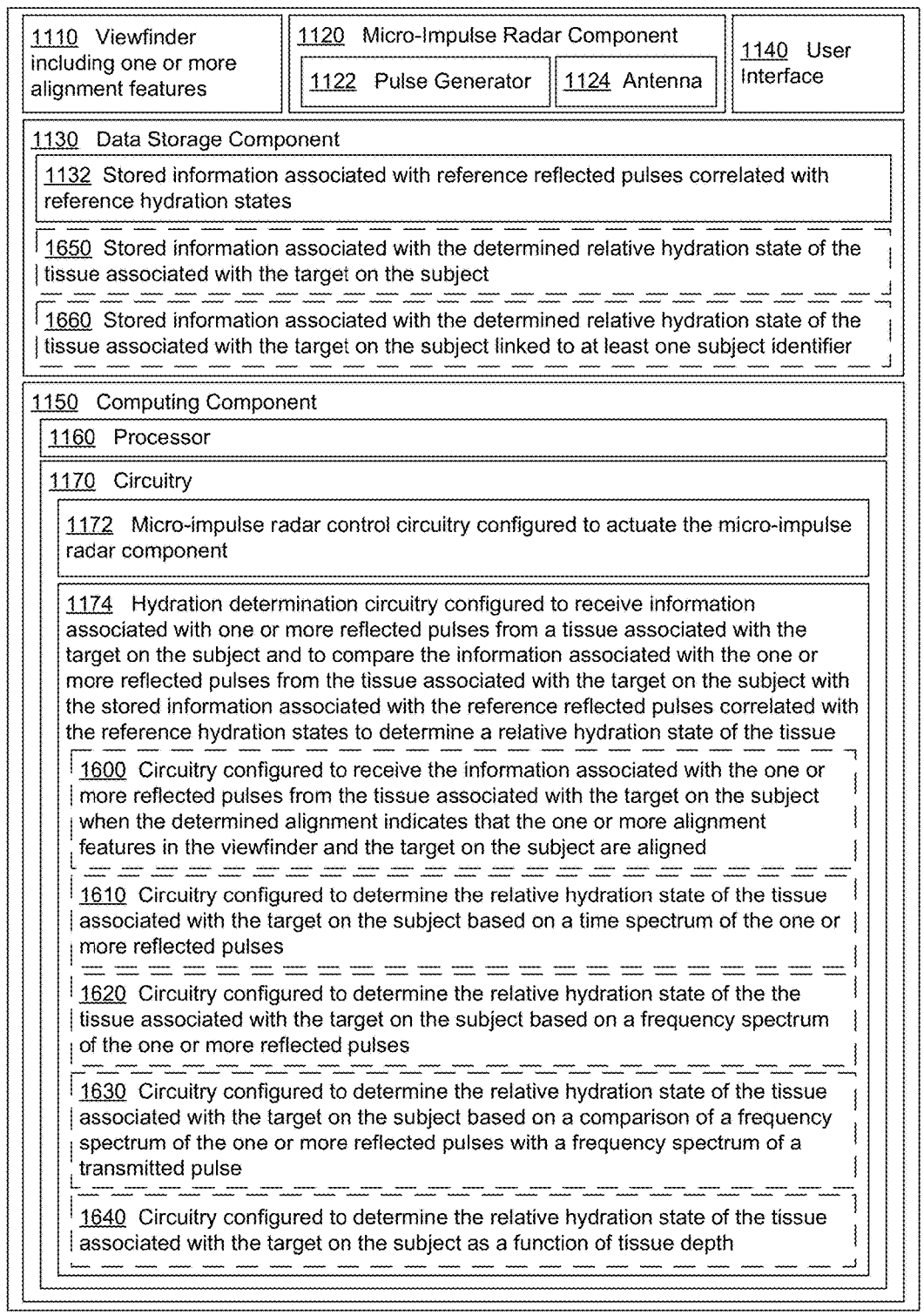
FIG. 16 is a block diagram depicting aspects of a hand-held hydration monitor including a viewfinder such as illustrated in FIG. 11.

FIG. 16 illustrates further aspects of a hand-held hydration monitor. Hand-held hydration monitor 1100 includes hydration determination circuitry 1174 configured to receive information associated with one or more reflected pulses from a tissue associated with the target on the subject and to compare the information associated with the one or more reflected pulses from the tissue associated with the target on the subject with the stored information associated with the reference reflected pulses correlated with the reference hydration states to determine a relative hydration state of the tissue. In an aspect, hydration determination circuitry 1174 includes circuitry 1600 configured to receive the information associated with the one or more reflected pulses from the tissue associated with the target on the subject when the determined alignment indicates that the one or more alignment features in the viewfinder and the target on the subject are aligned. In an aspect, the hydration determination circuitry includes circuitry to only receive the one or more reflected pulses from the tissue associated with the target on the subject when the one or more alignment features in the viewfinder and the target on the subject are aligned. In an aspect, the hydration determination circuitry includes circuitry to block receipt of the one or more reflected pulses from the tissue associated with the target on the subject when the determined alignment indicates that the one or more alignment features in the viewfinder and the target on the subject are not aligned. In an aspect, the hydration determination circuitry includes circuitry configured to block processing, to block storage, or to block reporting of signals associated with the one or more reflected pulses from the tissue associated with the target on the subject when the determined alignment indicates that the one or more alignment features in the viewfinder and the target on the subject are not aligned.

In an aspect, hydration determination circuitry 1174 includes circuitry 1610 configured to determine the relative hydration state of the tissue associated with the target on the subject based on a time spectrum of the one or more reflected pulses. In an aspect, hydration determination circuitry 1174 includes circuitry 1620 configured to determine the relative hydration state of the tissue associated with the target on the subject based on a frequency spectrum of the one or more reflected pulses. In an aspect, hydration determination circuitry 1174 includes circuitry 1630 configured to determine the relative hydration state of the tissue associated with the target on the subject based on a comparison of a frequency spectrum of the one or more reflected pulses with a frequency spectrum of a transmitted pulse. In an aspect, hydration determination circuitry 1174 includes circuitry 1640 configured to determine the relative hydration state of the tissue associated with the target on the subject as a function of tissue depth.

In an aspect, data storage component 1130 is configured to stored information associated with the determined relative hydration state. In an aspect, data storage component 1130 includes stored information 1650 associated with the determined relative hydration state of the tissue associated with the target on the subject. In an aspect, data storage component 1130 includes stored information 1660 associated with the determined relative hydration state of the tissue associated with the target on the subject linked to at least one subject identifier. For example, the determined relative hydration state of the tissue associated with the target on the subject can be linked to the subject's name, identification number, or biometric property. In an aspect, data storage component includes stored information associated with the determined relative hydration state of the tissue associated with the target on the subject linked to a determined distance. For example, the data storage component can include stored information associated with hydration states of a tissue associated with a target on a subject measured with the hand-held hydration monitor at different distances from the subject.

Figure 17:
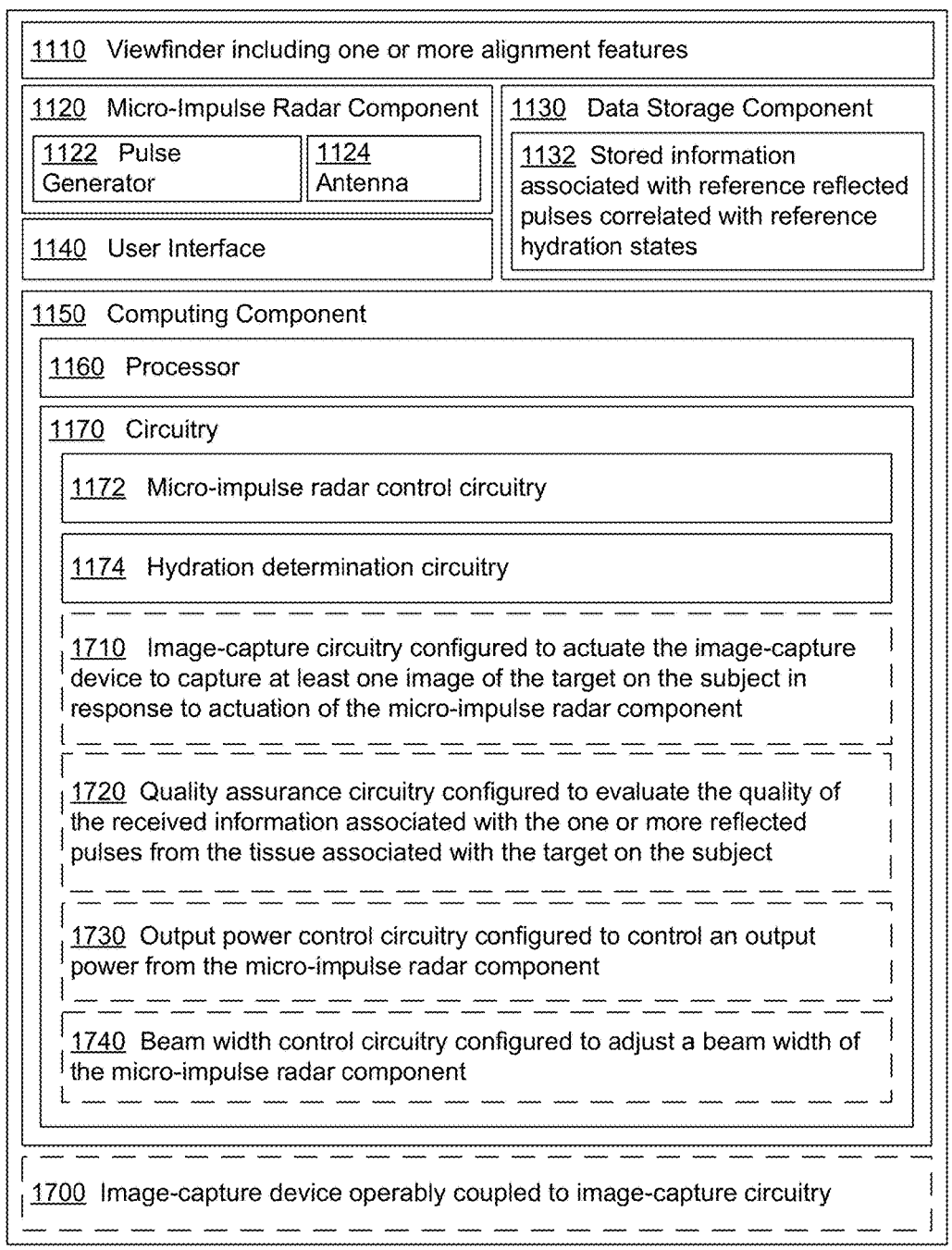
FIG. 17 is a block diagram illustrating aspects of a hand-held hydration monitor including a viewfinder such as shown in FIG. 11.

FIG. 17 illustrates further aspects of a hand-held hydration monitor. In an aspect, hand-held hydration monitor 1100 includes image-capture device 1700 operably coupled to image-capture circuitry 1710. In an aspect, the image-capture device includes a camera, e.g., a digital camera. In an aspect, circuitry 1170 of computing component 1150 includes image-capture circuitry 1710 configured to actuate the image-capture device 1700 to capture at least one image of the target on the subject in response to actuation of the micro-impulse radar component. For example, the image-capture circuitry can be configured to capture at least one image of the target on the subject to document which portion of the subject was scanned with the micro-impulse radar. In an aspect, the at least one image of the target on the subject is used to verify that the appropriate portion of the subject is scanned. In an aspect, the least one image of the target on the subject is used at a future time to perform a rescan of the same location or target on the subject. In an aspect, the image-capture circuitry is operably coupled to the micro-impulse radar control circuitry. For example, the micro-impulse radar control circuitry can be configured to transmit a signal to the image-capture circuitry as the micro-impulse radar component is being actuated to initiate image capture.

In an aspect, computing component 1150 includes quality assurance circuitry 1720 configured to evaluate the quality of the received information associated with the one or more reflected pulses from the tissue associated with the target on the subject. In an aspect, the quality assurance circuitry includes circuitry configured to evaluate the quality of the received information associated with the one or more reflected pulses from the tissue against a quality threshold. In an aspect, the quality threshold can include a signal-to-noise threshold. For example, the quality assurance circuitry can include circuitry configured to determine whether a return signal generated by the one or more reflected pulses is adequate, e.g., above a signal-to-noise threshold. In an aspect, the quality threshold can include a "reasonability" threshold. For example, is the received information associated with the one or more reflected pulses reasonable (e.g., in terms of amplitude, frequency, and the like), for the measuring conditions. If the quality threshold indicates that the received information associated with the one or more reflected pulses is good, then the comparison of the received information with the stored information can proceed. If the quality threshold indicates that the received information associated with the one or more reflected pulses is bad, then additional information is required. In an aspect, the micro-impulse radar control circuitry includes circuitry configured to actuate the micro-impulse radar component to transmit one or more additional pulses to the target on the subject if the evaluated quality of the received one or more reflected pulses fails to meet or exceed the quality threshold.

In an aspect, computing component 1150 includes output power control circuitry 1730 configured to control output power from the micro-impulse radar component 1120. In an aspect, micro-impulse radar component 1120 is configured to transmit ultra-wideband pulses of sufficient energy so that the reflected pulses are detectable by the receiver. For example, the output power control circuitry can be configured to increase or decrease the output power of the micro-impulse radar component in response to a quality threshold.

In an aspect, computing component 1150 includes beam width control circuitry 1740 configured to adjust a beam width of the micro-impulse radar component. In an aspect, beam width control circuitry 1740 includes circuitry configured to adjust the beam angle of the micro-impulse radar component to alter the beam width of the transmitted radar pulses at the target on the subject. For example, the beam width control circuitry can be configured to adjust the beam angle of the micro-impulse radar is response to changes in distance between the hand-held hydration monitor and the subject. For example, the beam width control circuitry can be configured to adjust the beam angle of the micro-impulse radar component in response to changes in the desired coverage area at the target on the subject.

Described herein is a hand-held hydration monitor including a location-capture component configured to capture information associated with a location on a subject; a micro-impulse radar component including a pulse generator and at least one antenna; a data storage component including stored location information and stored information associated with reflected pulses correlated with reference hydration states; a user interface; and a computing component including a processor and circuitry, the circuitry including registration circuitry configured to compare the captured information associated with the location on the subject with the stored location information and to determine a registration value; micro-impulse radar control circuitry configured to actuate the micro-impulse radar component; and hydration determination circuitry configured to receive information associated with one or more reflected pulses from a tissue associated with the location on the subject and to compare the information associated with the one or more reflected pulses from the tissue with the stored information associated with the reference reflected pulses correlated with the reference hydration states to determine a relative hydration state of the tissue.

Figure 18:
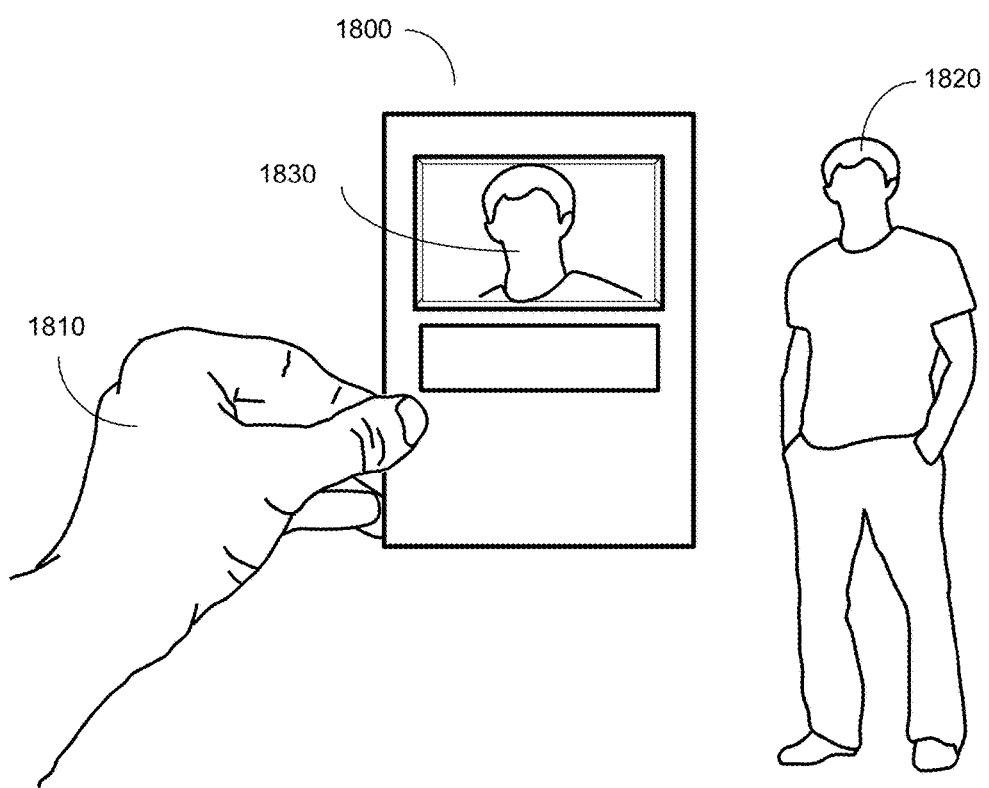
FIG. 18 illustrates an embodiment of a hand-held hydration monitor.
Figure 19:
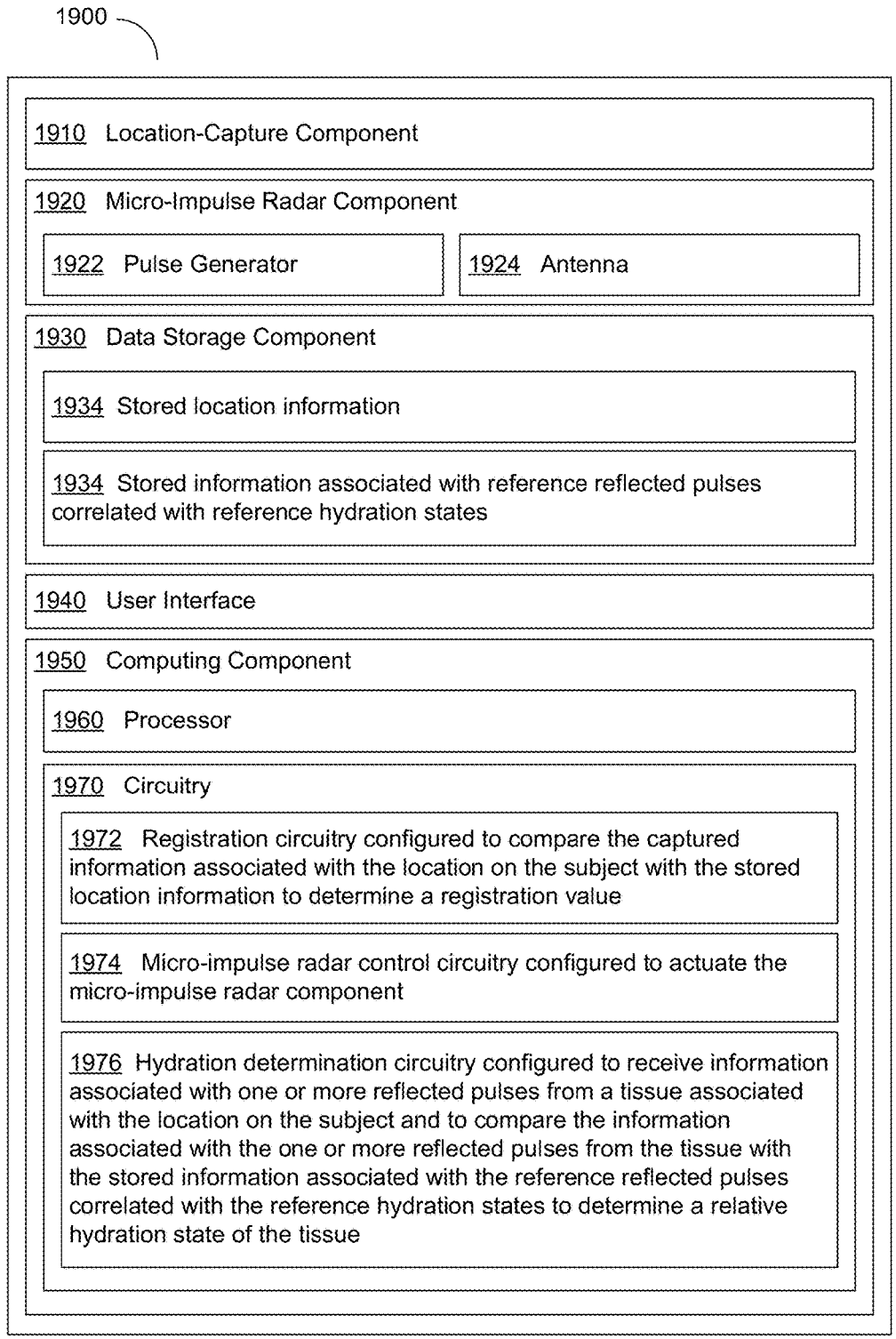
FIG. 19 is a block diagram of an embodiment of a hand-held hydration monitor including a location-capture component.

FIG. 18 illustrates an embodiment of a hand-held hydration monitor including a location-capture component. Hand-held hydration monitor 1800 is shown in the hand of a user 1810. User 1810 is shown pointing the hand-held hydration monitor 1800 at a subject 1820 and capturing an image 1830 of a location on the subject 1820. In this non-limiting example, the location on the subject is the subject's head. Hand-held hydration monitor 1800 includes registration circuitry configured to compare image 1830 with one or more stored images to determine if the location on the subject 1820 depicted in the image 1830 is the appropriate location for radar scanning by the hand-held hydration monitor 1800. In an aspect, hand-held hydration monitor 1800 further includes a micro-impulse radar component, a data storage component including stored location information (e.g., stored images) and stored information associated with reference reflected pulses correlated with reference hydration states, and a computing component including a processor and circuitry.

FIGS. 19-25 illustrate aspects of a hand-held hydration monitor including a location-capture component. Hand-held hydration monitor 1900 includes location-capture component 1910 configured to capture information associated with a location on a subject. Hand-held hydration monitor 1900 further includes micro-impulse radar component 1920 including a pulse generator 1922 and at least one antenna 1924. Hand-held hydration monitor 1900 includes data storage component 1930 including stored location information 1932 and stored information 1934 associated with reference reflected pulses correlated with reference hydration states. Hand-held hydration monitor 1900 includes a user interface 1940. Hand-held hydration monitor 1900 includes computing component 1950 including processor 1960 and circuitry 1970. Circuitry 1970 includes registration circuitry 1972 configured to compare the captured information associated with the location on the subject with the stored location information 1932 to determine a registration value. Circuitry 1970 includes micro-impulse radar control circuitry 1974 configured to actuate the micro-impulse radar component 1920. Circuitry 1970 includes hydration determination circuitry 1976 configured to receive information associated with one or more reflected pulses from a tissue associated with the location on the subject and to compare the information associated with the one or more reflected pulses from the tissue with the stored information 1934 associated with reference reflected pulses correlated with reference hydration states to determine a relative hydration state of the tissue.

Figure 20:
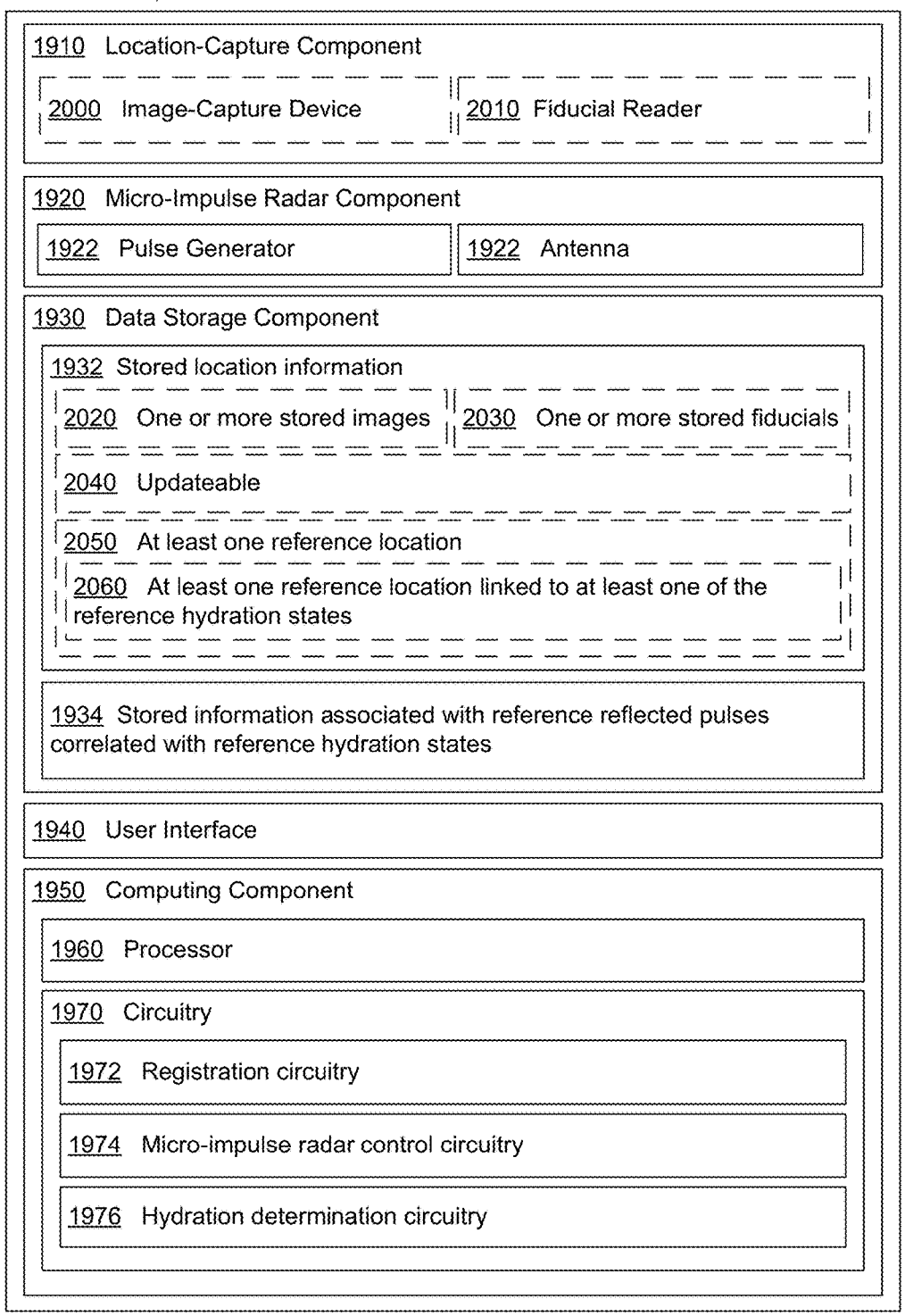
FIG. 20 is a block diagram showing aspects of a hand-held hydration monitor including a location-capture component such as depicted in FIG. 19.

FIG. 20 illustrates further aspects of a hand-held hydration monitor including a location-capture component. Hand-held hydration monitor 1900 includes location-capture component 1910 configured to capture information associated with a location on a subject. In an aspect, the location-capture component includes circuitry configured to determine a location on the skin surface of an individual. In an aspect, the location-capture component is configured to capture one or more images associated with the location on the subject. In an aspect, the location-capture component measures an inherent feature of the location, e.g., a physical landmark associated with the location on the subject. In an aspect, the one or more physical landmarks include one or more of a pigmentation, pigmented area, skin texture pattern, tattoo, blemish, scar, anatomical feature, or subsurface blood vessel on the skin surface of the individual. For example, the one or more physical landmarks can include one or more pigmented areas such as freckles or moles or one or more anatomical features such as a nose, lip, cheek, eye, brow, joint, or other anatomical features. An extensive list of landmarks of the facial area, for example, are described in Buckley et al., *Am. J. Psychiatry* (2005) 162: 606-608, which is incorporated herein by reference.

In an aspect, the location-capture component is configured to capture one or more fiducials associated with the location on the subject. In an aspect, the location-capture component measures an artificial feature of the location, e.g., one or more fiducial markers placed on the location on the subject. In an aspect, the one or more fiducial markers can include one or more washable ink spots, adhesive dots or stickers, or other markings placed on the location on the subject prior to measuring the location. For example, the one or more fiducial markers are placed on a skin surface of the subject. For example, the location-capture component can be configured to capture one or more fiducials associated with a skin surface (e.g., a forehead or torso skin surface) of the subject. For example, the one or more fiducial markers are incorporated into an object worn by the subject, e.g., a piece of clothing. For example, the location-capture component can be configured to capture one or more fiducial markers associated with an article of clothing (e.g., a T-shirt) worn by the subject. In an aspect, the one or more fiducial markers include one or more of radiofrequency identification (RFID) tags, electronic nodes, magnetic nodes, or audio nodes. For example, the one or more fiducial markers can include one or more RFID tags placed at various locations on a skin surface of the subject or an article of clothing worn by the subject.

In an aspect, the location-capture component 1910 includes an image-capture device 2000. In an aspect, the image-capture device is configured to capture one or more images of a location on a subject. In an aspect, the location-capture component includes an image-capture device configured to capture one or more visible, infrared, or ultraviolet images of a location on the subject. In an aspect, the location-capture component includes at least one of a visible, infrared, ultraviolet, polarized, or spectrally limited light source. For example, the image-capture device can include one or more passive or active scanners, digital cameras, charge-coupled device (CCD), complementary metal oxide semiconductor (CMOS), infrared sensor, ultraviolet sensor, or any other device suited to capturing an image of a location on a subject. Other non-limiting examples of an image-capture device include an ultrasound device, a photoacoustic device, a thermal imaging device, a capacitance measuring device, an electomyographic device, or other biomedical imaging devices. In an aspect, the micro-impulse radar component and associated signal processing perform as am image-capture device, providing an "image" of a location on the subject.

In an aspect, the image-capture device includes at least one camera, e.g., a digital camera, configured to capture one or more images of a location on the subject. In an aspect, the at least one camera may capture one or more images in the visible spectrum. In an aspect, the at least one camera may capture one or more images in other portions of the electromagnetic spectrum, e.g., infrared or ultraviolet. The image-capture device can include one or more electronic image sensors, e.g., photodiodes, photoresistors, charge-coupled devices (CCD), and/or complementary metal oxide semiconductor (CMOS) devices. In an aspect, the image-capture device includes a single-shot capture device with one CCD with a Bayer filter mosaic or three separate image sensors, which are exposed to the same image via a beam splitter. In an aspect, the image-capture device includes a multi-shot capture device. For example, a single CCD sensor may obtain additive color information by capturing an image three times, each with a different filter (e.g., red, green, and blue).

In an aspect, the location-capture component includes an active scanner. An active scanner emits some form of radiation or light which when beamed onto a surface (e.g., the surface of the subject) creates a measurable reflection. The emitted radiation or light can include electromagnetic radiation, ultrasound, or x-ray. Non-limiting examples of active non-contact scanners include hand-held laser scanners as well as a number of three-dimensional scanners (3D scanners) including time-of-flight scanners, triangulation laser scanners, structured-light scanners, and modulated light scanners. In some embodiments, the one or more active scanners can include one or more time-of-flight laser scanners in which a laser rangefinder is used to determine the distance between a surface, e.g., the one or more regions of an individual, and the laser emitter by timing the round-trip time of a pulse of light. The time-of-flight laser scanner scans the entire field of view one point at a time by changing the rangefinders view. Scanners for scanning head, face and/or whole body are commercially available (from, e.g., Cyberware, Monterery Calif.; Accurex Measurement Inc., Swathmore, Pa.; 3dMD Atlanta, Ga.; Konica/Minolta, Ramsey, N.J.)

In an aspect, the location-capture component 1910 includes a fiducial reader 2010. In an aspect, the location-capture component includes a fiducial reader that reads one or more fiducials associated with the location on the subject. In an aspect, the one or more fiducials are inherent properties of the skin surface, e.g., physical landmarks on the skin surface of the subject. For example, the one or more physical landmarks can include one or more of a pigmentation, pigmented area, skin texture pattern, tattoo, blemish, scar, anatomical feature, or subsurface blood vessel on the skin surface of the subject. In an aspect, each subject is associated with a unique pattern of physical landmarks. For example, a unique pattern of physical landmarks may serve to locate the target location on the subject as well as identify the subject.

In an aspect, the fiducial reader reads one or more fiducial markers, e.g., spots or templates, placed on the location of the subject prior scanning with the micro-impulse radar component. For example, the fiducial reader, e.g., an image-capture device such as a digital camera, can image one or more washable ink spots, adhesive dots or stickers, or other marking agents placed on the skin surface of the subject prior to scanning with the micro-impulse radar component. For example, the fiducial reader can image one or more markings associated with an article of clothing worn by the subject, the one or more markings overlapping the location of interest on the subject. In an aspect, the one or more fiducial markers include one or more of radiofrequency identification (RFID) tags, electronic nodes, magnetic, or audio nodes. For example, the fiducial reader can include a radiofrequency antenna including circuitry to receive a radiofrequency signal from one or more RFID tags placed on the skin surface of the subject or worn in an article of clothing. In an aspect, the location-capture component includes a fiducial reader that includes a receiver for signals sent from one or more fiducial markers that are electronic nodes. In an aspect, the location-capture component includes a fiducial reader that includes an audio receiver, e.g., a microphone, for signals sent from one or more fiducial markers that are audio nodes.

The data storage component 1930 of hand-held hydration monitor 1900 includes stored location information 1932. In an aspect, the stored location information 1932 includes one or more stored images 2020. In an aspect, the one or more stored images 2020 include one or more images captured with an image-capture device. In an aspect, the one or more stored images include one or more stored images of locations on each subject. For example, the one or more stored images can include one or more reference images of the location on the subject captured at a previous point in time. For example, the one or more stored images can include at least one image of a previously scanned location on the subject. In an aspect, each subject is associated with or linked to a unique image of a location on said subject. For example, a unique image of a location on the subject may serve to locate the target location on the subject as well as identify the subject. In an aspect, the one or more stored images include one or more stored images of generalized body regions. For example, the one or more stored images can include one or more images of specific body regions, e.g., generalized images of legs, arms, torsos, or heads. In an aspect, at least one of the one or more stored images includes an outline of a generalized body region. For example, the stored images can include stored outline images of legs, arms, torsos, or heads.

In an aspect, the stored location information 1932 includes one or more stored fiducials 2030. For example, the stored location information can include stored patterns of fiducials, e.g., patterns of physical landmarks on the surface of the subject and/or patterns of fiducial markers placed on or worn by the subject. For example, the subject may wear a team jersey or other article of clothing that includes a set of fiducial markers arranged in a pattern over a location on the subject routinely targeted for hydration monitoring with the hand-held hydration monitor. In an aspect, each subject is associated with a unique pattern of fiducial markers. For example, a unique pattern of fiducial markers may serve to locate the target location on the subject as well as identify the subject.

In an aspect, the stored location information 1932 is updateable 2040. For example, the stored location information can be updated, e.g., added to, modified, or deleted, as new location information becomes available.

In an aspect, the stored location information 1932 includes at least one reference location 2050. For example, the stored location information can include a reference location, e.g., the center of the torso, which is routinely scanned by the hand-held hydration monitor for hydration state determination. In an aspect, the reference location includes a location on the subject previously scanned with the hand-held hydration monitor. In an aspect, the reference location includes a normalized location on a population of subjects. In an aspect, the stored location information 1932 includes at least one reference location linked to at least one of the reference hydration states 2060. For example, the reference location, e.g., the center of the torso, can be linked to reference hydration states. In an aspect, the reference hydration states for a given reference location include previous determined relative hydrations states of a subject for a given location. In an aspect, the reference hydration states for a given reference location include normalized hydration state information for a given location from a population of subjects.

Figure 21:
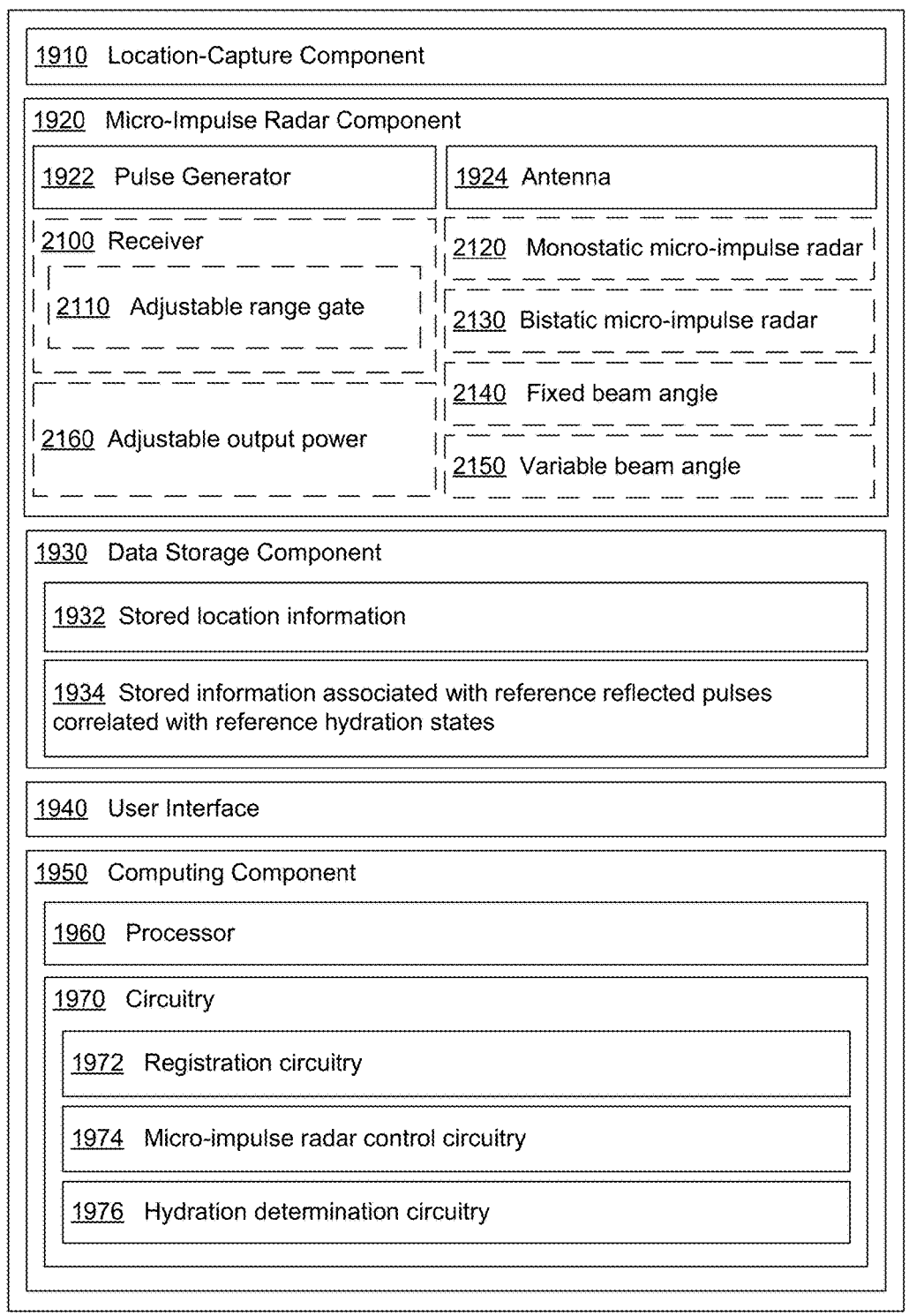
FIG. 21 is a block diagram depicting aspects of a hand-held hydration monitor including a location-capture component such as illustrated in FIG. 19.

FIG. 21 illustrates further aspects of a hand-held hydration monitor including a location-capture component. Hand-held hydration monitor 1900 includes micro-impulse radar component 1920 including pulse generator 1922 and at least one antenna 1924. In an aspect, the micro-impulse radar component 1920 includes at least one receiver 2100. In an aspect, receiver 2100 includes at least one adjustable range gate 2110. In an aspect, the micro-impulse radar component 1920 includes a monostatic micro-impulse radar 2120. In an aspect, the monostatic micro-impulse radar 2120 includes a transmitter and a receiver that are collocated. In an aspect, the micro-impulse radar component 1920 includes a bistatic micro-impulse radar 2130. In an aspect, the bistatic micro-impulse radar 2130 includes a transmitter and a receiver that are not collocated. In an aspect, the micro-impulse radar component 1920 includes a multistatic micro-impulse radar component. In an aspect, the multistatic micro-impulse radar component includes multiple spatially diverse monostatic radar or bistatic radar components with a shared area of coverage. In an aspect, the micro-impulse radar component 1920 includes a fixed beam angle 2140. In an aspect, the micro-impulse radar component 1920 includes a variable beam angle. 2150. In an aspect, circuitry 1970 includes beam width control circuitry configured to adjust a beam width of the micro-impulse radar component. In an aspect, the micro-impulse radar circuitry 1974 includes circuitry configured to adjust a beam width of the micro-impulse radar component. In an aspect, the micro-impulse radar component 1920 includes adjustable output power 2160. In an aspect, circuitry 1970 includes output power control circuitry configured to adjust an output power of the micro-impulse radar component. In an aspect, the micro-impulse radar circuitry 1974 includes circuitry configured to adjust an output power of the micro-impulse radar component. Non-limiting aspects of a micro-impulse radar component have been described above herein.

Figure 22:
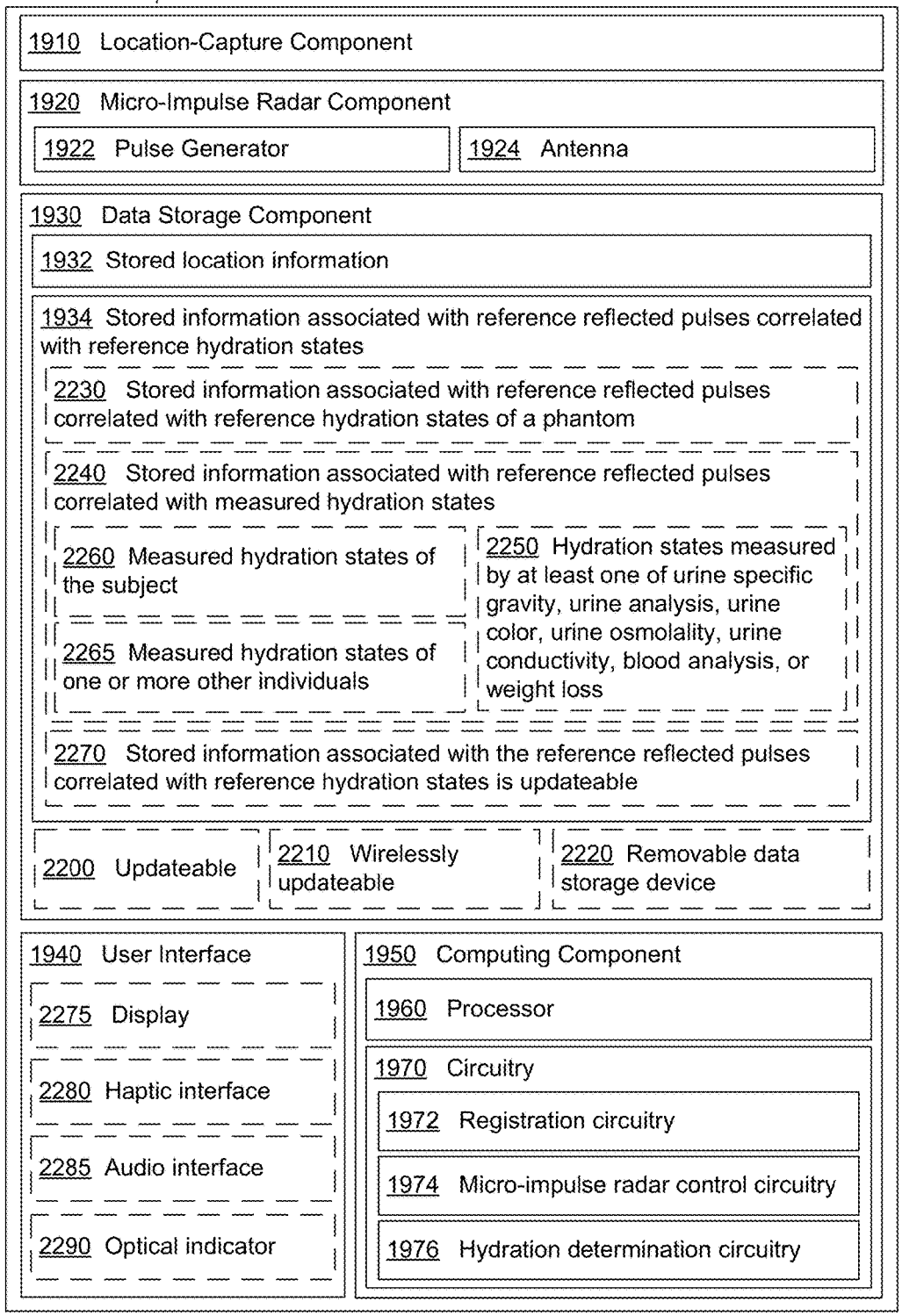
FIG. 22 is a block diagram illustrating aspects of a hand-held hydration monitor including a location-capture component such as shown in FIG. 19.

FIG. 22 illustrates further aspects of a hand-held hydration monitor including a location-capture component. Hand-held-hydration monitor 1900 includes data storage component 1930 including stored location information 1932 and stored information 1934 associated with reference reflected pulses correlated with reference hydration states. In an aspect, data storage component 1930 is updateable 2200. For example, the data storage component can be updated as new information (e.g., location information and/or hydration information) becomes available. In an aspect, data storage component 1930 is wirelessly updateable 2210. For example, updates to the stored location information 1932 and/or stored information 1934 associated with reference reflected pulses correlated with reference hydration states can be wirelessly transmitted to the data storage component through a transmission unit associated with the hand-held hydration monitor. In an aspect, the data storage component includes a non-volatile data storage component. In an aspect, the data storage component includes a recordable data storage component. In an aspect, the data storage component includes a mass storage device. In an aspect, the data storage component is operably coupled to a central processing unit of the computing component through input/output channels. In an aspect, the data storage component includes data storage media. In an aspect, the data storage component is included in a hard drive of the computing component.

In an aspect, the data storage component 1930 is removable. In an aspect, the data storage component 1930 includes a removable data storage device 2220. In an aspect, the data storage component includes a removable memory card or stick. Non-limiting examples of removable data storage include flash memory cards, Memory Sticks, mass storage devices, CompactFlash, non-volatile memory cards, Secure Digital™ (SD) cards, miniSD cards, microSD cards, USB flash drive, or XQD cards. Additional non-limiting aspects of a data storage component have been described above herein.

Data storage component 1930 includes stored location information 1932. In an aspect, stored location information 1932 includes one or more stored images (e.g., one or more stored images of a location on a subject). In an aspect, stored location information 1932 includes one or more stored fiducials (e.g., a pattern of physical landmarks associated with the location on the subject or a pattern of fiducial markers placed on or worn over the location on the subject). Non-limiting aspects of stored location information have been described above herein.

Data storage component 1930 includes stored information 1934 associated with reference reflected pulses correlated with reference hydration states. In an aspect, the stored information 1934 associated with reference reflected pulses correlated with reference hydration states includes stored information 2230 associated with reference reflected pulses correlated with reference hydration states of a phantom. In an aspect, the stored information 1934 associated with reference reflected pulses correlated with reference hydration states includes stored information 2240 associated with reference reflected pulses correlated with measured hydration states. For example, one or more reference reflected pulses can be correlated with a measured parameter of hydration. For example, the signal properties, e.g., frequency and/or amplitude, of one or more reference reflected pulses can be correlated with at least one measured parameter of hydration. In an aspect, the measured hydration states include hydration states measured by at least one of urine specific gravity, urine analysis, urine color, urine osmolality, urine conductivity, blood analysis, or weight loss, as illustrated in block 2250. In an aspect, the measured hydration states include measured hydration states of a subject 2260. For example, the one or more measured hydration states of the subject can include hydration states measured by at least one of urine specific gravity, urine analyses, urine color, urine osmolality, urine conductivity, blood analysis, or weight loss. In an aspect, the measured hydration states include measured hydration states of one or more other individuals 2265. For example, the measured hydration states can include an average of measured hydration states of one or more other individuals. For example, the measured hydration states can include measured hydration states from a normalized population matched to the subject, e.g., matched by age, gender, activity level, medical status, and the like. In an aspect, the stored information associated with reference reflected pulses correlated with the reference hydration states is updateable, as illustrated in block 2270.

The hand-held hydration monitor 1900 includes user interface 1940. In an aspect, user interface 1940 is operably coupled to computing component 1950. In an aspect user interface 1940 includes one or more input components and/or output components for use by a user to interface with the hand-held hydration monitor. The one or more input components can be used to enter information into the hand-held hydration monitor, e.g., subject identifiers and/or information, operating instructions, measurement parameters, and the like, and may be integrated into the hand-held hydration monitor or may be one or more peripheral devices operably connected through a wired or wireless connection to the hand-held hydration monitor. Non-limiting examples of input components have been described above herein.

In an aspect, user interface 1940 includes one or more output components over which processed information is transmitted, e.g., viewed, as output results and may be integrated into the hand-held hydration monitor or may be one or more peripheral devices operably connected through a wired or wireless connection to the hand-held hydration monitor. For example, the user interface may be used to alert a user that registration has or has not been satisfied. For example, the user interface may be used to provide instructions to a user. For example, the user interface may be used to report to a user a relative hydration state of the tissue associated with the location on the subject. Non-limiting examples of output components include but are not limited to displays, e.g., liquid crystal displays, audio speakers, and the like.

In an aspect, the user interface 1940 includes a display 2275. For example, the user interface can include a liquid crystal display. In an aspect, the user interface 1940 includes a haptic interface 2280. For example, the user interface can include a vibrating component. In an aspect, user interface 1940 includes an audio interface 2285. For example, the user interface can include a microphone, a speaker, and an audio signal processor. In an aspect, the user interface 1940 includes at least one optical indicator 2290. For example, the at least one optical indicator can include at least one light-emitting diode, e.g., at least one red or green light-emitting diode. Non-limiting examples of user interfaces have been described above herein.

Hand-held hydration monitor 1900 includes computing component 1950 including processor 1960 and circuitry 1970. Non-limiting aspects of a computing component have been described above herein. Computing component 1950 includes circuitry 1970 including registration circuitry 1972 configured to compare the captured information associated with the location on the subject with the stored location information to determine a registration value; micro-impulse radar control circuitry 1974 configured to actuate the micro-impulse radar component; and hydration determination circuitry 1976 configured to receive information associated with one or more reflected pulses from a tissue associated with the location on the subject and to compare the information associated with the one or more reflected pulses from the tissue with the stored information associated with the reference reflected pulses correlated with the reference hydration states to determine a relative hydration state of the tissue.

In an aspect, computing component 1950 includes circuitry configured to execute one or more instructions. In an aspect, computing component 1950 includes circuitry configured to execute one or more instructions for comparing the captured information associated with the location on the subject with the stored location information; one or more instructions for determining a registration value; one or more instructions for actuating the micro-impulse radar component; one or more instructions for receiving the information associated with the one or more reflected pulses from a tissue associated with the location on the subject; one or more instructions for comparing the information associated with the one or more reflected pulses from the tissue with the stored information associated with the reference reflected pulses correlated with the reference hydration states to determine a relative hydration state of the tissue.

Figure 23:
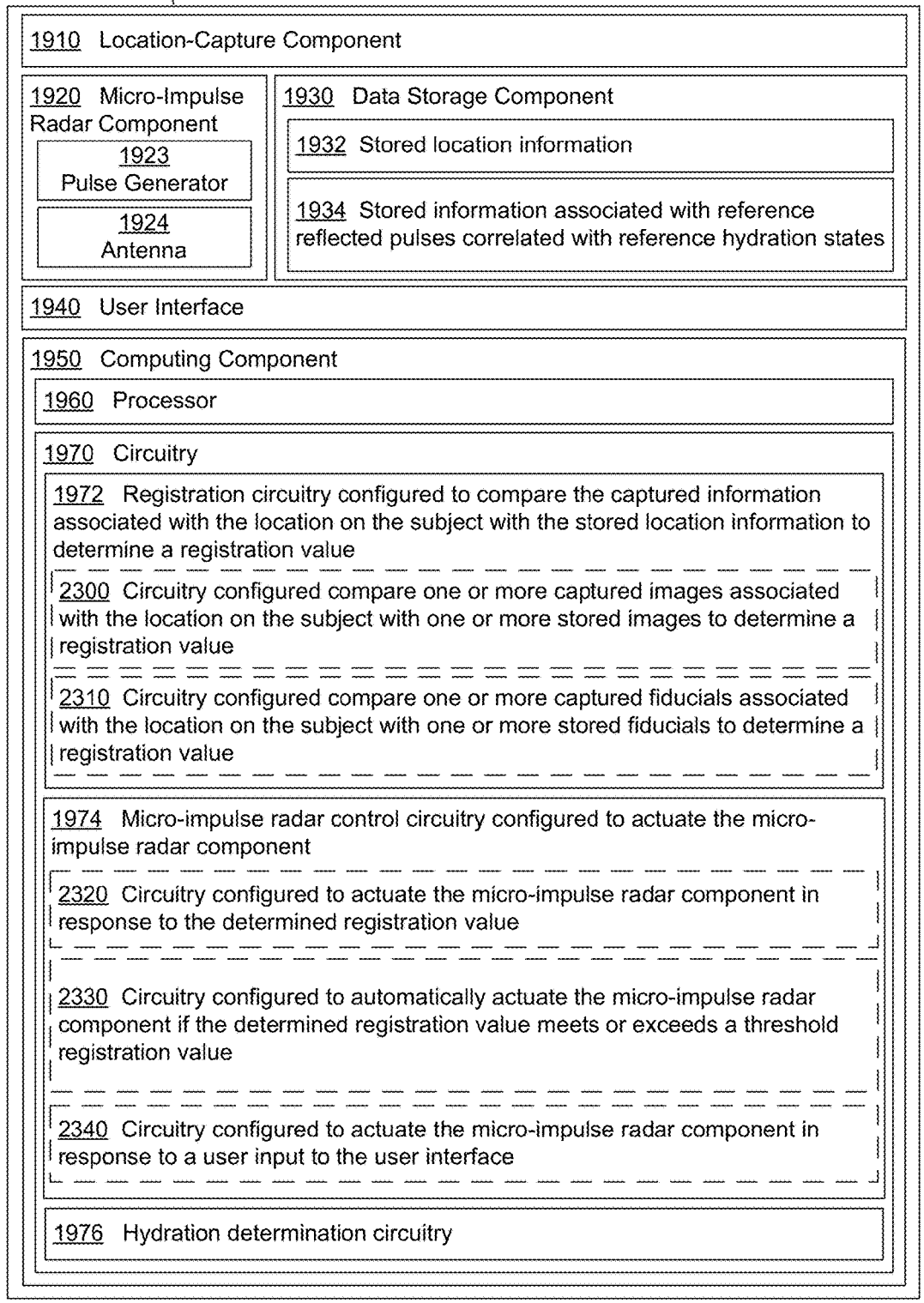
FIG. 23 is a block diagram showing aspects of a hand-held hydration monitor including a location-capture component such as depicted in FIG. 19.

FIG. 23 illustrates further aspects of a hand-held hydration monitor including a location-capture component. Hand-held hydration monitor 1900 includes registration circuitry 1972 configured to compare the captured information associated with the location on the subject with the stored location information to determine a registration value. In an aspect, the registration value indicates that the captured information associated with the location on the subject registers with the stored location information. In an aspect, the registration value indicates that the captured information associated with the location on the subject does not register with the stored location information. In an aspect, registration circuitry 1972 includes circuitry 2300 configured to compare one or more captured images associated with the location on the subject with one or more stored images to determine a registration value. For example, the registration circuitry can be configured to compare an image of a subject's torso with stored images of torsos to determine a registration value, e.g., to determine if an image of the subject's torso is included in the stored location information. In an aspect, registration circuitry 1972 includes circuitry 2310 configured to compare one or more captured fiducials associated with the location on the subject with one or more stored fiducials to determine a registration value. For example, the registration circuitry can be configured to compare a pattern of fiducials, e.g., a pattern of fiducial markers associated with a garment worn by the subject, with stored patterns of fiducial markers to determine a registration value.

In an aspect, the registration circuitry includes circuitry configured to compare the captured information associated with the location on the subject with the stored location information to determine a registration value using a registration or alignment algorithm. In an aspect, the registration circuitry includes circuitry configured to compare one or more captured images associated with the location on the subject with one or more stored images to determine a registration value using a registration or alignment algorithm. In an aspect, the registration circuitry includes circuitry configured to compare the captured fiducials, e.g., physical landmarks or fiducial markers, associated with the location on the subject with stored fiducial information to determine a registration value using a registration or alignment algorithm. In an aspect, the registration circuitry includes circuitry configured to register one or more physical landmarks in the one or more captured images of the location on the subject with landmarks in the one or more stored images. For example, a registration algorithm can be used to detect features (e.g., physical landmarks) depicted in the captured one or more images of the location on the subject and match these features with features in the stored one or more images. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. In an aspect, the registration circuitry includes circuitry configured to match the features detected in the captured one or more images of the location on the subject with features in the one or more stored images using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser *Image Vision Computing* (2003) 21:977-1000.

In an aspect, micro-impulse radar control circuitry 1974 includes circuitry 2320 configured to actuate the micro-impulse component 1920 in response to the determined registration value. In an aspect, micro-impulse radar control circuitry 1974 includes circuitry configured to automatically actuate (or to authorize the activation of) the micro-impulse radar component 1920 if the determined registration value indicates that the captured information associated with the location on the subject registers with the stored location information. In an aspect, micro-impulse radar control circuitry 1974 includes circuitry 2330 configured to automatically actuate the micro-impulse radar component if the determined registration value meets or exceeds a threshold registration value. For example, the threshold registration value can include a percent registration (e.g., 0% to 100% registration). For example, the micro-impulse radar component may be activated once the registration value meets or exceeds a threshold registration value, e.g., 90% registration. In some embodiments, the micro-impulse radar control circuitry 1974 includes circuitry configured to block actuation of the micro-impulse radar component if the determined registration value indicates that the captured information associated with the location on the subject does not register with the stored location information. In an aspect, the micro-impulse radar control circuitry includes circuitry configured to block actuation of the micro-impulse radar component if the determined registration value fails to meet or exceed a threshold registration value. For example, the hand-held hydration monitor can be configured to prevent scanning of the subject until the appropriate scanning location on the subject is detected.

In an aspect, micro-impulse radar control circuitry 1974 includes circuitry 2340 configured to actuate the micro-impulse radar component 1920 in response to a user input to the user interface 1940. For example, a user may push an actuation button to actuate the micro-impulse radar component. For example, the user may push an actuation button in response to receiving an alert message indicating that the captured information associated with the location on the subject registers with the stored location information. In an aspect, the actuation button is locked if the determined registration value fails to meet or exceed the threshold registration value. In an aspect, the actuation button is unlocked if the determined registration value meets or exceeds the threshold registration value.

Figure 24:
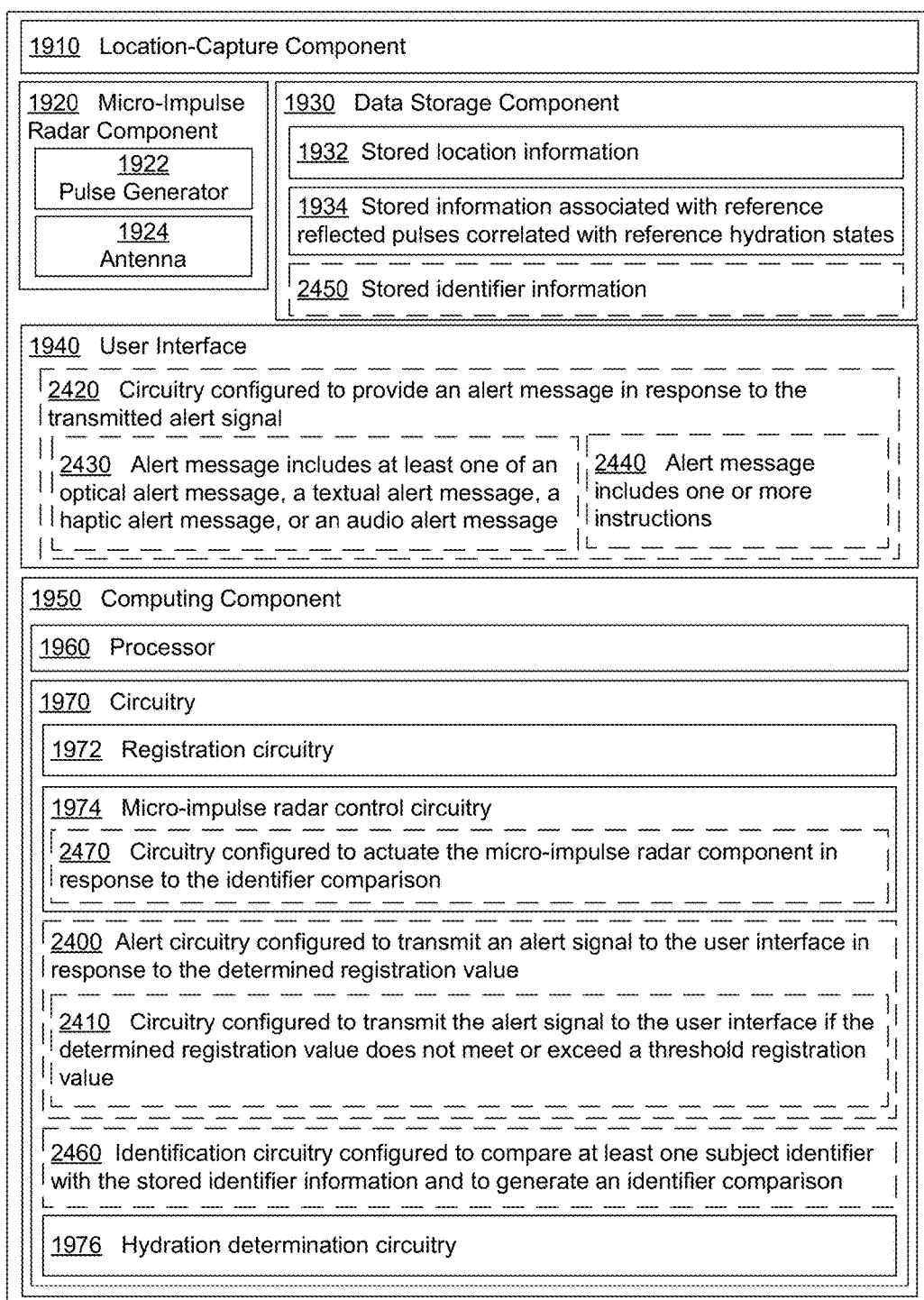
FIG. 24 is a block diagram depicting aspects of a hand-held hydration monitor including a location-capture component such as illustrated in FIG. 19.

FIG. 24 illustrates further aspects of a hand-held hydration monitor including a location-capture component. In an aspect, computing component 1950 of hand-held hydration monitor 1900 includes alert circuitry 2400 configured to transmit an alert signal to the user interface 1940 in response to the determined registration value. In an aspect, alert circuitry 2400 includes circuitry 2410 configured to transmit an alert signal to the user interface 1940 if the determined registration value does not meet or exceed a threshold registration value. For example, an alert signal can be transmitted to the user interface if the determined registration value indicates that the captured information associated with the location on the subject does not register with the stored location information. In an aspect, the user interface 1940 includes circuitry 2420 configured to provide an alert message in response to the transmitted alert signal. In an aspect, the alert message indicates that the captured information associated with the location on the subject does not register with the stored location information. In an aspect, the alert message indicates that the determined registration value fails to meet or exceed the threshold registration value.

In some embodiments, the alert circuitry includes circuitry configured to transmit an alert signal to the user interface if the determined registration value does meet or exceed the threshold registration value. In some embodiments, the alert circuitry includes circuitry configured to transmit an alert signal to the user interface if the determined registration value indicates that the captured information associated with the location on the subject registers with the stored location information. In an aspect, the transmitted alert signal indicates that the captured information associated with the location on the subject registers with the stored location information. In an aspect, the user interface includes circuitry configured to provide an alert message in response to the transmitted alert signal. In an aspect, the alert message indicates that the captured information associated with the location on the subject registers with the stored location information.

In an aspect, the alert message includes at least one of an optical alert message, a textual alert message, a haptic alert message, or an audio alert message, as shown in block 2430. For example, the alert circuitry can transmit an alert signal to the user interface in response to a failure to meet or exceed the threshold registration value (e.g., the captured information associated with the location on the subject fails to register with the stored location information); the user interface providing an alert message, e.g., a red light, indicating to the user that registration has not been achieved. For example, the alert circuitry can transmit an alert signal to the user interface in response meeting or exceeding the threshold registration value (e.g., the captured information associated with the location of the subject registers with the stored location information); the user interface providing an alert message, e.g., a green light, indicating that registration has been achieved. For example, the user interface can provide an optical alert message, e.g., a green light versus a red light. For example, the user interface can provide a textual alert message, e.g., "registered" versus "not registered." For example, the user interface can provide a haptic alert message, e.g., a vibration versus no vibration. For example, the user interface can provide an audio alert message, e.g., "registered" versus "not registered." In an aspect, the micro-impulse radar control circuitry is configured to actuate the micro-impulse radar component in response to a user input to the user interface in response to an alert message. For example, a user may push an actuation button in response to receiving a green light alert message or a "registered" textual or audio alert message. For example, a user may adjust the position of the hand-held hydration monitor in response to receiving a red light alert message or a "not registered" textual or audio alert message so as to adjust where on the subject the location-capture component captures location information.

In an aspect, the alert message includes one or more instructions 2440. In an aspect, the alert message includes one or more textual or audio instructions. For example, the alert message can include one or more textual or audio instructions for a user. For example, the alert message can include one or more textual or audio instructions instructing the user to move at least one of right, left, back, or forward to adjust where on the subject the location-capture component captures location information. For example, the alert message can include one or more textual or audio instructions instructing the user to push an actuation button to initiate actuation of the micro-impulse radar component. In an aspect, the alert message can include one or more instructions for adjusting a component of the hand-held hydration monitor. For example, the alert message can include one or more instructions for adjusting a output power, a beam width, a pulse frequency, or other aspects of the hand-held hydration monitor.

In an aspect, the hand-held hydration monitor 1900 further includes one or more instructions for treating dehydration. The one or more instructions might include sipping a small amount of water, drinking carbohydrate/electrolyte containing drinks (e.g., Gatorade or Pedialyte), sucking popsicles made from juices or sports drinks, or sucking ice chips. In some instances, if the dehydration symptoms are particularly severe, e.g., elevated resting heart rate and low blood pressure, intravenous fluids may be recommended. The one or more instructions might also include instructions for cooling the person if the dehydration is due to excessive heat exposure or elevated body temperature. The one or more instructions might include removing excess clothing and/or loosening clothing, moving to an air conditioned area, moving in proximity to a fan or into the shade, using a spray bottle or mister to spray lukewarm water on exposed skin surfaces to help with cooling by evaporation.

In some embodiments, one or more functionalities of the hand-held hydration monitor are dependent upon the identification of the subject. For example, the hand-held hydration monitor may include controls that only allow scanning of subjects who are included in a database of allowed subjects. In an aspect, the data storage component 1930 includes stored identifier information 2450. In an aspect, stored identifier information includes at least one subject identifier for one or more subjects. In an aspect, the stored identifier information includes names, ages, telephone numbers, social security numbers, or identification numbers for one or more subjects. In an aspect, the stored identifier information includes one or more biometric parameters for one or more subjects. Non-limiting examples of biometric parameters include fingerprints, facial recognition, voice recognition, retinal scan, DNA, or other biometric features of a subject. In an aspect, the stored identifier information includes one or more images of the subject. In an aspect, the stored identifier information includes one or more fiducials, e.g., a pattern of physical landmarks or a pattern of fiducial markers, associated with the subject.

In an aspect, hand-held hydration monitor 1900 includes identification circuitry 2460 configured to compare at least one subject identifier with the stored identifier information and to generate an identifier comparison. In an aspect, the at least one subject identifier includes at least one of name, age, telephone number, social security number, or identification number. In an aspect, the at least one subject identifier includes at least one biometric parameter, e.g., fingerprints, facial recognition, voice recognition, retinal scan, DNA, or other biometric feature of the subject. In an aspect, the at least one subject identifier includes one or more captured images of a location on the subject. In an aspect, the at least one subject identifier includes a pattern of fiducials associated with the location on the subject. In an aspect, the at least one subject identifier is entered into the hand-held hydration monitor using the user interface. For example, an identification number or code can be entered into a keypad of the hand-held hydration monitor. In an aspect, the at least one subject identifier is entered into the hand-held hydration monitor wirelessly. In an aspect, the at least one subject identifier is measured by the hand-held hydration monitor. For example, the hand-held hydration monitor can include a fingerprint scanner. For example, the hand-held hydration monitor can include an image-capture device and facial recognition software. For example, the hand-held hydration monitor can include a microphone and voice recognition software. For example, the location-capture component can capture at least one subject identifier, e.g., at least one image of a location on the subject.

In an aspect, the reported identifier comparison is reported to the micro-impulse radar control circuitry. In an aspect, the micro-impulse radar control circuitry 1974 includes circuitry 2470 configured to actuate (or to authorize the activation of) the micro-impulse radar component in response to the identifier comparison. For example, the micro-impulse radar control circuitry can be configured to automatically actuate the micro-impulse radar component upon receipt of an identifier comparison that confirms the identity of the subject. For example, the micro-impulse radar control circuitry can be configured to prevent actuation of the micro-impulse radar component upon receipt of an identifier comparison that cannot confirm the identity of the subject. In an aspect, the reported identifier comparison is reported to alert circuitry 2400. In an aspect, the alert circuitry 2400 is configured to generate an alert signal in response to the identifier comparison. For example, the alert circuitry can be configured to generate an alert signal that is transmitted to the user interface upon receipt of an identifier comparison that fails to confirm the identity of the subject. For example, the user interface can generate an alert message indicating failed subject identification. For example, the alert circuitry can be configured to generate an alert signal that is transmitted to the user interface upon receipt of an identifier comparison that confirms the identity of the subject. For example, the user interface can generate an alert message indicating successful subject identification.

Figure 25:
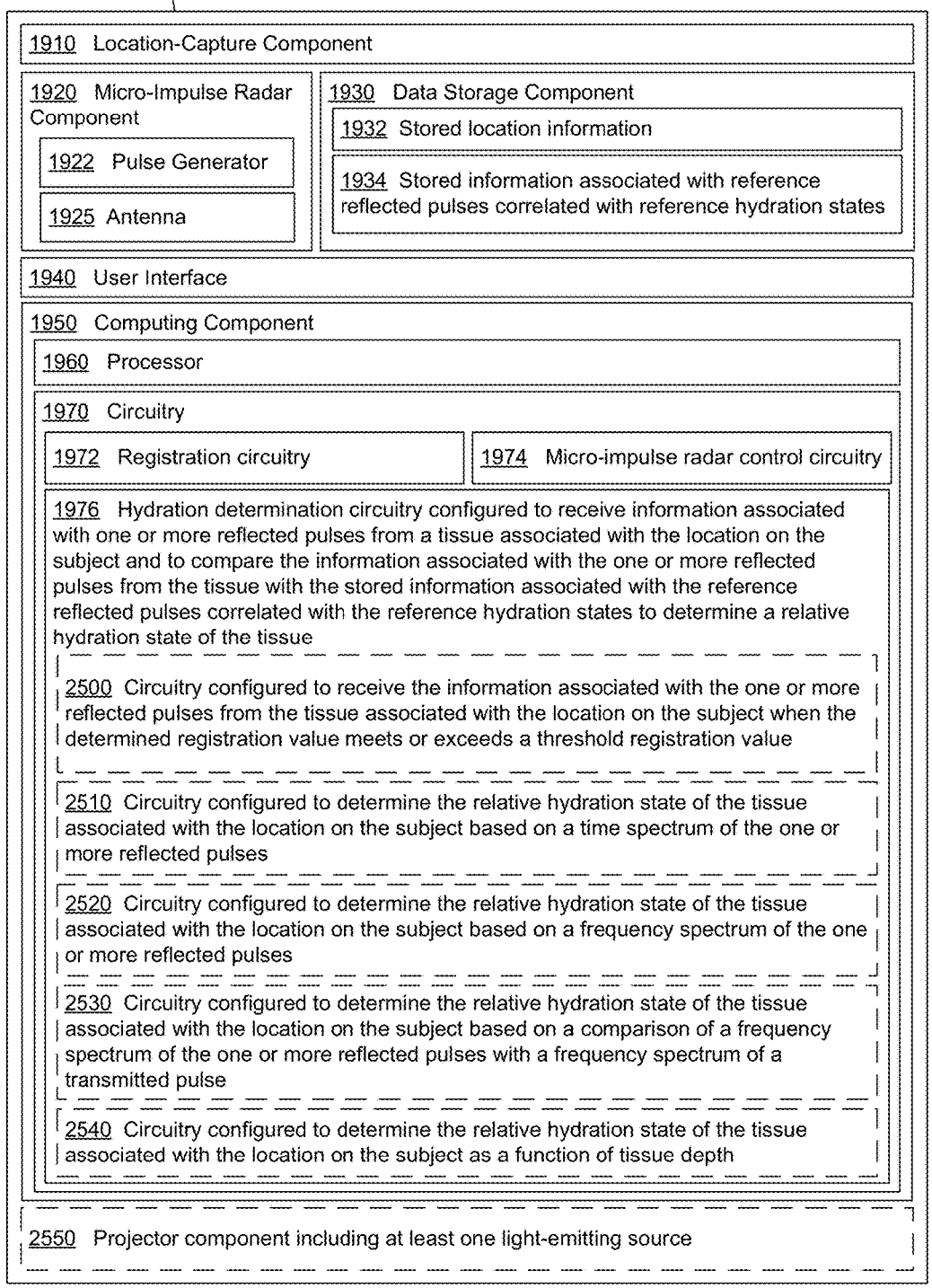
FIG. 25 is a block diagram illustrating aspects of a hand-held hydration monitor including a location-capture component such as shown in FIG. 19.

FIG. 25 illustrates further aspects of a hand-held hydration monitor including a location-capture component. Hand-held hydration monitor 1900 includes hydration determination circuitry 1976 configured to receive information associated with one or more reflected pulses from a tissue associated with the location on the subject and to compare the information associated with the one or more reflected pulses from the tissue with the stored information associated with the reference reflected pulses correlated with the reference hydration states to determine a relative hydration state of the tissue. In an aspect, hydration determination circuitry 1976 includes circuitry 2500 configured to receive the information associated with the one or more reflected pulses from the tissue associated with the location on the subject when the determined registration value meets or exceeds a threshold registration value. For example, the hydration determination circuitry can include circuitry configured to only receive information associated with the one or more reflected pulses from the tissue associated with the location on the subject when the determined registration value indicates that the captured information associated with the location on the subject registers with the stored location information. In an aspect, the hydration determination circuitry includes circuitry to block receipt (or block processing, storing, or reporting) of the one or more reflected pulses from the tissue associated with the location on the subject when the determined registration value indicates that the captured information associated with the location on the subject does not register with the stored location information.

In an aspect, the data storage component 1930 is configured to store the determined relative hydration state. In an aspect, the data storage component includes stored information associated with the determined relative hydration state of the tissue. In an aspect, the data storage component includes stored information associated with the determined relative hydration state of the tissue linked to at least on subject identifier. In an aspect, the data storage component includes stored information associated with the determined relative hydration state of the tissue linked to the captured information associated with the location on the subject.

In an aspect, hydration determination circuitry 1976 includes circuitry 2510 configured to determine the relative hydration state of the tissue associated with the location on the subject based on a time spectrum of the one or more reflected pulses. In an aspect, hydration determination circuitry 1976 includes circuitry 2520 configured to determine the relative hydration state of the tissue associated with the location on the subject based on a frequency spectrum of the one or more reflected pulses. In an aspect, hydration determination circuitry 1976 includes circuitry 2530 configured to determine the relative hydration state of the tissue associated with the location on the subject based on a comparison of a frequency spectrum of the one or more reflected pulses with a frequency spectrum of a transmitted pulse. In an aspect, hydration determination circuitry 1976 includes circuitry 2540 configured to determine the relative hydration state of the tissue associated with the location on the subject as a function of tissue depth.

In some embodiments, hand-held hydration monitor 1900 includes projector component 2550 including at least one light-emitting source. In an aspect, the projector component is configured to project a tracer on the location on the subject. In an aspect, the tracer corresponds to a beam width of one or more transmitted pulses from the micro-impulse radar component. For example, the tracer can include a circle of light projected on the location on the subject to indicate how much of the location will be covered by the one or more transmitted pulses. In an aspect, the tracer projected on to the subject indicates where the transmitted one or more pulses will converge with the subject. In an aspect, the tracer is a center point of the transmitted one or more pulses. In an aspect, the tracer is positioned on a central point of the intended target location on the subject. In an aspect, the tracer includes at least one of a dot, a circle, a ring, a border, lines, or concentric rings. Non-limiting aspects of a projector and at least one light-emitting source have been described above herein.

Described herein are methods for using a hydration monitor, e.g., a hand-held hydration monitor such as described above herein, to determine a hydration state of a subject. FIG. 26 illustrates a flowchart of an embodiment of a method for determining a hydration state with a hydration monitor. Method 2600 includes receiving information associated with at least one first reflected pulse from a nearest surface of a target tissue of a subject with the hydration monitor, the hydration monitor including a micro-impulse radar component, a data storage component including stored information associated with reference reflected pulses correlated with reference hydration states, a user interface, and a computing component including a processor and circuitry, as shown in block 2610; determining a distance from the hydration monitor to the subject using the information associated with the at least one first reflected pulse from the nearest surface of the target tissue of the subject, as shown in block 2620; actuating the micro-impulse radar component to transmit one or more pulses to the target tissue of the subject, as shown in block 2630; receiving information associated with one or more reflected pulses from the target tissue of the subject, as shown in block 2640; and comparing the received information associated with the one or more reflected pulses from the target tissue of the subject with the stored information associated with the reference reflected pulses correlated with reference hydration states to determine a relative hydration state of the target tissue of the subject, as shown in block 2650. In an aspect, some or all of the steps of method 2600 are performed by circuitry (e.g., logic circuitry) in cooperation with other components of the monitor.

FIG. 27 shows a flowchart illustrating further aspects of a method of determining a hydration state using a hydration monitor such as shown in FIG. 26. Method 2700 includes in block 2705 receiving information associated with at least one first reflected pulse. For example, the hydration monitor transmits one or more pulses from a pulse generator towards a target tissue of the subject and receives signals associated with one or more reflected pulses with at least one antenna. The at least one first reflected pulse is from the nearest surface of a target tissue of a subject. In an aspect, the first reflected pulse represents a first return signal from a first transmitted pulse directed at and reflected off of a nearest surface of the subject.

Method 2700 includes in block 2710 determining a distance from the monitor to the subject. In an aspect, the method includes determining the distance from the hydration monitor to the subject using the information associated with the at least one first reflected pulse from the nearest surface of the target tissue of the subject. For example, the hydration monitor includes circuitry, e.g., an algorithm, configured to determine the distance from the hydration monitor to the subject based on the time required for a pulse to travel to and from the subject. In an aspect, the distance is determined by measuring the time required for a pulse to leave the hydration monitor through the transmitter, reflect off the subject, and return to the receiver. In air, for example, a pulse of electromagnetic energy is expected to travel at the speed of light (e.g., ~$3\times10^8$ meters/second). As such, the distance can be determined by dividing by two the time a pulse takes to travel round trip between the monitor and the subject and multiplying by the speed of light. For example, a measured round trip travel time of about 1 nanosecond would equate with a distance of about 0.15 meters.

In an aspect, the method includes adjusting an output power of the micro-impulse radar component in response to the determined distance. In an aspect, the method includes transmitting ultra-wideband pulses of sufficient energy so that the reflected pulses are detectable by the receiver. In an aspect, the amount of energy delivered to the target location on the subject is inversely proportional to the square of the determined distance between the hydration monitor (i.e., the energy transmitter) and the target location on the subject. For example, the intensity of the ultra-wideband pulses radiating from the micro-impulse radar component (power per unit area perpendicular to the source) is inversely proportional to the square of the distance between the hydration monitor and the target location on the subject. In an aspect, the method includes adjusting the output power of the micro-impulse radar component upward as the determined distance between the hydration monitor and the target location on the subject increases. In an aspect, the method includes adjusting the output power downward as the determined distance between the hydration monitor and the target location on the subject decreases.

In an aspect, the method includes adjusting a beam angle of the micro-impulse radar component in response to the determined distance. In an aspect, the beam width of the transmitted pulse at the target tissue is dependent upon the beam angle and the distance between the hydration monitor and the target location on the subject. In an aspect, the method includes calculating an appropriate beam width to just cover the target tissue and adjusting the beam angle of the micro-impulse radar component based on the determined distance between the hydration monitor and the target location on the subject to achieve the calculated beam width.

In an aspect, the method includes determining a range of operating distances of the hydration monitor based on at least one of an output power or a beam angle of the micro-impulse radar component. In an aspect, the output power of the micro-impulse radar component reaching the target is inversely proportional to the square of the distance. In an aspect, the method includes determining a range of operating distances that provides sufficient energy to the target to be able to measure a return signal. In an aspect, the beam angle in combination with the distance dictates the beam width reaching the target location on the subject. In an aspect, the beam width increases proportionally with the distance at a fixed beam angle. In an aspect, the method includes determining a range of operating distances for a hydration monitor with a fixed beam angle to generate a range of acceptable beam widths at the target location.

In an aspect, method 2700 includes an "in range?" determination point 2715. In an aspect, the method includes determining whether the determined distance is within a range of predetermined operating distances of the hydration monitor. For example, the range of predetermined operating distances of the hydration monitor may include a range from about a few centimeters to about fifty meters. In an aspect, the range of predetermined operating distances of the hydration monitor is dependent upon the output power and/or the beam angle of the micro-impulse radar component. In an aspect, method 2700 includes transmitting an alert signal (e.g., in block 2720) to the user interface of the hydration monitor in response to the determined distance. For example, the method can include transmitting an alert signal to the user interface which includes information associated with the distance from the hydration monitor to the subject. For example, the method can include transmitting an alert signal to the user interface of the hydration monitor indicating that the subject is within the range of predetermined operating distances of the hydration monitor. For example, the method can include transmitting an alert signal to the user interface of the hydration monitor indicating that the subject is not within the range of predetermined operating distances of the hydration monitor.

Method 2700 includes actuating the micro-impulse radar component, as shown in block 2725. The method includes actuating the micro-impulse radar component to transmit one or more pulses to the target tissue of the subject. In some embodiments, the method includes actuating the micro-impulse radar component in response to the determined distance. In some embodiments, the method includes automatically actuating the micro-impulse radar component to transmit the one or more pulses to the target tissue of the subject in response to the determined distance if the determined distance is within a range of predetermined operating distances of the hydration monitor. For example, the method can include a determination point, e.g., "in range" determination point 2715, which when satisfied, allows the micro-impulse radar component to be actuated. In some embodiments, the method includes preventing the actuation of the micro-impulse radar component in response to the determined distance if the determined distance is not within a range of predetermined operating distances of the hydration monitor. For example, if the "in range" determination is not satisfied (e.g., the determined distance is not in range), the method can include blocking actuation signals from the micro-impulse radar control circuitry of the hydration monitor to prevent actuation of the micro-impulse radar component.

In some embodiments, the method includes actuating the micro-impulse radar component to transmit one or more pulses to the target tissue of the subject in response to a user input to the user interface. For example, the method can include a user input to a user interface, as shown in block 2730, to actuate the micro-impulse radar component. For example, the method can include actuating the micro-impulse radar component in response to a user pushing an actuation button on the hydration monitor. For example, the method can include actuating the micro-impulse radar component in response to a user's audio command. In some embodiments, the user actuates the micro-impulse radar component in response to receiving an alert message indicating the distance between the hydration monitor and the subject. For example, a text message on the display of the hydration monitor may indicate a distance of 5 meters, a distance that the user knows is within the range of predetermined operating distances of the hydration monitor.

In an aspect, the method includes transmitting an alert signal to the user interface of the hydration monitor if the determined distance is not within the range of predetermined operating distances of the hydration monitor. In an aspect, method 2700 includes transmitting an alert signal, as shown in block 2720, in response to not satisfying the "in range" determination. In an aspect, method 2700 includes generating an alert message in response to the transmitted alert signal, as shown in block 2735. In an aspect, the alert message includes at least one of an optical alert message, a textual alert message, an audible alert message, or a haptic alert message.

In an aspect, method 2700 includes providing user instructions, as shown in block 2740. For example, the method can include providing user instructions through the user interface. In some embodiments, the method includes providing user instructions through the user interface if the determined distance is not within a range of predetermined operating distances for the hydration monitor. For example, if the determined distance does not satisfy the "in range" determination, the method can include providing user instructions. In an aspect, the method includes providing instructions to move the hydration monitor and/or the subject (e.g., up, down, right, left, forward, and/or back) to a distance that is within the range of predetermined operating distances of the hydration monitor.

In an aspect, method 2700 includes comparing at least one subject identifier with identifier information, as shown in block 2745, and generating an identifier comparison, as shown in block 2750. In an aspect, the method includes comparing at least one subject identifier with identifier information stored in the data storage component of the hydration monitor and generating an identifier comparison. In an aspect, the method includes entering the at least one subject identifier into the hydration monitor through the user interface. In an aspect, the method includes receiving the at least one subject identifier through the user interface. For example, at least one subject identifier (e.g., a name or identification number) can be entered into the hydration monitor through the user interface. For example, the at least one subject identifier can be received wirelessly, e.g., through a radiofrequency transmission. In an aspect, method 2700 includes comparing a subject identifier with identifier information, as shown in block 2745. For example, the method can include comparing a subject's name, phone number, social security number, identification code, or other identifier with like identifier information stored in the data storage component. For example, the method can include comparing a biometric parameter of a subject, e.g., fingerprint, voice scan, retinal scan, DNA scan, or other biometric parameter with like biometric parameters stored in the data storage component. As a result of the comparison, method 2700 includes generating an identifier comparison, as shown in block 2750. In an aspect, the method includes actuating the micro-impulse radar component in response to the identifier comparison. For example, if the identifier comparison indicates a substantial identity between the subject and identifier information in the data storage component, the method includes actuating the micro-impulse radar component.

In an aspect, the method includes transmitting an alert signal to the user interface in response to the identifier comparison. In an aspect, the alert signal can indicate whether or not the identifier comparison meets or exceeds a threshold of identity between at least one subject identifier and the stored identifier information. For example, the alert signal may indicate to a user that the identifier comparison meets a threshold of identity, leading a user to actuate the micro-impulse radar component through a user input to the user interface (block 2730). For example, if the identifier comparison indicates a lack of identity between the at least one subject identifier and the identifier information in the data storage component, the method can include transmitting an alert signal (as shown in block 2755) to the user interface.

Method 2700 receiving information associated with one or more reflected pulses (block 2760) from the target tissue of the subject. In an aspect, the method includes receiving reflected pulses from the target tissue of the subject with at least one receive antenna associated with the hydration monitor and processing the received reflected pulses with a signal processor. In an aspect, the method includes receiving processed signals from a signal processor of the micro-impulse radar component of the hydration monitor. In an aspect, the method includes receiving information associated with the one or more reflected pulses from the micro-impulse radar component of the hydration monitor.

In an aspect, method 2700 includes evaluating the quality of the received information associated with the one or more reflected pulses from the target tissue of the subject against a quality threshold, as shown in block 2765. In an aspect, the quality threshold can include a signal-to-noise threshold. In an aspect, the quality threshold can include a "reasonability" threshold. For example, is the received information associated with the one or more reflected pulses reasonable (e.g., in terms of amplitude, frequency, and the like), for the measuring conditions. If the quality threshold indicates that the received information associated with the one or more reflected pulses is "good", then the comparison of the received information with the stored information can proceed (block 2770). If the quality threshold indicates that the received information associated with the one or more reflected pulses is "bad", then additional information is required. In an aspect, the method includes actuating the micro-impulse radar component to transmit one or more additional pulses to the target tissue of the subject if the evaluated quality of the received one or more reflected pulses fails to meet or exceed the quality threshold.

Method 2700 includes comparing the received information associated with the one or more reflected pulses with stored information to determine a relative hydration state, as shown in block 2770. The method includes comparing the received information associated with the one or more reflected pulses from the target tissue of the subject with the stored information associated with the reference reflected pulses correlated with the reference hydration states to determine a relative hydration state of the target tissue of the subject. In an aspect, the method includes comparing the received information associated with the one or more reflected pulses from the target tissue of the subject with the stored information associated with the reference reflected pulses correlated with the reference hydration states when the determined distance is within a range of predetermined operating distances of the hydration monitor. For example, the method can include only performing the comparison if the hydration monitor and the subject are at a distance within the operating range of the hydration monitor.

In an aspect, the method includes comparing the received information associated with the one or more reflected pulses from the target tissue of the subject with stored information associated with reference reflected pulses correlated with reference hydration states of a phantom. In an aspect, the method includes comparing the received information associated with the one or more reflected pulses from the target tissue of the subject with stored information associated with reference reflected pulses correlated with measured hydration states. For example, the measured hydration states can include hydration states of a subject and/or one or more other individuals measured through urine analysis, blood analysis, saliva analysis, weight loss/gain, or other means of measuring a hydration state.

In an aspect, the method includes comparing the received information associated with the one or more reflected pulses from the target tissue of the subject with the stored information associated with the reference reflected pulses correlated with the reference hydration states based on scaling to a reference distance. For example, the amplitude or signal strength of the one or more reflected pulses may vary according to the distance between the hand-held hydration monitor and the subject. For example, the amplitude or signal strength of one or more reflected pulses acquired from a given distance can be normalized against a signal pattern associated with one or more reflected pulses acquired at a reference difference. In an aspect, the method includes scaling the one or more reflected pulses relative to the reference distance. In an aspect, the method includes scaling the reference reflected pulses relative to the reference distance.

In an aspect, the method includes determining the relative hydration state of the target tissue of the subject based on a time spectrum of the one or more reflected pulses. For example, the method can include determining the relative hydration state of the target tissue of the subject based on comparing received signals from the one or more reflected pulses at specific time points relative to the stored reference information. For example, a signal peak at a particular time point on the time spectrum may change or shift (e.g., in amplitude or time) depending upon the hydration state.

In an aspect, the method includes determining the relative hydration state of the target tissue of the subject based on a frequency spectrum of the one or more reflected pulses. For example, the method can include determining the relative hydration state of the target tissue based on comparing received signals from the one or more reflected pulses at specific frequencies or frequency bands relative to the stored reference information. For example, a signal peak at a particular frequency or frequency band on the frequency spectrum may change or shift (e.g., in amplitude or frequency) depending upon the hydration state. For example, the method can include determining the relative hydration state of the target tissue based on dielectric properties of the tissue. For example, the behavior of electromagnetic waves is dependent on the physical dimensions and dielectric properties of the tissue. In turn, the dielectric properties of the tissue are frequency dependent. See, e.g., O'Halloran et al. (2006) "Frequency-Dependent Modeling of Ultra-Wide-Band Pulses in Human Tissue for Biomedical Applications," ISSC 2006, Dublin Institute of Technology, June 28-30, which is incorporated herein by reference.

In an aspect, the method includes determining the relative hydration state of the target tissue of the subject based on a comparison of a frequency spectrum of the one or more reflected pulses and a frequency spectrum of a transmitted pulse. For example, the method can include determining the relative hydration state of the target tissue by correlating changes in the frequency spectrum transmitted versus the frequency spectrum received under different hydration conditions of the tissue.

In an aspect, the method includes determining a relative hydration state of the target tissue of the subject as a function of tissue depth. For example, the method can include adjusting the range gate to collect reflected pulses at specific time points after transmission of a pulse relative to the depth of tissue being measured. In general, a transmitted pulse electromagnetic energy travels at the speed of light through air, but slows down upon entering the body. The reduction in speed is dependent upon the depth as well as the tissue type. For example, the speed through muscle is about seven times slower than through air. As a transmitted pulse penetrates a tissue, the magnitude of the pulse is attenuated exponentially. The amount of attenuation the signal suffers as it travels through the tissue depends on the dielectric properties of the tissue. For example, method can include determining the relative hydration state of the target tissue by correlating changes in the reflected pulses from specific tissue depths versus hydration conditions of the tissue.

In an aspect, method 2700 includes reporting the relative hydration state, as shown in block 2775. In an aspect, the method includes reporting the determined relative hydration state of the target tissue of the subject to a user through the user interface. For example, the method can include reporting the determined relative hydration state of the target tissue as a textual message on a display of the hydration monitor. In an aspect, the method includes reporting the determined relative hydration state of the target tissue of the subject relative to a reference hydration state of the subject. For example, the method can include reporting a relative hydration state at a current time point (e.g., during or after strenuous activity) relative to a hydration state measured at a prior time point (e.g., before initiating the strenuous activity). In an aspect, the method includes reporting the determined relative hydration state of the target tissue of the subject to a second computing component. In an aspect, the second computing component includes a personal electronic device, e.g., a smart phone, a tablet, or other portable personal electronic device. In an aspect, the second computing component includes a remote computing device. For example, the second computing component can include a computer associated with a facility or institution (e.g., a school, a team, a gym, a spa, a healthcare facility, a business, a government institution, and the like). For example, the remote computing device can be associated with a website upon which the determined relative hydration state can be stored, viewed, and tracked. In an aspect, the method includes wirelessly transmitting the determined relative hydration state of the target tissue of the subject to the second computing device. For example, the method can include using Bluetooth or other radiofrequency transmission to report the determined relative hydration state to a second computing component, e.g., to an application associated with a smart phone.

In an aspect, method 2700 includes storing the relative hydration state, as shown in block 2780. In an aspect, the method includes storing the determined relative hydration state of the target tissue of the subject in the data storage component of the hydration monitor. In an aspect, the determined relative hydration state of the target tissue of the subject is incorporated into the stored information associated with the reference reflected pulses correlated with the reference hydration states. In an aspect, the method includes storing the determined relative hydration state of the target tissue of the subject in the data storage component of the hydration monitor linked to at least one subject identifier. For example, the determined relative hydration state of the target tissue can be stored linked to at least one of the subject's name, phone number, social security number, identification number, fingerprints, voice scan, retinal scan, DNA scan, or other identifying information.

In an aspect, the method includes projecting a tracer on the nearest surface of the target tissue of the subject with a projector associated with the hydration monitor. For example, the method can include projecting a shape, a symbol, a dot, a spot, a crosshair, a ring, concentric rings, or any other tracer shape onto the nearest surface of the target tissue of the subject. In an aspect, the projected tracer corresponds to a beam width of the transmitted one or more pulses. For example, the tracer can include a projected light beam with a beam width on the target that simulates the beam width of the micro-impulse radar pulse.

In an aspect, the method can include documenting the portion of the subject's body subjected to the micro-impulse radar. In an aspect, the method includes capturing at least one image of a location on the subject with an image-capture device associated with the hydration monitor. In an aspect, the method includes capturing at least one image of a location on the subject associated with the target tissue of the subject with the image-capture device in response to actuating the micro-impulse radar component. For example, the method can include capturing an image of the portion of the subject's body subjected to the micro-impulse radar. In an aspect, the method includes storing the determined relative hydration state of the target tissue linked to the captured at least one image of the location on the subject. For example, the method can include storing the determined relative hydration state of the target tissue linked with an image of the location associated with the target tissue so as to document where the measurement was taken.

Described herein are methods for using a hydration monitor including a viewfinder, e.g., a hand-held hydration monitor including a viewfinder such as described above herein, to determine a hydration state of a subject. FIG. 28 shows a flowchart of an embodiment of a method for determining a hydration state with a hydration monitor. Method 2800 includes aligning a target on a subject with one or more alignment features in a viewfinder of a hydration monitor, the hydration monitor including the viewfinder, a micro-impulse radar component, a data storage component including stored information associated with reference reflected pulses correlated with reference hydration states, a user interface, and a computing component including a processor and circuitry, as shown in block 2810; actuating the micro-impulse radar component to transmit one or more pulses towards the target on the subject, as shown in block 2820; receiving information associated with one or more reflected pulses from a tissue associated with the target on the subject, as shown in block 2830; and comparing the received information associated with the one or more reflected pulses from the tissue associated with the target on the subject with the stored information associated with the reference reflected pulses correlated with the reference hydration states to determine a relative hydration state of the tissue, as shown in block 2840. In an aspect, some or all of the steps of method 2800 are performed by circuitry (e.g., logic circuitry) in cooperation with other components of the monitor.

FIG. 29 illustrates further aspects of a method for determining a hydration state with a hydration monitor such as described in FIG. 28. Method 2900 includes aligning a target on a subject with one or more alignment features in a viewfinder of a hydration monitor, as shown in block 2905. In an aspect, the method includes determining an alignment 2910 between the target on the subject and the one or more alignment features in the viewfinder of the hydration monitor. In some embodiments, the method includes having a user determine whether or not the target on the subject aligns with the one or more alignment features in the viewfinder. For example, the user can determine whether the target on the subject (e.g., a portion of the torso or the head) is sufficiently aligned with an alignment feature (e.g., a border) in the viewfinder and if aligned, manually actuate the micro-impulse radar component. For example, the user can determine whether the target on the subject "fills" the viewfinder to dimensions delineated by the one or more alignment features. In some embodiments, the method includes actuating the micro-impulse radar component to transmit one or more pulses towards the target on the subject in response to a user input to the user interface. For example, the method can include actuating the micro-impulse radar component in response to a user pushing an actuation button on the hydration monitor. For example, the method can include actuating the micro-impulse radar component in response to a user pushing an actuation button on the hydration monitor once alignment has been achieved.

In some embodiments, method 2900 includes determining an alignment 2910 between the target on the subject and the one or more alignment features in the viewfinder using alignment circuitry incorporated into the hydration monitor. In an aspect, the method includes automatically determining the alignment between the target on the subject and the one or more alignment features in the viewfinder of the hydration monitor. For example, the alignment circuitry can use one or more alignment algorithms to determine whether or not the target on the subject is sufficiently aligned with the one or more alignment features in the viewfinder. In an aspect, the method includes aligning a physical feature of the subject with the one or more alignment features in the viewfinder of the hydration monitor. In an aspect, the method includes aligning the target on the subject with at least one of a dot, a circle, a ring, a grid, or a border in the viewfinder of the hydration monitor. For example, the method can include aligning the center of the target on the subject with a crosshair in the viewfinder of the hydration monitor. In an aspect, the method includes aligning the target on the subject with an outline of a physical feature of the subject in the viewfinder of the hydration monitor. For example, the method can include aligning a subject's head with an outline of a head incorporated into the viewfinder of the hydration monitor.

In some embodiments, the method includes projecting the target on the subject with at least one light-emitting source associated with the hydration monitor. For example, the at least one light-emitting source can include at least one light-emitting diode (LED). Other non-limiting examples of projectors and light-emitting sources have been described above herein. In an aspect, the method includes projecting at least one of a shape, an outline, a symbol, a dot, a spot, a crosshair, a ring, or concentric rings on the subject with the at least one light-emitting source associated with the hydration monitor. In an aspect, the method includes projecting a tracer on the subject with at least one light-emitting source. In an aspect, the projected tracer corresponds to the beam width of the transmitted one or more pulses from the micro-impulse radar component. For example, the projected tracer can indicate the area on the subject that will be exposed or is being exposed with the micro-impulse radar.

In an aspect, method 2900 includes transmitting an alert signal 2920 to the user interface of the hydration monitor. In an aspect, the method includes generating an alert message 2925 in response to the transmitted alert signal 2920. In an aspect, the alert message includes at least one of an optical alert message, a textual alert message, an audible alert message, or a haptic alert message. In an aspect, the alert message includes one or more instructions.

In an aspect, the method includes transmitting an alert signal to the user if the target on the subject is not aligned with the one or more alignment features in the viewfinder of the hydration monitor. In an aspect, method 2900 includes "aligned?" determination point 2915. In an aspect, the method includes transmitting an alert signal, as shown in block 2920, in response to not satisfying the "aligned"

determination 2915. For example, the method can include transmitting an alert signal to the user interface of the hydration monitor if the target on the subject is not aligned with the one or more alignment features in the viewfinder of the hydration monitor. The method further includes generating an alert message in response to the transmitted alert signal, as shown in block 2925. For example, the method can include generating an alert message (e.g., an optical alert message, a textual alert message, an audible alert message, or a haptic alert message) if the target on the subject is not aligned with the one or more alignment features in the viewfinder of the hydration monitor.

In an aspect, method 2900 includes providing user instructions through the user interface. In some embodiments, the method includes providing user instructions through the user interface if the target on the subject is not aligned with the one or more alignment features in the viewfinder of the hydration monitor. For example, if the alignment does not satisfy the "aligned" determination point 2915, the method can include providing user instructions in block 2930. In an aspect, the method includes providing instructions to move the hydration monitor and/or the subject (e.g., up, down, right, left, forward, and/or back) to align the target on the subject with the one or more alignment features in the viewfinder of the hydration monitor.

In an aspect, the method includes comparing a size of the one or more alignment features in the viewfinder and the target on the subject. In an aspect, the method includes determining a distance between the hydration monitor and the target on the subject based on the compared size of the one or more alignment features in the viewfinder and the target on the subject. For example, a target on the subject that does not fill the viewfinder to boundaries delineated by the alignment features may indicate that the subject is too far away. For example, a target on the subject that overfills the viewfinder may indicate that the subject is too close. In an aspect, the method includes automatically actuating the micro-impulse radar component if the determined distance is within a range of predetermined operating distances of the hydration monitor. In an aspect, the method includes blocking actuation of the micro-impulse radar component if the determined distance is not within a range of predetermined operating distances of the hydration monitor. In an aspect, the method includes transmitting an alert signal to the user interface if the determined distance is not within a range of predetermined operating distances of the hydration monitor. In an aspect, the method includes providing instructions to a user if the determined distance is not within a range of predetermined operating distances of the hydration monitor. In an aspect, the method includes adjusting at least one of an output power or a beam angle of the micro-impulse radar component in response to the determined distance.

Method 2900 includes actuating the micro-impulse radar component, as shown in block 2935. In some embodiments, the method includes actuating the micro-impulse radar component in response to the determined alignment. In some embodiments, the method includes automatically actuating the micro-impulse radar component in response to the determined alignment if the determined alignment indicates that the one or more alignment features in the viewfinder and the target on the subject are aligned. For example, the method can include an "aligned?" determination point 2915, which when satisfied, allows the micro-impulse radar component to be actuated. In some embodiments, the method includes preventing the actuation of the micro-impulse radar component in response to the determined alignment if the determined alignment indicates that the one or more alignment features in the viewfinder and the target on the subject are not aligned. For example, if the "aligned" determination is not satisfied (e.g., the one or more alignment features in the viewfinder are not aligned with the target on the subject), the method can include blocking actuation signals from micro-impulse radar control circuitry of the hydration monitor preventing actuation of the micro-impulse radar component.

In some embodiments, the method includes actuating the micro-impulse radar component to transmit one or more pulses to the target tissue of the subject in response to a user input to the user interface. For example, method 2900 can include a user input to a user interface, as shown in block 2940, to actuate the micro-impulse radar component. For example, the method can include actuating the micro-impulse radar component in response to a user pushing an actuation button on the hydration monitor. For example, the method can include actuating the micro-impulse radar component in response to a user's audio command. In some embodiments, the user actuates the micro-impulse radar component in response to receiving an alert message indicating alignment between the one or more alignment features in the viewfinder and the target on the subject. For example, the user interface can include an optical alert, e.g., a green light, which indicates to a user that alignment has been satisfied.

In an aspect, method 2900 includes comparing at least one subject identifier with identifier information stored in the data storage component of the hydration monitor and generating an identifier comparison. In an aspect, the method includes entering the at least one subject identifier into the hydration monitor through the user interface. In an aspect, the method includes receiving the at least one subject identifier through the user interface. For example, at least one subject identifier (e.g., a name or identification number) can be entered into the hydration monitor through the user interface. In an aspect, the method includes receiving the at least one subject identifier through a wireless transmission. For example, the at least one subject identifier can be received wirelessly, e.g., through a radiofrequency transmission. In an aspect, method 2900 includes comparing a subject identifier with identifier information, as shown in block 2945. For example, the method can include comparing a subject's name, phone number, social security number, identification code, or other identifier with like identifier information stored in the data storage component. For example, the method can include comparing a biometric parameter of a subject, e.g., fingerprint, voice scan, retinal scan, DNA scan, or other biometric parameter with like biometric parameters stored in the data storage component. In an aspect, method 2900 includes generating an identifier comparison, as shown in block 2950. In an aspect, the method includes actuating the micro-impulse radar component in response to the identifier comparison. For example, if the identifier comparison indicates a substantial identity between the subject and identifier information in the data storage component, the method includes actuating the micro-impulse radar component.

In an aspect, method 2900 includes transmitting an alert signal 2955 to the user interface in response to the identifier comparison. In an aspect, the alert signal can indicate whether or not the identifier comparison meets or exceeds a threshold of identity between at least one subject identifier and the stored identifier information. For example, the alert signal may indicate to a user that the identifier comparison meets a threshold of identity, leading a user to actuate the micro-impulse radar component through a user input to the user interface (block 2940). For example, if the identifier comparison indicates a lack of identity between the at least one subject identifier and the identifier information in the data storage component, the method can include transmitting an alert signal to the user interface. In an aspect, the method includes blocking actuation of the micro-impulse radar component in response to the identifier comparison. For example, if the identifier comparison indicates a lack of identity between the at least one subject identifier and the identifier information in the data storage component, the method can include blocking activation of the micro-impulse radar.

Method 2900 includes receiving information associated with one or more reflected pulses, as shown in block 2960. In an aspect, the method includes receiving the information associated with the one or more reflected pulses from the tissue associated with the target on the subject when the determined alignment indicates that the one or more alignment features in the viewfinder and the target on the subject are aligned. For example, the hydration determination circuitry of the hydration monitor can be configured to only accept information associated with the one or more reflected pulses if the determined alignment indicates that the one or more alignment features in the viewfinder and the target on the subject are aligned.

In an aspect, the method includes evaluating the quality of the received information associated with the one or more reflected pulses from the target tissue of the subject against a quality threshold, as shown in block 2965. In an aspect, the quality threshold can include a signal-to-noise threshold. In an aspect, the quality threshold can include a "reasonability" threshold. For example, is the received information associated with the one or more reflected pulses reasonable (e.g., in terms of amplitude, frequency, and the like), for the measuring conditions. If the quality threshold indicates that the received information associated with the one or more reflected pulses is good, then the comparison of the received information with the stored information can proceed. If the quality threshold indicates that the received information associated with the one or more reflected pulses is bad, then additional information is required. In an aspect, the method includes actuating the micro-impulse radar component to transmit one or more additional pulses to the tissue associated with the target on the subject if the evaluated quality of the received one or more reflected pulses fails to meet or exceed the quality threshold.

In an aspect, the method includes comparing the received information associated with the one or more reflected pulses from the tissue associated with the target on the subject with the stored information associated with the reference reflected pulses correlated with the reference hydration states, as shown in block 2970. In an aspect, the method includes comparing the received information associated with the one or more reflected pulses from the tissue associated with the target on the subject with the stored information associated with the reference reflected pulses correlated with the reference hydration states when the target on the subject is aligned with the one or more alignment features in the viewfinder of the hydration monitor. For example, the method can include only performing the comparison if the target on the subject and the one or more alignment features in the viewfinder of the hydration monitor are properly aligned.

In an aspect, the method includes comparing the received information associated with the one or more reflected pulses from the target tissue of the subject with stored information associated with reference reflected pulses correlated with reference hydration states of a phantom. In an aspect, the method includes comparing the received information associated with one or more reflected pulses from the target tissue of the subject with stored information associated with reference reflected pulses correlated with measured hydration states. For example, the measured hydration states can include hydration states of a subject and/or one or more other individuals measured through urine analysis, blood analysis, saliva analysis, weight loss/gain, or other means of measuring a hydration state.

In an aspect, the method includes determining the relative hydration state of the tissue based on a time spectrum of the one or more reflected pulses. In an aspect, the method includes determining the relative hydration state of the tissue based on a frequency spectrum of the one or more reflected pulses. In an aspect, the method includes determining the relative hydration state of the tissue based on comparing a frequency spectrum of the one or more reflected pulses and a frequency spectrum of a transmitted pulse. In an aspect, the method includes determining the relative hydration state of the tissue as a function of tissue depth.

In an aspect, the method includes reporting the relative hydration state, as shown in block 2975. In an aspect, the method includes reporting the determined relative hydration state of the tissue to a user through the user interface. For example, the method can include reporting the determined relative hydration state of the tissue as a textual message on a display of the hydration monitor. In an aspect, the method includes reporting the determined relative hydration state of the tissue relative to a reference hydration state of the tissue. For example, the method can include reporting a relative hydration state at a current time point (e.g., during or after strenuous activity) relative to a hydration state measured at a prior time point (e.g., before initiating the strenuous activity). In an aspect, the method includes reporting the determined relative hydration state of the tissue to a second computing component. In an aspect, the second computing component includes a personal electronic device, e.g., a smart phone, a tablet, or other portable personal electronic device. In an aspect, the second computing component includes a remote computing device. For example, the second computing component can include a computer associated with a facility or institution (e.g., a school, a team, a gym, a spa, a healthcare facility, a business, a government institution, and the like). For example, the remote computing device can be associated with a website upon which the determined relative hydration state can be stored, viewed, and tracked. In an aspect, the method includes wirelessly transmitting the determined hydration state of the tissue to the second computing device. For example, the method can include using Bluetooth or other radiofrequency transmission to report the determined relative hydration state to a second computing component, e.g., to an application associated with a smart phone.

In an aspect, method 2900 includes storing the relative hydration state, as shown in block 2980. In an aspect, the method includes storing the determined relative hydration state of the tissue in the data storage component of the hydration monitor. In an aspect, the determined relative hydration state of the tissue is incorporated into the stored information associated with the reference reflected pulses correlated with the reference hydration states. In an aspect, the method includes storing the determined relative hydration state of the tissue in the data storage component of the hydration monitor linked to at least one subject identifier. For example, the determined relative hydration state of the target tissue can be stored linked to at least one of the subject's name, phone number, social security number, identification number, fingerprints, voice scan, retinal scan, DNA scan, or other identifying information.

In an aspect, the method can include documenting the portion of the subject's body subjected to the micro-impulse radar. In an aspect, the method includes capturing at least one image of the target on the subject with an image-capture device associated with the hydration monitor. In an aspect, the method includes capturing at least one image of the target on the subject with the image-capture device in response to actuating the micro-impulse radar component. For example, the method can include capturing an image of the portion of the subject's body subjected to the micro-impulse radar. In an aspect, the method includes storing the determined relative hydration state of the tissue linked to the captured at least one image of the target on the subject. For example, the method can include storing the determined relative hydration state of the target tissue linked with an image of the target on the subject associated with the tissue so as to document where the measurement was taken.

Described herein are methods for using a hydration monitor including a location-capture component, e.g., a handheld hydration monitor including a location-capture component such as described above herein, to determine a hydration state of a subject. FIG. 30 shows a flowchart of an embodiment of a method for determining a hydration state with a hydration monitor including a location-capture component. Method 3000 includes receiving information associated with a location on a subject from a location-capture component of the hydration monitor, the hydration monitor including the location-capture component, a micro-impulse radar component, a data storage component including stored location information and stored information associated with reference reflected pulses correlated with reference hydration states, a user interface, and a computing component including a processor and circuitry, as shown in block 3010; comparing the received information associated with the location on the subject with the stored location information and determining a registration value, as shown in block 3020; actuating the micro-impulse radar component to transmit one or more pulses to the location on the subject, as shown in block 3030; receiving one or more reflected pulses from a tissue associated with the location on the subject, as shown in block 3040; and comparing information associated with the received one or more reflected pulses from the tissue associated with the location on the subject with the stored information associated with the reference reflected pulses correlated with the reference hydration states to determine a relative hydration state of the tissue, as shown in block 3050. In an aspect, some or all of the steps of method 3000 are performed by circuitry (e.g., logic circuitry) in cooperation with other components of the hydration monitor.

Figure 31:
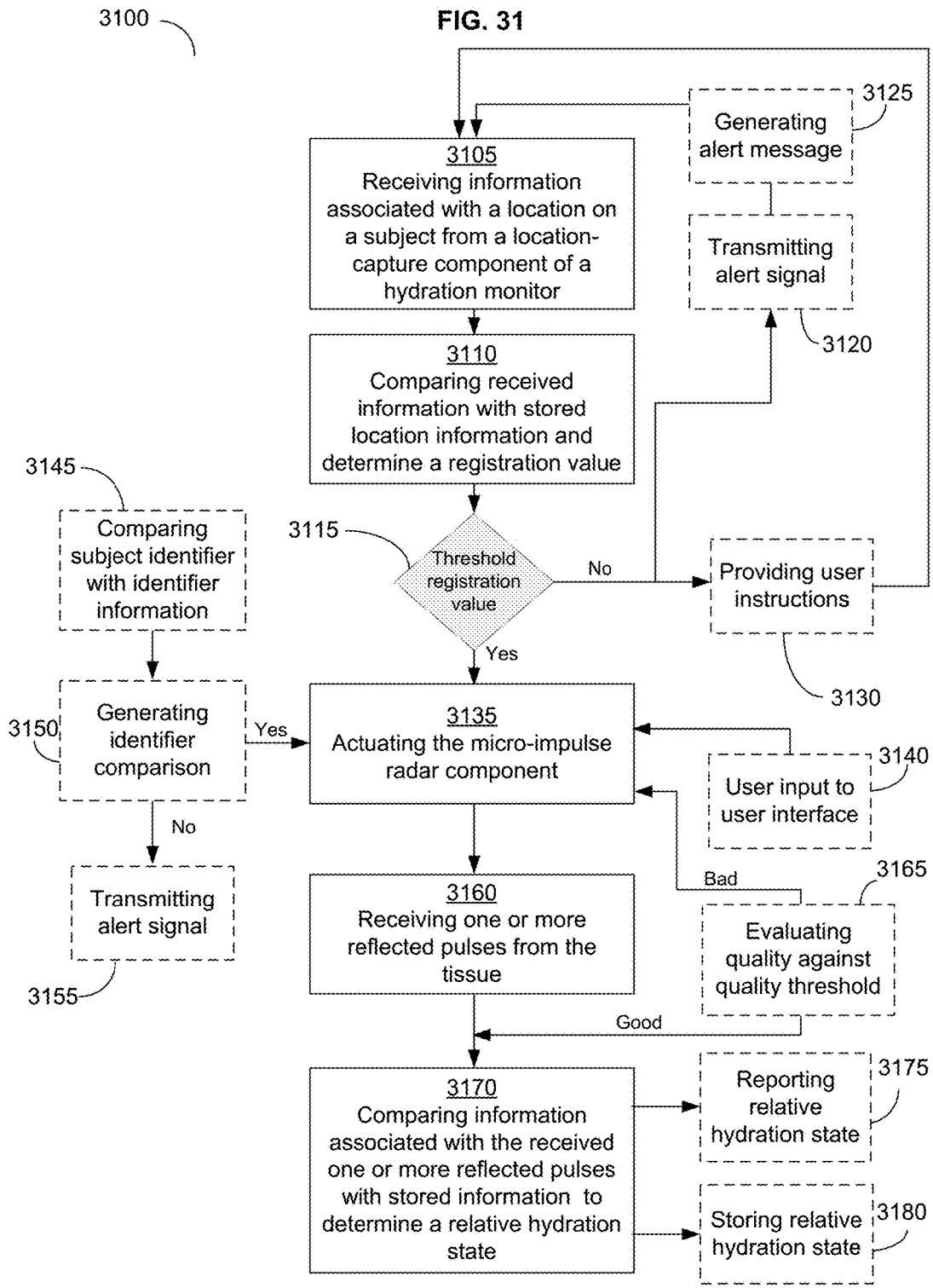
FIG. 31 is a flowchart illustrating further aspects of a method such as shown in FIG. 30.

FIG. 31 illustrates further aspects of a method for determining a hydration state with a hydration monitor such as described in FIG. 30. Method 3100 includes receiving information associated with a location on a subject from a location-capture component of a hydration monitor, as shown in block 3105. In an aspect, receiving the information associated with the location on the subject from the location-capture component of the hydration monitor includes receiving one or more images associated with the location on the subject from the location-capture component of the hydration monitor. For example, the method can include receiving one or more images of a location on the subject with an image-capture device, e.g., a digital camera, associated with the hydration monitor. In an aspect, receiving the information associated with the location on the subject from the location-capture component of the hydration monitor includes receiving one or more fiducials associated with the location on the subject from the location-capture component of the hydration monitor. For example, the method can include receiving information associated with one or more fiducials associated with a location on the subject with a fiducial reader, e.g., an RFID tag reader or image-capture device, associated with the hydration monitor.

Method 3100 further includes comparing the received information associated with the location on the subject with stored location information and determining a registration value 3110. In an aspect, the method includes comparing one or more images associated with the location on the subject with one or more stored images. For example, the method can include comparing an image of a body region of the subject (e.g., a leg, an arm, torso, or head) with stored images of body regions. In an aspect, the stored images are stored images captured from the subject and/or one or more other individuals. In an aspect, the method includes comparing one or more fiducials associated with the location on the subject with one or more stored fiducials. For example, the method can include comparing information associated with a pattern of physical landmarks on a location on the subject with stored fiducials. For example, the method can include comparing information associated with a pattern of fiducials markers placed on or worn over a location on the subject with stored fiducials. In an aspect, the comparison between the received information associated with the location on the subject and the stored location information is performed by registration circuitry of the hydration monitor. For example, the registration circuitry can use registration or alignment algorithms for the comparison, non-limiting examples of which have been described above herein.

In an aspect, the method includes determining a registration value based on the comparison between the received information associated with a location on a subject and the stored location information. In an aspect, the method includes using registration circuitry to compare the received information associated with the location on the subject with stored location information to determine the registration value. For example, the method can include using one or more algorithms to determine how well the received information associated with the location on the subject registers or aligns with the stored location information. In an aspect, the registration value ranges from a value of "1" indicating a substantially perfect registration to a value of "0" indicating no registration. In an aspect, the registration value ranges from a value or 100% indicating a substantially perfect registration to a value of 0% indicating no registration.

In an aspect, method 3100 includes threshold registration value determination point 3115. In an aspect, a threshold registration value must be met or exceeded to satisfy a registration determination. In some embodiments, the threshold registration value can be set high, e.g., 90-100%. In some embodiments, the threshold registration value can be set relatively low, e.g., 50%.

In an aspect, method 3100 includes transmitting an alert signal 3120 to the user interface of the hydration monitor in response to the determined registration value. For example, the method can include transmitting an alert signal if the location on the subject registers with the stored location information. For example, the method can include transmitting an alert signal if the location on the subject does not register with the stored location information. In an aspect, the method includes generating an alert message 3125 in response to the transmitted alert signal 3120. In an aspect, the alert message includes at least one of an optical alert message, a textual alert message, an audible alert message, or a haptic alert message. In an aspect, the alert message includes one or more instructions.

In an aspect, the method includes transmitting an alert signal to the user if the location on the subject does not register with the stored location information. In an aspect, method 3100 includes transmitting an alert signal, as shown in block 3120, in response to not satisfying the "threshold registration value" determination 3115. In an aspect, the method includes transmitting an alert signal to the user interface of the hydration monitor if the determined registration value does not meet or exceed a threshold registration value. For example, alert circuitry associated with the hydration monitor can be configured to transmit an alert signal to the user interface of the hydration monitor if the determined registration value indicates that the received information associated with the location on the subject does not register with the stored location information. Method 3100 includes generating an alert message (block 3125) in response to the transmitted alert signal. For example, the method can include generating an alert message (e.g., an optical alert message, a textual alert message, an audible alert message, or a haptic alert message) if the received information associated with the location on the subject does not register with the stored location information.

In an aspect, method 3100 includes providing user instructions (block 3130). In an aspect, the method includes providing user instructions through the user interface. In some embodiments, the method includes providing user instructions through the user interface of the hydration monitor if the determined registration value does not meet or exceed a threshold registration value. For example, if the determined registration value does not satisfy the "threshold registration value" determination 3115, the method can include providing user instructions in block 3130. In an aspect, the method includes providing instructions to move the hydration monitor and/or the subject (e.g., up, down, right, left, forward, and/or back) to capture information associated with a different location on the subject.

Method 3100 includes actuating the micro-impulse radar component, as shown in block 3135. In some embodiments, the method includes actuating the micro-impulse radar component to transmit the one or more pulses to the location on the subject in response to the determined registration value. In some embodiments, the method includes automatically actuating the micro-impulse radar if the determined registration value meets or exceeds a threshold registration value. For example, micro-impulse radar control circuitry of the hydration monitor can be configured to automatically actuate the micro-impulse radar component if the determined registration value indicates that the received information associated with the location on the subject registers with the stored location information. For example, the method can include a "threshold registration value" determination point 3115, which when satisfied, allows the micro-impulse radar component to be actuated. In some embodiments, the method includes preventing the actuation of the micro-impulse radar component in response to the determined registration value if the determined registration value does not meet or exceed the threshold registration value. For example, if the "threshold registration value" determination is not satisfied (e.g., the received information associated with the location on the subject does not register with the stored location information), the method can include blocking actuation signals from micro-impulse radar control circuitry of the hydration monitor, preventing actuation of the micro-impulse radar component.

In some embodiments, method 3100 includes a user input to a user interface 3140 to actuate the micro-impulse radar component. In an aspect, the method includes actuating the micro-impulse radar component in response to a user input to the user interface. For example, the method can include actuating the micro-impulse radar component in response to a user pushing an actuation button on the hydration monitor. For example, the method can include actuating the micro-impulse radar component in response to a user's audio command. In some embodiments, the user actuates the micro-impulse radar component in response to receiving an alert message indicating that the determined registration value has met or exceeded the threshold registration value. For example, an optical alert, e.g., a green light, may indicate that the received information associated with the location on the subject registers with stored location information and that the location is an appropriate location for scanning with the hydration monitor.

In an aspect, method 3100 includes comparing a subject identifier with identifier information, as shown in block 3145, and generating an identifier comparison, as shown in block 3150. In an aspect, the method includes comparing at least one subject identifier with identifier information stored in the data storage component of the hydration monitor and generating an identifier comparison. In an aspect, the method includes entering the at least one subject identifier into the hydration monitor through the user interface. In an aspect, the method includes receiving the at least one subject identifier through the user interface. For example, at least one subject identifier (e.g., a name or identification number) can be entered into the hydration monitor through the user interface. For example, the at least one subject identifier can be received wirelessly, e.g., through a radiofrequency transmission. In an aspect, method 3100 includes comparing a subject identifier with identifier information, as shown in block 3145. For example, the method can include comparing a subject's name, phone number, social security number, identification code, or other identifier with like identifier information stored in the data storage component. For example, the method can include comparing a biometric parameter of a subject, e.g., fingerprint, voice scan, retinal scan, DNA scan, or other biometric parameter with like biometric parameters stored in the data storage component. In an aspect, method 3100 includes generating an identifier comparison, as shown in block 3150. In an aspect, the method includes actuating the micro-impulse radar component in response to the identifier comparison. For example, if the identifier comparison indicates a substantial identity between the subject and identifier information in the data storage component, the method includes actuating (and/or authorizing actuation of) the micro-impulse radar component.

In an aspect, the method includes transmitting an alert signal (block 3155) to the user interface in response to the identifier comparison. In an aspect, the alert signal can indicate whether or not the identifier comparison meets or exceeds a threshold of identity between at least one subject identifier and the stored identifier information. For example, the alert signal may indicate to a user that the identifier comparison meets a threshold of identity, leading a user to actuate the micro-impulse radar component through a user input to the user interface (block 3140). For example, if the identifier comparison indicates a lack of identity between the at least one subject identifier and the identifier information in the data storage component, the method can include transmitting an alert signal to the user interface.

Method 3100 includes receiving one or more reflected pulses from the tissue. In an aspect, the method includes receiving the one or more reflected pulses from the tissue associated with the location on the subject with at least one antenna associated with the hand-held hydration monitor. In an aspect, the method includes receiving the one or more reflected pulses from the tissue associated with the location on the subject when the determined registration value meets or exceeds the threshold registration value. For example, the hydration determination circuitry of the hydration monitor can be configured to only accept information associated with the one or more reflected pulses if the determined registration value indicates that the location on the subject is appropriate.

In an aspect, method 3100 includes evaluating the quality of the information associated with the received one or more reflected pulses from the tissue associated with the location on the subject against a quality threshold, as shown in block 3165. In an aspect, the quality threshold can include a signal-to-noise threshold. In an aspect, the quality threshold can include a "reasonability" threshold. For example, is the information associated with the received one or more reflected pulses reasonable (e.g., in terms of amplitude, frequency, and the like) for the measuring conditions. If the quality threshold indicates that the information associated with the received one or more reflected pulses is "good," then the comparison of the received information with the stored information can proceed. If the quality threshold indicates that the information associated with the received one or more reflected pulses is "bad," then additional information is required. In an aspect, the method includes actuating the micro-impulse radar component to transmit one or more additional pulses to the location on the subject if the evaluated quality of the information associated with the received one or more reflected pulses fails to meet or exceed the quality threshold.

In an aspect, the method includes comparing the information associated with the received one or more reflected pulses from the tissue associated with the location on the subject with the stored information associated with the reference reflected pulses correlated with the reference hydration states, as shown in block 3170. In an aspect, the method includes comparing the information associated with the received one or more reflected pulses from the tissue associated with the location on the subject with the stored information associated with the reference reflected pulses correlated with the reference hydration states when the determined registration value meets or exceeds a threshold registration value. For example, the method can include only performing the comparison if the location on the subject registers with the stored location information.

In an aspect, the method includes comparing the information associated with the received one or more reflected pulses from tissue associated with the location on the subject with stored information associated with reference reflected pulses correlated with reference hydration states of a phantom. In an aspect, the method includes comparing the information associated with the received one or more reflected pulses from the tissue associated with the location on the subject with stored information associated with reference reflected pulses correlated with measured hydration states. For example, the measured hydration states can include hydration states of a subject and/or one or more other individuals measured through urine analysis, blood analysis, saliva analysis, weight loss/gain, or other means of measuring a hydration state.

In an aspect, the method includes determining the relative hydration state of the tissue associated with the location on the subject based on a time spectrum of the one or more reflected pulses. In an aspect, the method includes determining the relative hydration state of the tissue associated with the location on the subject based on a frequency spectrum of the one or more reflected pulses. In an aspect, the method includes determining the relative hydration state of the tissue associated with the location on the subject based on a comparison of a frequency spectrum of the one or more reflected pulses and a frequency spectrum of a transmitted pulse. In an aspect, the method includes determining a relative hydration state of the tissue associated with the location on the subject as a function of tissue depth.

In an aspect, method 3100 includes reporting the relative hydration state, as shown in block 3175. In an aspect, the method includes reporting the determined relative hydration state of the tissue to a user through the user interface of the hydration monitor. For example, the method can include reporting the determined relative hydration state of the target tissue as a textual message on a display of the hydration monitor. In an aspect, the method includes reporting the determined relative hydration state of the tissue relative to a reference hydration state of the tissue. For example, the method can include reporting a determined relative hydration state at a current time point (e.g., during or after strenuous activity) relative to a hydration state measured at a prior time point (e.g., before initiating the strenuous activity). In an aspect, the method includes reporting the determined relative hydration state of the tissue to a second computing component. In an aspect, the second computing component includes a personal electronic device, e.g., a smart phone, a tablet, or other portable personal electronic device. In an aspect, the second computing component includes a remote computing device. For example, the second computing component can include a computer associated with a facility or institution (e.g., a school, a team, a gym, a spa, a healthcare facility, a business, a government institution, and the like). For example, the remote computing device can be associated with a website upon which the determined relative hydration state can be stored, viewed, and tracked. In an aspect, the method includes wirelessly transmitting the determined hydration state of the tissue to the second computing device. For example, the method can include using Bluetooth or other radiofrequency transmission to report the determined relative hydration state of the tissue to a second computing component, e.g., to an application associated with a smart phone.

In an aspect, method 3100 includes storing the relative hydration state, as shown in block 3180. In an aspect, the method includes storing the determined relative hydration state of the tissue in the data storage component of the hydration monitor. In an aspect, the determined relative hydration state of the tissue is incorporated into the stored information associated with the reference reflected pulses correlated with the reference hydration states. In an aspect, the method includes storing the determined relative hydration state of the tissue in the data storage component of the hydration monitor linked to at least one subject identifier. For example, the determined relative hydration state of the target tissue can be stored linked to at least one of the subject's name, phone number, social security number, identification number, fingerprints, voice scan, retinal scan, DNA scan, or other identifying information. In an aspect, the method includes storing the determined relative hydration state of the tissue in the data storage component of the hydration monitor linked to the received information associated with the location on the subject.

In an aspect, method 3100 includes projecting a tracer on the location on the subject with a projector component associated with the hydration monitor. For example, the method can include projecting a shape, a symbol, a dot, a spot, a crosshair, a ring, concentric rings, or any other tracer shape on the location on the subject. In an aspect, the projected tracer corresponds to a beam width of the transmitted one or more pulses. For example, the tracer can include a projected light beam with a beam width on the target that simulates the beam width of the micro-impulse radar pulse.

In an aspect, the method can include documenting the portion of the subject's body subjected to the micro-impulse radar. In an aspect, method 3100 includes capturing at least one image of the location on the subject. For example, the method can include capturing an image of the location on the subject with the location-capture component, e.g., a digital camera. In an aspect, the method includes capturing at least one image of the location on the subject in response to actuating the micro-impulse radar component. For example, the method can include capturing an image of the portion of the subject's body subjected to the micro-impulse radar. In an aspect, the method includes storing the determined relative hydration state of the tissue linked to the captured at least one image of the location on the subject. For example, the method can include storing the determined relative hydration state of the target tissue linked with an image of the location associated with the target tissue so as to document where the measurement was taken.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode (s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

Prophetic Example 1: Generating a Database of Reflected Radar Pulses Correlated with Hydration States of a Phantom A database of signal patterns from reflected pulses correlated with hydration states is generated using phantoms constructed with varying water content. A hand-held hydration monitor is used to scan the phantoms of varying water content with micro-impulse radar. Reflected radar pulses are received and processed, and digitized signal patterns correlated with the relative water content of the phantoms. The hand-held hydration monitor includes a micro-impulse radar component including a pulse generator, at least one antenna, a receiver, and a signal processor, a user interface, a data storage component, and a computing component including a processor and circuitry.

Oil-in-gelatin phantoms are constructed according to Lazebnik et al. (2005) "Tissue-mimicking phantom materials for narrowband and ultrawideband microwave applications," Phys. Med. Biol. 50:4245-4258, which is incorporated herein by reference. Briefly, gelatin (e.g., 34 grams) derived from calfskin (Vyse Gelatin Company, Schiller Park, Ill.) is mixed with water:propanol (95:5) and heated to about 90 degrees C. The mix is cooled in a water bath to about 50 degrees C. Varying percentages of oil are added to aliquots of the gelatin/water mixture. The water-to-oil content of the gelatin is varied from 60% and 95% (v/v; ~2-5% water gradation steps). Small volumes of liquid surfactant and formaldehyde are added, the latter to cross-link the gelatin. The mixture is poured into a mold and allowed to gel/crosslink over the course of 5-7 days. The hand-held hydration monitor is used to expose each phantom to ultrashort radar pulses (<1 ns) with pulse repetitions on the order of 4 MHz. See, e.g., Levy et al. (2011) "Micropower Impulse Radar: A Novel Technology for Rapid Real-Time Detection of Pneumothorax," *Emergency Medicine International*, Volume 2011, Article ID 279508, which is incorporated herein by reference. The radar return signals generated by the reflected pulses are received by the receiver, processed by the signal processor, digitized, and stored for analysis. A time spectrum of the digitized signals is correlated with a percentage water content of the phantom.

Prophetic Example 2: Generating a Personalized Database of Reflected Radar Pulses Correlated with Hydration State for a Subject A personalized database or standard curve of reflected pulses correlated with hydration state is generated for a subject using a hand-held hydration monitor. The hand-held hydration monitor includes a micro-impulse radar component including a pulse generator, at least one antenna, a receiver, and a signal processor; a user interface; a data storage component; and a computing component including a processor and circuitry. The hand-held hydration monitor is used to scan a target location on a subject with micro-impulse radar. Reflected radar pulses are received and processed, and digitized signal patterns are correlated with measured hydration states of the subject. The measured hydration states are measured using one or more urinary hydration biomarkers.

Standard hydration measurements as well as scanning with the micro-impulse radar component of the hand-held hydration monitor are performed on the subject at various hydration states, e.g., high hydration state (after IV infusion of fluids or consumption of one or more liters of fluid); normal hydration state, low hydration state (after mild exercise with sweating for a period of time and/or in the absence of consuming liquids), very low hydration state (after heavy exertion with excessing sweating and/or in the absence of consuming liquids). In each of the specific hydration states, the individual provides a urine sample for analysis. The urine analysis includes assessments of urine color, specific gravity, volume, and osmolality. See, e.g., Perrier et al. (2013) "Relation between urinary hydration biomarkers and total fluid intake in healthy adults." Eur. J. Clin. Nutr. 67:939-943, which is incorporated herein by reference. Urine analysis is used to determine the hydration state of the subject.

At each hydration state, urine is collected and total urine mass is determined to the nearest 1 gram. Urine osmolality is measured via freezing point osmometry using an osmometer (from, e.g., Advance Instruments, Inc., Norwood, Mass.). Urine specific gravity is measured using a pen refractometer. Urine biochemistry assays include cortisol, aldosterone, citrate, and oxalate. See, e.g., Perrier et al. (2013) "Hydration biomarkers in free-living adults with different levels of habitual fluid consumption," *Brit. J. Nutr.* 109:1678-1687, which is incorporated herein by reference.

In a specific hydration state, the subject provides a urine sample and a specific location on the subject's body is scanned with the hand-held hydration monitor. Reflected pulses are received by the receiver of the hand-held hydration monitor, processed, and a corresponding reflected signal pattern stored in the data storage component. The reflected signal patterns recorded at each hydration state are correlated with hydration states measured by urine analysis in a database or lookup table. The database or lookup table can be used as a personalized standard curve for the subject for comparison with micro-impulse radar measurements performed in the future. The database or lookup table can include personalized standard curves generated at different locations on the subject, e.g., a standard curve for torso measurements at various hydration states versus a standard curve for head measurement at various hydration states. The database or lookup table can include personalized standard curves generated at different distances from the hand-held hydration monitor.

Prophetic Example 3: Generating a General Population Database of Reflected Radar Pulses Correlated with Hydration States A general population database of reflected pulses correlated with hydration state is generated from one or more other individuals using a hand-held hydration monitor. The hand-held hydration monitor includes a micro-impulse radar component including a pulse generator, at least one antenna, a receiver, and a signal processor, a user interface, a data storage component, and a computing component including a processor and circuitry. The hand-held hydration monitor is used to scan a target location on each of the one or more other individuals with micro-impulse radar. A receiver on the hand-held hydration monitor collects reflected radar pulses and correlates digitized signal patterns corresponding to the reflected radar pulses with measured hydration states of the individuals. The measured hydration states are measured using one or more urinary hydration biomarkers.

Standard hydration measurements are performed on each individual in a general population of individuals to measure a hydration state. Each individual provides a urine sample for urine analysis (e.g., osmolality and specific gravity). A specific target location (e.g., the torso) on each individual is scanned using the hand-held hydration monitor. Reflected pulses from the specific target location are received by the receiver, processed, and a pattern of reflected signals recorded. The reflected signals for each individual at a specific target location are correlated with the hydration state for each individual to generate a database of reflected signals correlated with hydration state at that specific target location. Additional data may be generated at various hydration states from other target locations, e.g., the head, legs, arms, hands, etc., of each individual to generate a database of reflected signals correlated with hydration state at various target locations. Similarly, additional data may be generated at various hydration states from one or more target locations at different distances between the hand-held hydration monitor and the target location to generate a database of reflected signals correlated with hydration state at one or more target locations as a function of distance.

Prophetic Example 4: Measuring Relative Changes in Reflected Radar Pulses

A hand-held hydration monitor is described herein for use in measuring relative hydration state of a target tissue of an athlete during the course of a strenuous workout. The hand-held hydration monitor includes a micro-impulse radar component including a pulse generator, at least one antenna, a receiver, and a signal processor, a user interface, a data storage component, and a computing component including a process and circuitry configured to determine a relative hydration state.

Prior to an athlete beginning a workout, a trainer uses the hand-held hydration monitor to scan a target location on the athlete, e.g., the torso of the athlete, to generate a baseline reading for the day. The trainer points the hand-held hydration monitor at the athlete who is standing at a distance from the trainer and actuates the micro-impulse radar component with an actuation button. At least one first reflected pulse from a nearest surface of the target location on the subject is received by the hand-held hydration monitor and a distance is determined passed on the round trip travel time of the pulse. Circuitry within the hand-held hydration monitor determines that the determined distance is 30 feet. The circuitry determines that the determined distance of 30 feet is not within a range of predetermined operating distances of the hand-held hydration monitor. An alert message is sent in the form of a flashing red light on an outer surface of the hand-held hydration monitor, indicating to the trainer that the hand-held hydration monitor needs to be moved closer to the athlete. The trainer moves closer to the athlete (or the athlete moves closer to the trainer), repeats the distance finding until an alert message in the form of a flashing green light indicates that the hand-held hydration monitor and the target location on the athlete are at an appropriate distance.

Once the appropriate distance is found, the trainer scans the target location on the athlete with micro-impulse radar and receives a first series of reflected pulses. The first series of reflected pulses are processed and a corresponding baseline digitized signal pattern is stored in the data storage component. Athlete information, e.g., name, identification number, photo, or any other subject identifier, is also collected from the athlete. An image is captured of the target location on the athlete which is scanned and linked with the baseline digitized signal pattern in the data storage component.

The athlete is periodically rescanned during the course of a strenuous workout to measure changes in the digitized signal pattern from the reflected pulses. For example a specific peak in a time spectrum of the digitized signal pattern may increase or decrease in amplitude as a function of the hydration state. The hand-held hydration monitor provides an alert message to the trainer reporting a change in the hydration state. The hand-held hydration monitor further provides recommendations for hydration depending upon whether a current hydration state is above or below baseline hydration for the workout.

Prophetic Example 5: A Hand-Held Hydration Monitor with Alignment Features on a Transparent Window A hand-held hydration monitor with a transparent window viewfinder and use thereof is described herein. The hand-held hydration monitor includes the transparent window viewfinder and a micro-impulse radar component including a pulse generator, at least one antenna, a receiver, and a signal processor. The transparent window viewfinder includes a transparent window of glass and includes one or more alignment features. The alignment feature, e.g., a ring, is inked onto the glass window. The ring on the transparent glass window is intended to be aligned with a specific target on a subject, e.g., the subject's head. The hand-held hydration monitor further includes a user interface (e.g., at least one button including an actuation button) and a computing component including a processor and circuitry configured to determine a relative hydration state.

A homecare provider, e.g., a parent, uses the hand-held hydration monitor to monitor the hydration state of a sick child experiencing a fever. The parent holds the hand-held hydration monitor at eye level about 6 inches from his or her eyes and points the monitor in the direction of the sick child's head. The parent moves the hand-held hydration monitor right, left, backward, forward, up and/or down until the sick child's head fills the ring inked into the transparent window of glass. When the sick child's head is aligned with the ring, the parent actuates the micro-impulse radar component of the hand held hydration monitor by pushing the actuation button.

A receiver associated with the micro-impulse radar component of the hand-held hydration monitor receives a series of reflected pulses from the sick child's head. Hydration determination circuitry receives information associated with the reflected pulses from the sick child's head and compares it with stored information including a database of reference reflected pulses correlated with reference hydration states. The stored information includes reference information from a population of age matched children as well as stored historical hydration states of the child. A relative hydration state is determined and reported to the parent via a display associated with the hand-held hydration monitor.

Prophetic Example 6: Hydration Monitor with Alignment Features on Electronic Viewfinder A hand-held hydration monitor including an electronic viewfinder and use thereof is described herein. The hand-held hydration monitor includes an electronic viewfinder with one or more alignment features.

The hand-held hydration monitor includes a micro-impulse radar component including a pulse generator, at least one antenna, a receiver, and a signal processor. The hand-held hydration monitor further includes an electronic viewfinder, i.e., an electronic display operable coupled to an image-capture device. The electronic viewfinder includes an alignment feature, e.g., a border, within the field of view on the electronic display. The border in the field of view on the electronic display is intended to be aligned with the head of a subject.

A sports trainer associated with a sports team, e.g., a soccer team, uses the hand-held hydration monitor to measure a hydration state of each of the team members prior to the start of a practice session. The sports trainer holds the hand-held hydration monitor at about 12 to 18 inches from his/her eyes while pointed at the subject's forehead. An image of the subject's forehead captured with the image-capture device is displayed on the electronic display relative to the border. The hand-held hydration monitor includes alignment circuitry configured to determine an alignment between the border and the head of the subject. The alignment circuitry includes at least one algorithm for comparing two images, e.g., the image of the subject's head and the image of the border. In response to the determined alignment, the alignment circuitry transmits an alert signal to the user interface of the monitor. If the subject's head is aligned with the border in the electronic viewfinder, a positive alert message (e.g., a green light or an "aligned" message) is provided by the user interface. If the subject's head is not aligned with the border in the electronic viewfinder, a negative alert message (e.g., a red light or a "not aligned" message) is provided by the user interface. In response to the negative alert message, the user interface also provides instructions to the trainer to move closer to the subject to improve the alignment. Once alignment has been achieved, the micro-impulse radar control circuitry of the hand-held hydration monitor automatically actuates the micro-impulse radar component to transmit one or more pulses to the head of the subject. The reflected pulses are detected by the receiver, processed, and a signal pattern (e.g., a time spectrum including relative signal amplitude over a relative time period) associated with the reflected pulses is stored in the data storage component.

The measurements taken at the start of the practice session serve as a baseline measurement for each team member. Each of the baseline hydration states is stored in the data storage component of the hand-held hydration monitor linked to a subject identifier, e.g., the subject's name, identification number, and/or photo. The sports trainer periodically re-measures each of the team members during the course of the practice session. Hydration determination circuitry compares the signal pattern associated with the reflected pulses from the subject's head with stored signal patterns associated with reflected pulses measured at an earlier time point, e.g., at the start of the practice session. The relative hydration state of the subject is reported to the sports trainer through the user interface of the hand-held hydration monitor. The relative hydration state of the subject is also wirelessly transmitted to a laptop computer used by the sports trainer to track the hydration states of the team members over time.

Prophetic Example 7: A Hand-Held Hydration Monitor with a Location-Capture Component Described herein is an embodiment of a hand-held hydration monitor with a location-capture component and use thereof. The hand-held hydration monitor includes an image-capture device configured to capture one or more images of a location on a subject, a micro-impulse radar component including a pulse generator, at least one antenna, a receiver, and a signal processor, a data storage component including stored reference images as well as a database of reference reflected pulses correlated with reference hydration states, and a computing component including a microprocessor and circuitry including registration circuitry, micro-impulse radar control circuitry, and hydration determination circuitry. The hand-held hydration monitor including the location-capture component is set up to consistently perform hydration measurements at the same location on the subject's body based on comparing images of the current location with stored location information, e.g., stored images.

The image-capture device includes at least one CMOS (complementary metal-oxide-semiconductor) or CCD (charge-coupled device) image sensor incorporated into the hand-held hydration monitor. The image-capture device is operably coupled to the user interface, e.g., a thin film transistor liquid crystal display (from, e.g., Microtips Technology Inc., Orlando, Fla.), allowing the user to view the one or more images captured by the image-capture device. The user, e.g., a coach, points the hand-held hydration monitor at the forearm of a subject, e.g., an athlete. The image-capture device of the hand-held hydration monitor captures one or more images of the subject's forearm for comparison with the stored images in the data storage component (e.g., a memory card).

The registration circuitry of the hand-held hydration monitor includes software, e.g., featuring-matching software, configured to compare the captured images associated with the forearm of the subject with the stored images on the memory card to determine a registration value. The registration value provides an indication as to whether the captured images of the current location on the forearm register with stored images from previous monitoring or measuring events. For example, a registration value of 1 may indicate perfect registration of the captured images with the stored images, while numbers less than 1 represent some percentage of registration. The micro-impulse radar control circuitry is configured to actuate the micro-impulse radar component in response to the registration value. For example, a registration value of 1 would automatically result in actuation of the micro-impulse radar component. For example, a registration value of less than 1 that meets or exceeds a threshold value, e.g., a registration value of 0.9, might also automatically result in actuation of the micro-impulse radar component. A registration value that does not meet the threshold value, e.g., a registration value less than 0.9, triggers an alert signal to be transmitted to the user interface to indicate that registration of the location on the athlete and the stored location information has not been satisfied. The user interface provides the coach with an alert message, e.g., a red light, indicating that the registration value does not meet the threshold. The user interface provides audio commands instructing the coach to move the hand-held hydration monitor until an appropriate location on the athlete is registered.

Once registration has been satisfied, the micro-impulse radar component is actuated, either automatically by the micro-impulse radar control circuitry or manually by the coach, to transmit one or more pulses towards the location on the subject. One or more reflected pulses are received by a receiver portion of the micro-impulse radar component and processed by a signal processor. The hydration determination circuitry receives the processed information associated with the one or more reflected pulses from a tissue associated with the location on the athlete and compares it with stored information associated with reference reflected pulses correlated with reference hydration states to determine a hydration state of the tissue. The relative hydration state of the athlete is reported to the coach through the user interface of the hand-held hydration monitor. The relative hydration state of the athlete is also wirelessly transmitted to a laptop computer used by the coach, trainer, and/or medical staff to track the hydration states of the athlete over time.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A hand-held hydration monitor comprising:
   a micro-impulse radar component including a pulse generator, a variable beam angle, an adjustable output power, and at least one antenna;
   a data storage component including a calculated fixed beam width, a range of predetermined operating distances of the hand-held hydration monitor, and stored information associated with reference reflected pulses correlated with reference hydration states, wherein the stored information associated with the reference reflected pulses includes reference signal patterns correlated with measured hydration states;
   a user interface including circuitry and a display; and
   a computing component operably coupled to the micro-impulse radar component, the data storage component, and the user interface and including a processor and circuitry, the circuitry including
      micro-impulse radar control circuitry configured to actuate the pulse generator of the micro-impulse radar component to transmit a first set of pulses and at least one second set of pulses towards a target location on a subject;

distance-finding circuitry configured to receive information associated with at least one first reflected pulse from the nearest surface of the target location on the subject in response to the transmitted first set of pulses from the micro-impulse radar component and circuitry configured to determine a distance between the hand-held hydration monitor and the target location on the subject from a time difference between release from the micro-impulse radar component of the transmitted first set of pulses and receipt by the micro-impulse radar component of the at least one first reflected pulse from the nearest surface of the target location on the subject;

beam width control circuitry configured to adjust the variable beam angle of the micro-impulse radar component based on the determined distance to maintain the calculated fixed beam width of the transmitted at least one second set of pulses at the target location on the subject; and hydration determination circuitry configured to receive information associated with one or more second reflected pulses from a target tissue associated with the target location on the subject in response to the transmitted at least one second set of pulses from the micro-impulse radar component, the information associated with the one or more second reflected pulses including reflected signal patterns, and circuitry configured to compare the reflected signal patterns received from the target tissue with the reference signal patterns associated with the measured hydration states to determine a relative hydration state of the target tissue associated with the target location on the subject.

2. The hand-held hydration monitor of claim 1, wherein the distance-finding circuitry includes circuitry configured to determine whether the determined distance is within the range of predetermined operating distances of the hand-held hydration monitor.

3. The hand-held hydration monitor of claim 1, wherein the micro-impulse radar control circuitry includes circuitry configured to automatically actuate the micro-impulse radar component to transmit the at least one second set of pulses towards the target location on the subject if the determined distance is within the range of predetermined operating distances of the hand-held hydration monitor or to prevent actuation of the micro-impulse radar component if the determined distance is outside the range of predetermined operating distances of the hand-held hydration monitor.

4. The hand-held hydration monitor of claim 1, further comprising alert circuitry configured to transmit an alert signal to the user interface in response to the determined distance, wherein the circuitry of the user interface is configured to provide at least one of an audible or optical alert message in response to the transmitted alert signal.

5. The hand-held hydration monitor of claim 4, wherein the alert circuitry includes circuitry configured to transmit the alert signal to the user interface if the determined distance is not within the range of predetermined operating distances of the hand-held hydration monitor; and wherein the circuitry of the user interface is configured to provide one or more instructions related to moving at least one of the hand-held hydration monitor or the subject in response to the transmitted alert signal.

6. The hand-held hydration monitor of claim 1, wherein the micro-impulse radar control circuitry includes circuitry configured to actuate the pulse generator of the micro-impulse radar component to transmit the first set of pulses towards the target location on the subject in response to a user input to the user interface.

7. The hand-held hydration monitor of claim 1, further comprising output power control circuitry configured to adjust the adjustable output power of the micro-impulse radar component in response to the determined distance, wherein an amount of energy transmitted in response to the adjusted adjustable output power is proportional to the square of the determined distance to maintain a specified energy delivery to the target location on the subject from the transmitted at least one second set of pulses.

8. The hand-held hydration monitor of claim 1, wherein the data storage component includes stored identifier information and the circuitry of the computing component includes identification circuitry configured to compare at least one subject identifier and the stored identifier information and to generate an identifier comparison.

9. The hand-held hydration monitor of claim 8, wherein the micro-impulse radar control circuitry includes circuitry configured to actuate the micro-impulse radar component in response to the identifier comparison.

10. The hand-held hydration monitor of claim 1, wherein the data storage component includes stored information associated with the determined relative hydration state of the target tissue associated with the target location on the subject linked to the determined distance and at least one subject identifier.

11. The hand-held hydration monitor of claim 1, wherein the hydration determination circuitry includes circuitry configured to receive the information associated with the one or more second reflected pulses from the target tissue associated with the target location on the subject only when the determined distance is within the range of predetermined operating distances of the hand-held hydration monitor.

12. The hand-held hydration monitor of claim 1, wherein the hydration determination circuitry includes circuitry configured to determine the relative hydration state of the target tissue associated with the target location on the subject based on at least one of a time spectrum of the one or more reflected pulses and a frequency spectrum of the one or more second reflected pulses.

13. The hand-held hydration monitor of claim 1, wherein the hydration determination circuitry includes circuitry configured to determine the relative hydration state of the target tissue associated with the target location on the subject based on a comparison of a frequency spectrum of the one or more second reflected pulses with a frequency spectrum of at least one of the transmitted at least one second set of pulses.

14. The hand-held hydration monitor of claim 1, wherein the micro-impulse radar component includes an adjustable range gate to receive the one or more second reflected pulses at specific time points after transmission of the at least one second set of pulses, the specific time points indicative of different tissue depths; and wherein the hydration determination circuitry includes circuitry configured to determine the relative hydration state of the target tissue associated with the target location on the subject as a function of the different tissue depths.

15. The hand-held hydration monitor of claim 1, further comprising quality assurance circuitry configured to evaluate the quality of the received information associated with the one or more second reflected pulses from the target tissue associated with the target location on the subject against a quality threshold including a signal-to-noise threshold, wherein the micro-impulse radar control circuitry includes circuitry configured to actuate the micro-impulse radar component to transmit one or more additional pulses to the target location on the subject if the evaluated quality of the received one or more second reflected pulses fails to meet the quality threshold.

16. The hand-held hydration monitor of claim 1, further comprising a projector including at least one light-emitting source, the projector configured to project a tracer onto the target location on the subject, wherein a beam width of the projected tracer onto the target location on the subject is the same as the calculated fixed beam width of the transmitted at least one second set of pulses at the target location on the subject.

17. The hand-held hydration monitor of claim 1, further comprising an image-capture device and operably coupled image-capture circuitry configured to actuate the image-capture device to capture at least one image of the target location on the subject in response to actuation of the micro-impulse radar component.

18. A method of determining a hydration state comprising:
    transmitting a first set of pulses from a pulse generator of a micro-impulse radar component of a hydration monitor towards a target location on a subject, the hydration monitor including the micro-impulse radar component including the pulse generator, a variable beam angle, an adjustable output power, and at least one antenna, a data storage component including stored information associated with reference reflected pulses correlate with reference hydration states, the stored information associated with the reference reflected pulses including reference signal patterns correlated with measured hydration states, a user interface, and a computing component including a processor and circuitry;
    receiving information associated with at least one first reflected pulse from a nearest surface of the target location on the subject with the micro-impulse radar component of the hydration monitor in response to the transmitted first set of pulses;
    determining a distance from the hydration monitor to the target location on the subject from a time difference between transmission of the first set of pulses from the hydration monitor and receipt of the at least one first reflected pulse from the nearest surface of the target location on the subject by the hydration monitor;
    adjusting the variable beam angle of the micro-impulse radar component of the hydration monitor based on the determined distance to maintain a calculated fixed beam width at the target location on the subject;
    adjusting the adjustable output power of the micro-impulse radar component of the hydration monitor to adjust an energy transmission proportional to the square of the determined distance to maintain a specified amount of energy reaching the target location on the subject;
    actuating the micro-impulse radar component to transmit at least one second set of pulses having the adjusted beam angle and output power to a target tissue associated with the target location on the subject;
    receiving information associated with one or more second reflected pulses from the target tissue associated with the target location on the subject in response to the transmitted at least one second set of pulses, the information associated with the one or more second reflected pulses including reflected signal patterns;
    comparing the reflected signal patterns received from the target tissue and the reference signal patterns associated with the measured hydration states to determine a relative hydration state of the target tissue associated with the target location on the subject; and
    reporting the determined relative hydration state of the target tissue associated with the target location on the subject with the user interface of the hydration monitor.

19. The method of claim 18, further comprising automatically actuating the micro-impulse radar component to transmit the at least one second set of pulses having the adjusted beam angle and output power to the target tissue associated with the target location on the subject in response to the determined distance if the determined distance is within a range of predetermined operating distances of the hydration monitor or blocking actuation of the micro-impulse radar component in response to the determined distance if the determined distance is not within a range of predetermined operating distances of the hydration monitor.

20. The method of claim 18, further comprising actuating the micro-impulse radar component to transmit the first set of pulses towards the target location on the subject in response to a user input to the user interface.

21. The method of claim 18, further comprising transmitting an alert signal to the user interface of the hydration monitor in response to the determined distance and generating at least one of an audible or optical alert message in response to the transmitted alert signal.

22. The method of claim 21, further comprising generating the alert message including one or more instructions in response to the transmitted alert signal, wherein the one or more instructions include instructions to move at least one of the hydration monitor or the subject in response to the transmitted alert signal to position the hydration monitor and the subject within a range of predetermined operating distances of the hydration monitor.

23. The method of claim 18, further comprising providing user instructions through the user interface.

24. The method of claim 18, further comprising determining a range of operating distances of the hydration monitor based on a range of output power available from the adjustable output power of the micro-impulse radar component and a range of beam angles available from the adjustable beam angle of the micro-impulse radar component.

25. The method of claim 18, further comprising comparing at least one subject identifier with identifier information stored in the data storage component of the hydration monitor to generate an identifier comparison and at least one of actuating the micro-impulse radar component in response to the identifier comparison and transmitting an alert signal to the user interface in response to the identifier comparison.

26. The method of claim 18, further comprising comparing the reflected signal patterns received from the target tissue and the reference signal patterns associated with the measured hydration states based on scaling to a reference distance, wherein an amplitude of the reflected signal patterns received from the target tissue are normalized against an amplitude of a signal pattern acquired at a reference distance.

27. The method of claim 18, further comprising evaluating the quality of the received information associated with the one or more second reflected pulses from the target tissue associated with the target location on the subject against a quality threshold including a signal-to-noise threshold and actuating the micro-impulse radar component to transmit one or more additional pulses to the target tissue associated with the target location on the subject if the evaluated quality of the received one or more second reflected pulses fails to meet the quality threshold.

28. The method of claim 18, further comprising determining the relative hydration state of the target tissue associated with the target location on the subject based on at least one of a time spectrum of the one or more second reflected pulses, a frequency spectrum of the one or more second reflected pulses, or a comparison of a frequency spectrum of the one or more second reflected pulses and a frequency spectrum of at least one of the transmitted at least one second set of pulses.

29. The method of claim 18, further comprising receiving the information associated with the one or more second reflected pulses from the target tissue with an adjustable range gate at specific time points, the specific time points indicative of different tissue depths; and determining the relative hydration state of the target tissue as a function of the different tissue depths.

30. The method of claim 18, further comprising reporting the determined relative hydration state of the target tissue associated with the target location on the subject to wirelessly to a second computing component including a portable personal electronic device.

31. The method of claim 18, further comprising storing the determined relative hydration state of the target tissue associated with the target location on the subject in the data storage component of the hydration monitor linked to at least one subject identifier.

32. The method of claim 31, further comprising storing the determined relative hydration state of the target tissue associated with the target location on the subject in the data storage component of the hydration monitor linked to at least one biometric parameter of the subject.

33. The method of claim 18, further comprising projecting a tracer on the target location on the subject with a projector associated with the hydration monitor, wherein the beam width of the projected tracer at the target location on the subject corresponds to the calculated fixed beam width of the transmitted at least one second set of pulses from the micro-impulse radar component at the target location on the subject.

34. The method of claim 18, further comprising capturing at least one image of the target location on the subject with an image-capture device associated with the hydration monitor and storing the determined relative hydration state of the target tissue associated with the target location on the subject linked to the captured at least one image of the target location on the subject.

35. The method of claim 18, further comprising generating an alert message including one or more instructions for mitigating the determined relative hydration state, wherein the one or more instructions include at least one of administering fluids, administering electrolytes, and cooling the subject.

36. A hand-held hydration monitor comprising:
a micro-impulse radar component including a pulse generator, a variable beam angle, an adjustable output power, at least one receiver, and at least one antenna;
a data storage component including a calculated fixed beam width, a range of predetermined operating distances, and stored information associated with reference reflected pulses correlated with reference hydration states, wherein the stored information associated with the reference reflected pulses includes reference signal patterns correlated with measured hydration states;
a user interface including circuitry and a display; and
a computing component including a processor and circuitry, the circuitry including
micro-impulse radar control circuitry configured to actuate the micro-impulse radar component to transmit a first set of pulses and at least one second set of pulses towards a target location on a subject;
distance-finding circuitry configured to receive information associated with at least one first reflected pulse from a nearest surface of the target location on the subject in response to the transmitted first set of pulses and circuitry to determine a distance between the hand-held hydration monitor and the target location on the subject from a time difference between release from the micro-impulse radar component of the transmitted first set of pulses and receipt by the micro-impulse radar component of the at least one first reflected pulse from the nearest surface of the target location on the subject;
beam width control circuitry configured to adjust the variable beam angle of the micro-impulse radar component based on the determined distance to maintain the calculated fixed beam width of the transmitted at least one second set of pulses at the target location on the subject;
output control circuitry configured to adjust an output power of the micro-impulse radar component in response to the determined distance to maintain a specific energy delivery to the target location on the subject from the transmitted at least one second set of pulses;
hydration determination circuitry configured to receive information associated with one or more second reflected pulses from a target tissue associated with the target location on the subject in response to the transmitted at least one second set of pulses having adjusted beam angle and output power, the information associated with the one or more second reflected pulses including reflected signal patterns, and circuitry configured to compare the reflected signal patterns received from the target tissue with the reference signal patterns associated with the measured hydration states to determine a relative hydration state of the target tissue associated with the target location on the subject.

37. The hand-held hydration monitor of claim 36, wherein the micro-impulse radar control circuitry includes circuitry configured to automatically actuate the micro-impulse radar component to transmit the at least one second set of pulses having adjusted beam angle and output power towards the target location on the subject if the determined distance is within the range of predetermined operating distances of the hand-held hydration monitor or to prevent actuation of the micro-impulse radar component if the determined distance is outside the range of predetermined operating distances of the hand-held hydration monitor.

38. The hand-held hydration monitor of claim 36, further comprising alert circuitry associated with the computing component and configured to transmit an alert signal to the user interface if the determined distance is not within the range of predetermined operating distances of the hand-held hydration monitor; and wherein the circuitry of the user interface is configured to provide one or more instructions instructing a user to move at least one of the hand-held hydration monitor or the subject to a distance that falls within the range of predetermined operating distances in response to the transmitted alert signal.

39. The hand-held hydration monitor of claim 36, further comprising alert circuitry associated with the computing component and configured to transmit an alert signal to the user interface in response to the determined relative hydration state of the target tissue associated with the target location on the subject; and wherein the circuitry of the user interface is configured to provide one or more instructions for mitigating the determined relative hydration state, wherein the one or more instructions include at least one of administering fluids, administering electrolytes, and cooling the subject.

40. The hand-held hydration monitor of claim 36, further comprising quality assurance circuitry associated with the computing component and configured to evaluate the quality of the received information associated with the one or more second reflected pulses from the target tissue associated with the target location on the subject against a quality threshold including a signal-to-noise threshold; and wherein the micro-impulse radar control circuitry includes circuitry configured to actuate the micro-impulse radar component to transmit one or more additional pulses to the target location on the subject if the evaluated quality of the received one or more second pulses fails to meet the quality threshold.

41. The hand-held hydration monitor of claim 36, further comprising a projector operably coupled to the computing component and including at least one light-emitting source, the projector configured to project a tracer onto the target location on the subject, wherein a beam width of the projected tracer onto the target location on the subject is the same as the calculated fixed beam width of the transmitted at least one second set of pulses at the target location on the subject.

* * * * *